(12) United States Patent
Caldarelli et al.

(10) Patent No.: US 8,846,701 B2
(45) Date of Patent: *Sep. 30, 2014

(54) PYRAZOLO-QUINAZOLINES

(75) Inventors: Marina Caldarelli, Milan (IT); Mauro Angiolini, Gavirate (IT); Riccardo Colombo, Oleggio (IT); Teresa Disingrini, Vanzago (IT); Stefano Nuvoloni, Genoa (IT); Helena Posteri, Travedona Monate (IT); Matteo Salsa, Bellinzago Novarese (IT); Marco Silvagni, Segrate (IT)

(73) Assignee: Nerviano Medical Sciences S.R.L., Nerviano (MI) (IT)

( * ) Notice: Subject to any disclaimer, the term of this patent is extended or adjusted under 35 U.S.C. 154(b) by 783 days.

This patent is subject to a terminal disclaimer.

(21) Appl. No.: 13/001,331

(22) PCT Filed: Jun. 17, 2009

(86) PCT No.: PCT/EP2009/057512
§ 371 (c)(1),
(2), (4) Date: Dec. 23, 2010

(87) PCT Pub. No.: WO2009/156315
PCT Pub. Date: Dec. 30, 2009

(65) Prior Publication Data
US 2011/0105542 A1    May 5, 2011

(30) Foreign Application Priority Data

Jun. 26, 2008  (EP) .................................... 08159114

(51) Int. Cl.
*C07D 487/04* (2006.01)
*A61K 31/519* (2006.01)
*C07D 239/70* (2006.01)

(52) U.S. Cl.
CPC ............ *C07D 487/04* (2013.01); *C07D 239/70* (2013.01); *A61K 31/519* (2013.01)
USPC .......................................... 514/267; 544/251

(58) Field of Classification Search
CPC ... C07D 487/04; C07D 239/70; A61K 31/519
USPC .......................................... 514/267; 544/251
See application file for complete search history.

(56) References Cited

U.S. PATENT DOCUMENTS

2010/0216808 A1 * 8/2010 Caruso et al. ............ 514/252.17

FOREIGN PATENT DOCUMENTS

| WO | WO 98/28281 | | 7/1998 | |
| WO | WO 03/070706 A1 | | 8/2003 | |
| WO | WO 2004/104007 | * | 12/2004 | ........... C07D 487/04 |
| WO | WO 2004/104007 A1 | | 12/2004 | |
| WO | WO 2008/074788 A1 | | 6/2008 | |

OTHER PUBLICATIONS

International Search Report dated Aug. 6, 2009 received from the European Patent Office.

* cited by examiner

*Primary Examiner* — Erich A Leeser
(74) *Attorney, Agent, or Firm* — Scully, Scott, Murphy & Presser, P.C.

(57) ABSTRACT

The present invention relates to pyrazolo-quinazolines, characterized by an ortho-substituted-arylamino, heterocyclylamino- or $C_3$-$C_7$ cycloalkylamino residue at 8 position and an aryl, heterocyclyl or $C_3$-$C_7$ cycloalkyl as substituent of a carboxamide at 3 position of the molecule framework. The compounds of this invention modulate the activity of protein kinases and are therefore useful in treating diseases caused by dysregulated protein kinase activity, in particular MPS1/TTK. The present invention also provides methods for preparing these compounds, pharmaceutical compositions comprising these compounds, and methods of treating diseases utilizing pharmaceutical compositions comprising these compounds.

13 Claims, No Drawings

SEQUENCE LISTING

<160> NUMBER OF SEQ ID NOS: 2

<210> SEQ ID NO 1
<211> LENGTH: 80
<212> TYPE: DNA
<213> ORGANISM: Artificial
<220> FEATURE:
<223> OTHER INFORMATION: Forward primer

<400> SEQUENCE: 1
ggggacaagt ttgtacaaaa aagcaggctt actggaagtt ctgttccagg ggcccgaatc      60
cgaggattta agtggcagag      80

```
<210> SEQ ID NO 2
<211> LENGTH: 74
<212> TYPE: DNA
<213> ORGANISM: Artificial
<220> FEATURE:
<223> OTHER INFORMATION: Reverse primer

<400> SEQUENCE: 2
ggggaccact tgtacaaga aagctgggtt ttatttttt ccccttttt tttcaaaagt      60 cttggaggat gaag                                                    74
```

PYRAZOLO-QUINAZOLINES

The present invention relates to certain substituted pyrazolo-quinazoline compounds, which modulate the activity of protein kinases. The compounds of this invention are therefore useful in treating diseases caused by dysregulated protein kinase activity. The present invention also provides methods for preparing these compounds, pharmaceutical compositions comprising these compounds, and methods of treating diseases utilizing pharmaceutical compositions comprising these compounds.

The use of mitotic inhibitors in cancer therapy is a widely accepted clinical strategy for the treatment of a broad range of human cancers. Taxanes (Paclitaxel and Docetaxel) and Vinca Alkaloids (Vincristine and Vinblastine) work by either stabilizing or destabilizing microtubules with catastrophic consequences in cells progressing through mitosis. They are first line therapeutics for several tumour types and second line in cisplatin-refractory ovarian, breast, lung, bladder and esophagus cancers (Taxanes). However, due to the role of microtubules in processes such as cell movement, phagocytosis and axonal transport certain toxicities such as peripheral neuropathy are frequently observed with these agents. Progression through mitosis is a requirement of all proliferating cells and hence cancer therapies that have targets in mitosis are generally applicable to a wide range of tumour types. Several protein kinases play key roles in the orchestration of the cell cycle and some of them are already subject to targeted therapies in the oncology setting including Cdk-2 and Aurora-A. The fidelity of mitosis is of paramount importance and several "checkpoints" exist in normal cells to maintain chromosome integrity during the cell cycle.

The Spindle Assembly Checkpoint (SAC) is specifically required for proper chromosomal segregation into the two daughter cells upon cellular division. It ensures that sister chromatids aligned at the metaphase plate do not separate prior to the bipolar attachment of all duplicated chromosomes to the mitotic spindle (Reviewed in Musacchio A. and Salmon D. Nat Rev Mol Cell Biol, May; 8(5): 379-93, 2007).

Even a single un-aligned chromosome is sufficient to trigger the SAC signal, it is a tightly regulated pathway that ultimately results into the inhibition of the anaphase promoting complex/cyclosome (APC/C)-mediated polyubiquitylation and degradation of two key mitotic components: cyclin B1 and Securin. Securin specifically is required to get sister chromatids separation and anaphase transition, instead cyclin B1 inactivates the master mitotic kinase CDK1 promoting mitotic exit. (Reviewed in Musacchio A. and Salmon D. Nat Rev Mol Cell Biol, May; 8(5): 379-93, 2007).

A large group of proteins has been already identified to play a role in SAC functions: human MPS1 (monopolar spindle 1) kinase, (also known as TTK) has certainly a major role. MPS1 is a dual Tyrosine and Serine/Threonine kinase highly conserved from yeast to mammals. The human genome encodes for just one MPS1 gene family member, which does not have high sequence similarities with other protein kinases.

MPS1 is a cell cycle regulate enzyme that is upregulated and activated in mitosis upon phosphorylation (Stucke V M, et al., Embo J. 21 (7): 1723, 002).

In *Saccharomyces cerevisiae*, MPS1 controls spindle-pole body duplication (Winey M. et al., J. Cell Biol 114:745, 1991), spindle assembly (Jones, M. H. et al., Curr. Biol. 15: 160, 2005) and the spindle assembly checkpoint (Weiss and Winey, J. Cell. Biol 132:111, 1996). Instead in higher eukaryotes the MPS1 kinase activity is mainly involved in SAC regulation and functions (Jelluma, N. et al., Cell 132: 233, 2008).

RNA interference experiments indicate that in the absence of MPS1 the SAC functions are compromised: mitotic length is reduced and cells divide rapidly without methaphase plate alignment, which ultimately causes aberrant aneuploidization, mitotic catastrophe and is not anymore compatible with cellular survival (Jelluma N. et al., Cell 132: 233, 2008; Tighe A. et al., J Cell Biol 2008; Jelluma N. et al., Plos ONE 3 (6): e2415, 2008). Moreover, to support these results, a small molecule ATP-competitor MPS1 inhibitor was described and despite its not clean selectivity profile, it was shown to be capable to inactivate SAC functions, inactivate nocodazole and taxol mediated mitotic arrest and promote cell death mainly in tumorigenic cell lines (Schmidt et al., EMBO Rep, 6(9): to 866, 2005).

Despite that most of the tumors are aneuploid, MPS1 was never found to be mutated in cancer, instead, it has been found upregulated in a number of tumors of different origins like bladder, anaplastic thyroid, breast and prostate cancer (Yuan B. et al, Clin Cancer Res, 12(4): 1121, 2006). Moreover was found in the signature of the top 25 genes over-expressed in CIN and aneuploid tumors which predict clinical outcome in breast and lung cancer, medulloblastoma, glioma, mesothelioma and lymphoma (Carter S L et al., Nat. Genet. 38 (9): 1043, 2006). Finally is highly elevated in metastatic tumors and was found to be over-expressed in p53 mutated breast cancers (Bertheau P. et al., Plos Med 4(3):e90, 2007).

Together with the fact that also other SAC components like MAD2, BUBR1 or BUB1 have been found up-regulated in different tumors (deCarcer G. et al., Curr Med Chem 14(9): 969, 2007), it looks that SAC functions could be required and essential to keep tumoral highly aneuploidy cells capable to segregate and tumoral selectivity of SAC inhibitors is foreseen in particular for highly aneuploid tumors like colon, lung and breast carcinomas (Kops G. J. et al., Nat. Rev Cancer, 5:773, 2005).

Finally, massive aneuploidy induction and SAC deregulation have been shown to reduce tumorigenesis in tumour prone mice sustaining the hypothesis that SAC inhibition could confer tumour growth inhibition (Weaver et al., Cancer Cell 11(1): 25, 2007). Thus, for these reasons, pharmacological attenuation of MPS1 function may have a therapeutic benefit in the treatment of several diverse cancers.

Fused bicyclic pyrimidine derivatives for the treatment of hyperproliferative diseases are disclosed in WO 96/40042 in the name of Pfizer Inc.

Fused polycyclic pyrimidine derivatives as protein kinase inhibitors are also disclosed in WO 98/58926 and WO 98/28281, both in the name of Celltech Therapeutics Ltd.

Fused tricyclic pyrazole compounds known in the art as protein kinase inhibitors are disclosed in WO 03/070236 and WO 03/070706, in the name of Pharmacia Italia S.P.A. and Pharmacia Corp. respectively.

Pyrazolo-quinazoline derivatives having kinase inhibitory activity have been also disclosed in WO 04/104007 and WO 2008074788 in the name of the applicant itself. None of the specific compounds described and claimed therein are object of the present invention.

Despite these developments, there is still need for effective agents for said disease.

The present inventors have now discovered that compounds of the formula (I), described below, are kinase inhibitors and are thus useful in therapy as antitumor agents and lack, in terms of both toxicity and side effects, the aforementioned drawbacks associated with currently available antitumor drugs.

Accordingly, a first object of the present invention is to provide a substituted pyrazolo-quinazoline compound of the formula (I):

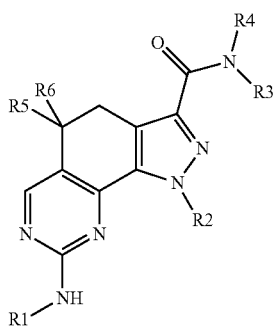

wherein:

R1 is an ortho-substituted-aryl group or a heterocyclyl or $C_3$-$C_7$ cycloalkyl group;

R2 is hydrogen atom or a straight or branched $C_1$-$C_6$ alkyl, $C_2$-$C_6$ alkenyl, $C_2$-$C_6$ alkynyl, $C_3$-$C_7$ cycloalkyl or heterocyclyl group;

R3 is aryl, heterocyclyl or $C_3$-$C_7$ cycloalkyl group;

R4 is hydrogen atom, hydroxyl or $C_1$-$C_6$ alkyl group, which group may be optionally cyclized together with one of the atom of the group which R3 may represent so as to form a fused $C_4$-$C_7$ cyclic group;

R5 and R6: are each independently hydrogen atom, $C_1$-$C_6$ alkyl, or are optionally cyclized together with the carbon atom to which they are bonded so as to form a $C_3$-$C_7$ cycloalkyl group;

wherein the groups ortho-substituted-aryl, aryl, heterocyclyl, $C_3$-$C_7$ cycloalkyl, $C_4$-$C_7$ cycloalkyl, $C_1$-$C_6$ alkyl, $C_2$-$C_6$ alkenyl and $C_2$-$C_6$ alkynyl may be optionally (further) substituted; with the proviso that that the following compounds are excluded:

1H-pyrazolo[4,3-h]quinazoline-3-carboxamide, N-cyclopropyl-4,5-dihydro-1-methyl-8-[(1-methyl-4-piperidinyl) amino] and 1H-pyrazolo[4,3-h]quinazoline-3-carboxamide, N-cyclohexyl-8-(cyclopentylamino)-4,5-dihydro-N-hydroxy-1-methyl;

and the pharmaceutically acceptable salts thereof.

The present invention also provides methods of synthesizing the substituted pyrazolo-quinazoline compounds, represented by the formula (I), prepared through a process consisting of standard synthetic transformations. and isomers, tautomers, hydrates, solvates, complexes, metabolites, prodrugs, carriers, N-oxides.

The present invention also provides a method for treating diseases caused by and/or associated with dysregulated protein kinase activity, hMPS1 (TTK), PLK family members, protein kinase C in different isoforms, Met, PAK-4, PAK-5, STLK-2, DDR-2, Aurora 1, Aurora 2, Bub-1, Chk1, Chk2, HER2, raft, MEK1, MAPK, EGF-R, PDGF-R, FGF-R, IGF-R, PI3K, weel kinase, Src, Abl, Akt, MAPK, ILK, MK-2, IKK-2, Cdc7, Nek, Cdk/cyclin kinase family, which comprises administering to a mammal, in need thereof, an effective amount of a substituted pyrazolo-quinazoline compound represented by the formula (I) as defined above.

Said method is particularly for treating diseases caused by and/or associated with dysregulated human MPS1.

A preferred method of the present invention is to treat a disease caused by and/or associated with dysregulated protein kinase activity selected from the group consisting of cancer, cell proliferative disorders, viral infections, autoimmune and neurodegenerative disorders.

Another preferred method of the present invention is to treat specific types of cancer including but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage including leukaemia, acute lymphocitic leukaemia, acute lymphoblastic leukaemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukaemia; tumors of mesenchymal origin, including fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma mesothelioma, highly aneuploid tumors and tumors which do overexpress mitotic checkpoint components like MPS1, MAD2, MAD1, BUB1, BUBR1, BUB3 and others.

Another preferred method of the present invention is to treat specific cellular proliferation disorders such as, for example, benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

In addition, the method of the present invention also provides tumor angiogenesis and metastasis inhibition as well as the treatment of organ transplant rejection and host versus graft disease.

The present invention also provides a pharmaceutical composition comprising one or more compounds of the formula (I) or a pharmaceutically acceptable salt thereof and a pharmaceutically acceptable excipient, carrier or diluent.

The present invention further provides a pharmaceutical composition comprising a compound of the formula (I) in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

Unless otherwise specified, when referring to the compounds of the formula (I) per se as well as to any pharmaceutical composition thereof or to any therapeutic treatment comprising them, the present invention includes all of the hydrates, solvates, complexes, metabolites, prodrugs, carriers, N-oxides and pharmaceutically acceptable salts of the compounds of this invention.

In other words, if easily obtainable from the compounds of the formula (I) as defined above, also their isomers, tautomers, hydrates, solvates, complexes, metabolites, prodrugs, carriers and N-oxides are object of the present invention.

A metabolite of a compound of the formula (I) is any compound into which this same compound of the formula (I) is converted in vivo, for instance upon administration to a mammal in need thereof. Typically, without however representing a limiting example, upon administration of a compound of the formula (I), this same derivative may be converted into a variety of compounds, for instance including more soluble derivatives like hydroxylated derivatives, which are easily excreted. Hence, depending upon the metabolic pathway thus occurring, any of these hydroxylated derivatives may be regarded as a metabolite of the compounds of the formula (I).

Prodrugs are any covalently bonded compounds, which release in vivo the active parent drug according to the formula (I).

N-oxides are compounds of the formula (I) wherein nitrogen and oxygen are tethered through a dative bond.

If a stereogenic center or another form of an isomeric center is present in a compound of the present invention, all forms of such isomer or isomers, including enantiomers and diastereomers, are intended to be covered herein. Compounds containing a stereogenic center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention.

In cases wherein compounds may exist in tautomeric forms, such as keto-enol tautomers, each tautomeric form is contemplated as being included within this invention whether existing in equilibrium or predominantly in one form. In the present description, unless otherwise specified, with the term "ortho-substituted-aryl", which represents one of the meaning of R1, we intend any aryl group as defined below, bonded to the —NH— moiety, said aryl being always substituted in ortho position, that is on the ring atom adjacent to that bonded to the —NH— moiety, and also optionally substituted in other free positions.

With the term "aryl" we intend aromatic carbocyclic or heteroaryl groups containing from 1 to 2 ring moieties, either fused or linked to each other by single bonds, wherein at least one of the rings is aromatic; if present, any aromatic heteroaryl ring (also known as aromatic heterocyclyl group) comprises a 5 to 6 membered ring containing from 1 to 3 heteroatoms selected among N, O or S. Examples of aryl groups according to the invention are, for instance, phenyl, biphenyl, α- or β-naphthyl, dihydronaphthyl, thienyl, benzothienyl, furyl, benzofuranyl, pyrrolyl, imidazolyl, pyrazolyl, thiazolyl, isothiazolyl, oxazolyl, isoxazolyl, pyridyl, pyrazinyl, pyrimidinyl, pyridazinyl, indolyl, isoindolyl, purinyl, quinolyl, isoquinolyl, dihydroquinolinyl, quinoxalinyl, benzodioxolyl, indanyl, indenyl, triazolyl, and the like.

With the term "heterocyclyl" (also known as "heterocycloalkyl") we intend a 3- to 7-membered, saturated or partially unsaturated carbocyclic ring where one or more carbon atoms are replaced by heteroatoms such as nitrogen, oxygen and sulfur. Non limiting examples of heterocyclyl groups are, for instance, pyrane, pyrrolidine, pyrroline, imidazolidine, imidazolidine, pyrazolidine, pyrazoline, thiazoline, thiazolidine, dihydrofuran, tetrahydrofuran, 1,3-dioxolane, piperidine, piperazine, morpholine and the like.

With the term "$C_3$-$C_7$ cycloalkyl", hence comprehensive of $C_4$-$C_7$ cycloalkyl, we intend, unless otherwise provided, 3- to 7-membered all-carbon monocyclic ring, which may contain one or more double bonds but does not have a completely conjugated π-electron system. Examples of cycloalkyl groups, without limitation, are cyclopropane, cyclobutane, cyclopentane, cyclopentene, cyclohexane, cyclohexene, cyclohexadiene, cycloeptane, cycloeptene, cycloeptadiene.

With the term "straight or branched $C_1$-$C_6$ alkyl", hence comprehensive of $C_1$-$C_4$ alkyl, we intend any of the groups such as, for instance, methyl, ethyl, n-propyl, isopropyl, n-butyl, isobutyl, tert-butyl, sec-butyl, n-pentyl, n-hexyl, and the like.

With the term "straight or branched $C_2$-$C_6$ alkenyl" we intend any of the groups such as, for instance, vinyl, allyl, 1-propenyl, isopropenyl, 1-butenyl, 2-butenyl, 3-butenyl, 2-pentenyl, 1-hexenyl, and the like.

With the term "straight or branched $C_2$-$C_6$ alkynyl" we intend any of the groups such as, for instance, ethynyl, 2-propynyl, 4-pentynyl, and the like.

According to the present invention and unless otherwise provided, any of the above R1, R2, R3, R4, R5 and R6 group may be optionally substituted, in any of their free positions, by one or more groups, for instance 1 to 6 groups, independently selected from: halogen atom, nitro, oxo groups (=O), cyano, $C_1$-$C_6$ alkyl, polyfluorinated alkyl, polyfluorinated alkoxy, alkenyl, alkynyl, hydroxyalkyl, aryl, arylalkyl, heterocyclyl, $C_3$-$C_7$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclyloxycarbonyl, amino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate.

In their turn, whenever appropriate, each of the above substituent may be further substituted by one or more of the aforementioned groups.

In this respect, with the term halogen atom we intend a fluorine, chlorine, bromine or iodine atom.

With the term cyano we intend a —CN residue.

With the term nitro we intend a —NO$_2$ group.

With the term alkenyl or alkynyl we intend any of the aforementioned straight or branched $C_2$-$C_6$ alkyl groups further bearing a double or triple bond. Non limiting examples of alkenyl or alkynyl groups of the invention are, for instance, vinyl, allyl, 1-propenyl, isopropenyl, 1-butenyl, 2-butenyl, 3-butenyl, 2-pentenyl, 1-hexenyl, ethynyl, 2-propynyl, 4-pentynyl, and the like.

With the term polyfluorinated alkyl or alkoxy we intend any of the above straight or branched $C_1$-$C_6$ alkyl or alkoxy groups which are substituted by more than one fluorine atom such as, for instance, trifluoromethyl, trifluoroethyl, 1,1,1,3,3,3-hexafluoropropyl, trifluoromethoxy and the like.

With the term alkoxy, aryloxy, heterocyclyloxy and derivatives thereof we intend any of the above $C_1$-$C_6$ alkyl, aryl or heterocyclyl groups linked to the rest of the molecule through an oxygen atom (—O—).

From all of the above, it is clear to the skilled person that any group which name is a composite name such as, for instance, arylamino has to be intended as conventionally construed by the parts from which it derives, e.g. by an amino group which is further substituted by aryl, wherein aryl is as above defined.

Likewise, any of the terms such as, for instance, alkylthio, alkylamino, dialkylamino, alkoxycarbonyl, alkoxycarbonylamino, heterocyclylcarbonyl, heterocyclylcarbonylamino, cycloalkyloxycarbonyl and the like, include groups wherein the alkyl, alkoxy, aryl, $C_3$-$C_7$ cycloalkyl and heterocyclyl moieties are as above defined.

When R4 is taken together with one of the atom of the cyclic group which R3 represents, they form a 4 to 7 to membered cyclic group such as, for example:

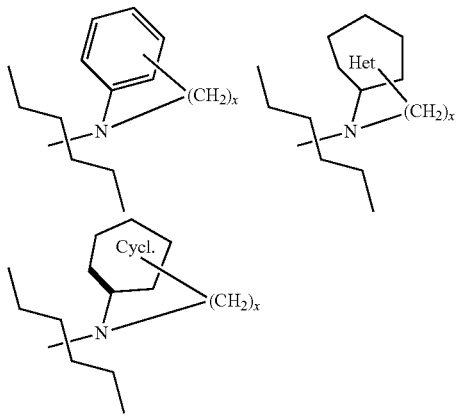

wherein x is an integer from 2 to 4, and R3 is phenyl (aryl), heterocyclyl (Het) or $C_3$-$C_7$ cycloalkyl group (Cycl.); Pharmaceutically acceptable salts of the compounds of the formula (I) include the acid addition salts with inorganic or organic acids, e.g., nitric, hydrochloric, hydrobromic, sulfuric, perchloric, phosphoric, acetic, trifluoroacetic, propionic, glycolic, fumaric, lactic, oxalic, malonic, malic, maleic, tartaric, citric, benzoic, cinnamic, mandelic, methanesulphonic, isethionic and salicylic acid. Preferably, the acid addition salt of the compounds of the invention is selected between the hydrochloride or mesylate salt.

Pharmaceutically acceptable salts of the compounds of the formula (I) also include the salts with inorganic or organic bases, e.g., alkali or alkaline-earth metals, especially sodium, potassium, calcium ammonium or magnesium hydroxides, carbonates or bicarbonates, acyclic or cyclic amines, preferably methylamine, ethylamine, diethylamine, triethylamine, piperidine and the like.

Preferred compounds of the formula (I) are the compounds wherein:

R1 is an ortho-substituted-aryl of the formula A, B or C:

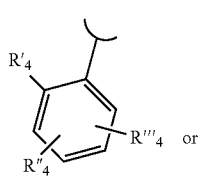

A

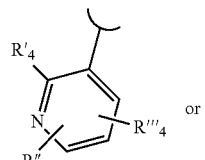

B or

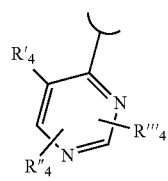

C wherein $R'_4$ is halogen atom, nitro, cyano, $C_1$-$C_6$ alkyl, polyfluorinated alkyl, polyfluorinated alkoxy, alkenyl, alkynyl, hydroxyalkyl, aryl, arylalkyl, heterocyclyl, $C_3$-$C_7$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclyloxycarbonyl, amino, ureido, alkylamino, dialkylamino, arylamino, diarylamino, heterocyclyamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl, alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate or alkylphosphonate; $R''_4$ and $R'''_4$ are independently hydrogen or one of the above meaning for $R'_4$.

Other preferred compounds of the formula (I) are the compounds wherein R1 is a heterocyclyl or $C_5$-$C_7$ cycloalkyl group of the formula D:

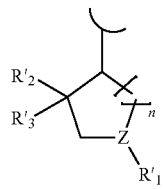

D wherein Z is carbon or nitrogen atom, n is 1, 2 or 3; $R'_1$ is hydrogen atom, $C_1$-$C_6$ alkyl, polyfluorinated alkyl, polyfluorinated alkoxy, alkenyl, alkynyl, hydroxyalkyl, aryl, arylalkyl, heterocyclyl, $C_3$-$C_7$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclyloxycarbonyl, amino, ureido, alkylamino, dialkylamino, arylamino, diarylamino, heterocyclyamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl, alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate; and R'$_2$ and R'$_3$ are each independently hydrogen atom or a C$_1$-C$_3$ alkyl optionally cyclized together with the carbon atom to which they are bonded so as to form a cyclopropyl group.

It is intended that between the square brackets in the group of formula D there can be one or more carbon or hetero atom.

A further preferred class of compounds of the formula (I) are the compounds of the formula (Ia):

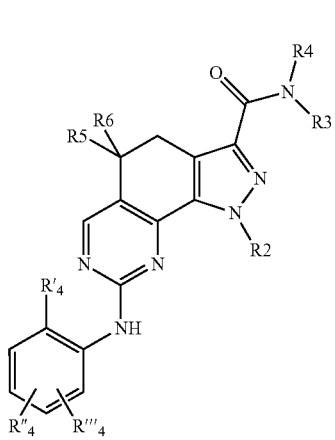

wherein R'$_4$, R''$_4$ and R'''$_4$ are as defined above;
R2 is an optionally substituted straight or branched C$_1$-C$_6$ alkyl or C$_2$-C$_6$ alkenyl group;
R3 is an optionally substituted aryl group;
R4 is hydrogen atom or a C$_1$-C$_6$ alkyl group which may be optionally cyclized together with one of the atom of the group which R3 represents so as to form a fused C$_4$-C$_7$ cyclic group and
R5 and R6 are as defined above, or a pharmaceutically acceptable salt thereof.

A further preferred class of compounds of the formula (I) are the compounds of the formula (Ib):

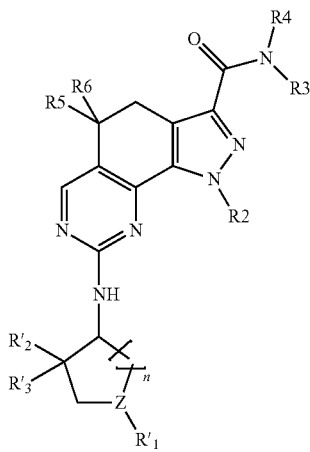

wherein Z is a carbon or nitrogen atom, n is for 2; R'$_1$ is as defined above and R'$_2$ and R'$_3$ are independently hydrogen atom or C$_1$-C$_2$ alkyl group;
R2 is an optionally substituted straight or branched C$_1$-C$_6$ alkyl or C$_2$-C$_6$ alkenyl group;
R3 is an optionally substituted aryl group;
R4 is hydrogen atom or a C$_1$-C$_6$ alkyl group which may be optionally cyclized together with one of the atom of the aryl group which R3 represents so as to form a fused C$_4$-C$_7$ cyclic group and
R5 and R6 are as defined above, or a pharmaceutically acceptable salt thereof.

Another particularly preferred class of compounds of the formula (I) are compounds of the formula (Ia'):

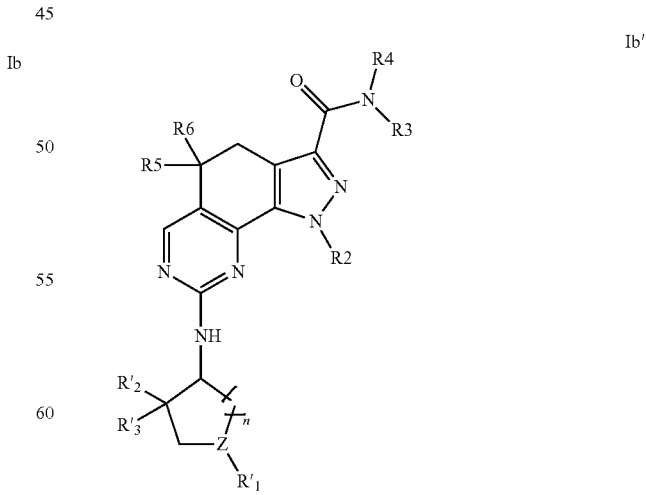

wherein R'$_4$, R''$_4$ and R'''$_4$ are as defined above
R2 is an optionally substituted straight or branched C$_1$-C$_6$ alkyl or C$_2$-C$_6$ alkenyl group;
R3 is as defined above;
R4 is hydrogen atom or a C$_1$-C$_6$ alkyl group which may be optionally cyclized together with one of the atom of the group which R3 represents so as to form a fused C$_4$-C$_7$ cyclic group and
R5 and R6 are hydrogen atom or a methyl group, or a pharmaceutically acceptable salt thereof.

Another particularly preferred class of compounds of the formula (I) are compounds of the formula (Ib'):

wherein Z is a carbon or nitrogen atom, n is 1 or 2, R'$_1$ is as defined above, R'$_2$ and R'$_3$ are independently hydrogen atom or C$_1$-C$_2$ alkyl group;

R2 is an optionally substituted straight or branched $C_1$-$C_6$ alkyl or $C_2$-$C_6$ alkenyl group;

R3 is an optionally substituted aryl group;

R4 is hydrogen atom or $C_1$-$C_6$ alkyl group which may be optionally cyclized together with one of the atom of the aryl group which R3 represents so as to form a fused $C_4$-$C_7$ cyclic group and R5 and R6 are hydrogen atom or a methyl group, or a pharmaceutically acceptable salt thereof.

Preferred specific compounds of the formula (I) are the compounds listed below, or their pharmaceutically acceptable salt:

1) N-(2,6-diethylphenyl)-1-methyl-8-({4-[(1-methylpiperidin-4-yl)carbamoyl]-2-(trifluoromethoxy)phenyl}amino)-4,5-dihydro-1H-pyrazolo[4,3-h]quinazoline-3-carboxamide;
2) N-(2,6-diethylphenyl)-8-({2-methoxy-4-[(1-methylpiperidin-4-yl)carbamoyl]phenyl}amino)-1-methyl-4,5-dihydro-1H-pyrazolo[4,3-h]quinazoline-3-carboxamide;
3) N-(2,6-diethylphenyl)-1-methyl-8-{[4-(4-methylpiperazin-1-yl)-2-(trifluoromethoxy)phenyl]amino}-4,5-dihydro-1H-pyrazolo[4,3-h]quinazoline-3-carboxamide;
4) 8-[(4-carbamoyl-2-methylphenyl)amino]-N-(2,6-diethylphenyl)-1-methyl-4,5-dihydro-1H-pyrazolo[4,3-h]quinazoline-3-carboxamide;
5) N-(2,6-diethylphenyl)-8-{[2-methoxy-4-(4-methylpiperazin-1-yl)phenyl]amino}-1-methyl-4,5-dihydro-1H-pyrazolo[4,3-h]quinazoline-3-carboxamide;
6) 8-[(4-bromo-2-methoxyphenyl)amino]-N-(2,6-diethylphenyl)-1-methyl-4,5-dihydro-1H-pyrazolo[4,3-h]quinazoline-3-carboxamide;
7) N-(2,6-diethylphenyl)-8-[(4-{[3-(dimethylamino)propyl](methyl)amino}-2-methoxyphenyl)amino]-1-methyl-4,5-dihydro-1H-pyrazolo[4,3-h]quinazoline-3-carboxamide;
8) N-(2,6-diethylphenyl)-8-({4-[4-(dimethylamino)piperidin-1-yl]-2-methoxyphenyl}amino)-1-methyl-4,5-dihydro-1H-pyrazolo[4,3-h]quinazoline-3-carboxamide;
9) N-(2,6-diethylphenyl)-8-{[2-methoxy-4-(4-methyl-1,4-diazepan-1-yl)phenyl]amino}-1-methyl-4,5-dihydro-1H-pyrazolo[4,3-h]quinazoline-3-carboxamide;
10) tert-butyl 4-({3-[(2,6-diethylphenyl)carbamoyl]-1-methyl-4,5-dihydro-1H-pyrazolo[4,3-h]quinazolin-8-yl}amino)-3-methoxybenzoate;
11) 4-({3-[(2,6-diethylphenyl)carbamoyl]-1-methyl-4,5-dihydro-1H-pyrazolo[4,3-h]quinazolin-8-yl}amino)-3-methoxybenzoic acid;
12) N-(2,6-diethylphenyl)-8-[(4-{[2-(dimethylamino)ethyl](methyl)amino}-2-methoxyphenyl)amino]-1-methyl-4,5-dihydro-1H-pyrazolo[4,3-h]quinazoline-3-carboxamide;
13) 8-[(4-carbamoyl-2-methoxyphenyl)amino]-N-(2,6-diethylphenyl)-1-methyl-4,5-dihydro-1H-pyrazolo[4,3-h]quinazoline-3-carboxamide;
14) N-(2,6-diethylphenyl)-8-[(4-{[2-(dimethylamino)ethyl]carbamoyl}-2-methoxyphenyl)amino]-1-methyl-4,5-dihydro-1H-pyrazolo[4,3-h]quinazoline-3-carboxamide;
15) 1-methyl-8-({4-[(1-methylpiperidin-4-yl)carbamoyl]-2-(trifluoromethoxy)phenyl}amino)-N-phenyl-4,5-dihydro-1H-pyrazolo[4,3-h]quinazoline-3-carboxamide;
16) N-(2-ethylphenyl)-1-methyl-8-({4-[(1-methylpiperidin-4-yl)carbamoyl]-2-(trifluoromethoxy)phenyl}amino)-4,5-dihydro-1H-pyrazolo[4,3-h]quinazoline-3-carboxamide;
17) N-(2,6-diethylphenyl)-8-[(2-methoxy-4-nitrophenyl)amino]-1-methyl-4,5-dihydro-1H-pyrazolo[4,3-h]quinazoline-3-carboxamide;
18) N-(2,6-diethylphenyl)-8-({2-methoxy-4-[(2-methoxyethyl)carbamoyl]phenyl}amino)-18) 1-methyl-4,5-dihydro-1H-pyrazolo[4,3-h]quinazoline-3-carboxamide;
19) N-(2,6-diethylphenyl)-8-[(4-{[4-(dimethylamino)piperidin-1-yl]carbonyl}-2-methoxyphenyl)amino]-1-methyl-4,5-dihydro-1H-pyrazolo[4,3-h]quinazoline-3-carboxamide;
20) N-(2,6-diethylphenyl)-8-[(2-methoxy-4-{[(2S)-2-(pyrrolidin-1-ylmethyl)pyrrolidin-1-yl]carbonyl}phenyl)amino]-1-methyl-4,5-dihydro-1H-pyrazolo[4,3-h]quinazoline-3-carboxamide;
21) N-(2,6-diethylphenyl)-8-[(2-methoxy-4-{[(2R)-2-(pyrrolidin-1-ylmethyl)pyrrolidin-1-yl]carbonyl}phenyl)amino]-1-methyl-4,5-dihydro-1H-pyrazolo[4,3-h]quinazoline-3-carboxamide;
22) N-(2-ethylphenyl)-8-{[2-methoxy-4-(4-methylpiperazin-1-yl)phenyl]amino}-1-methyl-4,5-dihydro-1H-pyrazolo[4,3-h]quinazoline-3-carboxamide;
23) N-(2,3-dihydro-1H-inden-5-yl)-8-{[2-methoxy-4-(4-methylpiperazin-1-yl)phenyl]amino}-1-methyl-4,5-dihydro-1H-pyrazolo[4,3-h]quinazoline-3-carboxamide;
24) 8-{[2-methoxy-4-(4-methylpiperazin-1-yl)phenyl]amino}-1-methyl-N-(5,6,7,8-tetrahydronaphthalen-1-yl)-4,5-dihydro-1H-pyrazolo[4,3-h]quinazoline-3-carboxamide;
25) 3-(2,3-dihydro-1H-indol-1-ylcarbonyl)-N-[2-methoxy-4-(4-methylpiperazin-1-yl)phenyl]-1-methyl-4,5-dihydro-1H-pyrazolo[4,3-h]quinazolin-8-amine;
26) N-(2,6-dimethylphenyl)-8-{[2-methoxy-4-(4-methylpiperazin-1-yl)phenyl]amino}-1-methyl-4,5-dihydro-1H-pyrazolo[4,3-h]quinazoline-3-carboxamide;
27) N-(2-ethyl-6-methylphenyl)-8-{[2-methoxy-4-(4-methylpiperazin-1-yl)phenyl]amino}-1-methyl-4,5-dihydro-1H-pyrazolo[4,3-h]quinazoline-3-carboxamide;
28) 8-{[2-methoxy-4-(4-methylpiperazin-1-yl)phenyl]amino}-N-(2-methoxyphenyl)-1-methyl-4,5-dihydro-1H-pyrazolo[4,3-h]quinazoline-3-carboxamide;
29) N-1,3-benzothiazol-5-yl-8-{[2-methoxy-4-(4-methylpiperazin-1-yl)phenyl]amino}-1-methyl-4,5-dihydro-1H-pyrazolo[4,3-h]quinazoline-3-carboxamide;
30) N-(2-chloro-6-methylphenyl)-8-{[2-methoxy-4-(4-methylpiperazin-1-yl)phenyl]amino}-1-methyl-4,5-dihydro-1H-pyrazolo[4,3-h]quinazoline-3-carboxamide;
31) N-[2,6-bis(1-methylethyl)phenyl]-8-{[2-methoxy-4-(4-methylpiperazin-1-yl)phenyl]amino}-1-methyl-4,5-dihydro-1H-pyrazolo[4,3-h]quinazoline-3-carboxamide;
32) N-(2,6-diethylphenyl)-8-({4-[(2-hydroxyethyl)carbamoyl]-2-methoxyphenyl}amino)-1-methyl-4,5-dihydro-1H-pyrazolo[4,3-h]quinazoline-3-carboxamide;
33) 8-{[2-cyano-4-(4-methylpiperazin-1-yl)phenyl]amino}-N-(2,6-diethylphenyl)-1-methyl-4,5-dihydro-1H-pyrazolo[4,3-h]quinazoline-3-carboxamide;
34) 8-{[2-cyano-4-(4-methyl-1,4-diazepan-1-yl)phenyl]amino}-N-(2,6-diethylphenyl)-1-methyl-4,5-dihydro-1H-pyrazolo[4,3-h]quinazoline-3-carboxamide;
35) 8-[(2-chlorophenyl)amino]-N-(2,6-diethylphenyl)-1-methyl-4,5-dihydro-1H-pyrazolo[4,3-h]quinazoline-3-carboxamide;
36) 8-[(4-bromo-2-cyanophenyl)amino]-N-(2,6-diethylphenyl)-1-methyl-4,5-dihydro-1H-pyrazolo[4,3-h]quinazoline-3-carboxamide;
37) 8-[(2-bromophenyl)amino]-N-(2,6-diethylphenyl)-1-methyl-4,5-dihydro-1H-pyrazolo[4,3-h]quinazoline-3-carboxamide;
38) N-(2,6-diethylphenyl)-8-[(2-methoxyphenyl)amino]-1-methyl-4,5-dihydro-1H-pyrazolo[4,3-h]quinazoline-3-carboxamide;

39) N-(2,6-diethylphenyl)-8-({2-methoxy-4-[(3-pyrrolidin-1-ylazetidin-1-yl)carbonyl]phenyl}amino)-1-methyl-4,5-dihydro-1H-pyrazolo[4,3-h]quinazoline-3-carboxamide;

40) N-(2,6-diethylphenyl)-8-{[2-methoxy-4-(3-pyrrolidin-1-ylazetidin-1-yl)phenyl]amino}-1-methyl-4,5-dihydro-1H-pyrazolo[4,3-h]quinazoline-3-carboxamide;

41) N-(2,6-dimethylphenyl)-8-{[2-methoxy-4-(4-methylpiperazin-1-yl)phenyl]amino}-1,5,5-trimethyl-4,5-dihydro-1H-pyrazolo[4,3-h]quinazoline-3-carboxamide;

42) N-(2,6-diethylphenyl)-8-({2-methoxy-4-[(4-methyl-1,4-diazepan-1-yl)carbonyl]phenyl}amino)-1-methyl-4,5-dihydro-1H-pyrazolo[4,3-h]quinazoline-3-carboxamide;

43) N-(2,6-diethylphenyl)-8-({2-methoxy-4-[(2-methoxyethyl)amino]phenyl}amino)-1-methyl-4,5-dihydro-1H-pyrazolo[4,3-h]quinazoline-3-carboxamide;

44) 8-[(4-bromo-2-methoxyphenyl)amino]-N-(2,6-dimethylphenyl)-1,5,5-trimethyl-4,5-dihydro-1H-pyrazolo[4,3-h]quinazoline-3-carboxamide;

45) N-(2,6-diethylphenyl)-8-[(2-iodophenyl)amino]-1-methyl-4,5-dihydro-1H-pyrazolo[4,3-h]quinazoline-3-carboxamide;

46) N-(2,6-diethylphenyl)-8-({4-[(3S)-3-(dimethylamino)pyrrolidin-1-yl]-2-methoxyphenyl}amino)-1-methyl-4,5-dihydro-1H-pyrazolo[4,3-h]quinazoline-3-carboxamide;

47) N-(2,6-diethylphenyl)-8-({4-[(3R)-3-(dimethylamino)pyrrolidin-1-yl]-2-methoxyphenyl}amino)-1-methyl-4,5-dihydro-1H-pyrazolo[4,3-h]quinazoline-3-carboxamide;

48) 8-[(5-bromo-2-methoxyphenyl)amino]-N-(2,6-diethylphenyl)-1-methyl-4,5-dihydro-1H-pyrazolo[4,3-h]quinazoline-3-carboxamide;

49) N-(2,6-diethylphenyl)-8-{[2-methoxy-5-(4-methylpiperazin-1-yl)phenyl]amino}-1-methyl-4,5-dihydro-1H-pyrazolo[4,3-h]quinazoline-3-carboxamide;

50) N-(2,6-diethylphenyl)-8-({4-[4-(2-hydroxyethyl)piperazin-1-yl]-2-methoxyphenyl}amino)-1-methyl-4,5-dihydro-1H-pyrazolo[4,3-h]quinazoline-3-carboxamide;

51) N-(2,6-diethylphenyl)-8-[(4-{[2-(dimethylamino)ethyl]amino}-2-methoxyphenyl)amino]-1-methyl-4,5-dihydro-1H-pyrazolo[4,3-h]quinazoline-3-carboxamide;

52) N-(2,6-diethylphenyl)-8-({2-methoxy-4-[(4-methylpiperazin-1-yl)carbonyl]phenyl}amino)-1-methyl-4,5-dihydro-1H-pyrazolo[4,3-h]quinazoline-3-carboxamide;

53) tert-butyl 4-({3-[(2,6-diethylphenyl)carbamoyl]-1-methyl-4,5-dihydro-1H-pyrazolo[4,3-h]quinazolin-8-yl}amino)piperidine-1-carboxylate;

54) N-(2,6-diethylphenyl)-1-methyl-8-(piperidin-4-ylamino)-4,5-dihydro-1H-pyrazolo[4,3-h]quinazoline-3-carboxamide, hydrochloride;

55) N-(2,6-diethylphenyl)-8-{[1-(ethenylsulfonyl)piperidin-4-yl]amino}-1-methyl-4,5-dihydro-1H-pyrazolo[4,3-h]quinazoline-3-carboxamide;

56) N-(2,6-diethylphenyl)-1-methyl-8-[(1-{[2-(methylamino)ethyl]sulfonyl}piperidin-4-yl)amino]-4,5-dihydro-1H-pyrazolo[4,3-h]quinazoline-3-carboxamide;

57) N-(2,6-diethylphenyl)-1-methyl-8-{[1-(methylsulfonyl)piperidin-4-yl]amino}-4,5-dihydro-1H-pyrazolo[4,3-h]quinazoline-3-carboxamide;

58) 8-[(1-acetylpiperidin-4-yl)amino]-N-(2,6-diethylphenyl)-1-methyl-4,5-dihydro-1H-pyrazolo[4,3-h]quinazoline-3-carboxamide;

59) N-(2,6-diethylphenyl)-1-methyl-8-{[1-(phenylcarbonyl)piperidin-4-yl]amino}-4,5-dihydro-1H-pyrazolo[4,3-h]quinazoline-3-carboxamide;

60) N-(2,6-diethylphenyl)-1-methyl-8-({1-[(1-methylpiperidin-4-yl)carbonyl]piperidin-4-yl}amino)-4,5-dihydro-1H-pyrazolo[4,3-h]quinazoline-3-carboxamide;

61) N-(2,6-diethylphenyl)-1-methyl-8-({1-[(4-methylpiperazin-1-yl)carbonyl]piperidin-4-yl}amino)-4,5-dihydro-1H-pyrazolo[4,3-h]quinazoline-3-carboxamide;

62) N-(2,6-diethylphenyl)-1-methyl-8-{[1-(phenylsulfonyl)piperidin-4-yl]amino}-4,5-dihydro-1H-pyrazolo[4,3-h]quinazoline-3-carboxamide;

63) 8-[(1-acryloylpiperidin-4-yl)amino]-N-(2,6-diethylphenyl)-1-methyl-4,5-dihydro-1H-pyrazolo[4,3-h]quinazoline-3-carboxamide;

64) 8-[(1-benzylpiperidin-4-yl)amino]-N-(2,6-diethylphenyl)-1-methyl-4,5-dihydro-1H-pyrazolo[4,3-h]quinazoline-3-carboxamide;

65) 8-({1-[(3-chloropropyl)sulfonyl]piperidin-4-yl}amino)-N-(2,6-diethylphenyl)-1-methyl-4,5-dihydro-1H-pyrazolo[4,3-h]quinazoline-3-carboxamide;

66) N-(2,6-diethylphenyl)-1-methyl-8-{[1-(N-methyl-beta-alanyl)piperidin-4-yl]amino}-4,5-dihydro-1H-pyrazolo[4,3-h]quinazoline-3-carboxamide;

67) N-(2,6-diethylphenyl)-8-{[1-(N,N-dimethyl-beta-alanyl)piperidin-4-yl]amino}-1-methyl-4,5-dihydro-1H-pyrazolo[4,3-h]quinazoline-3-carboxamide;

68) N-(2,6-diethylphenyl)-8-[(1-ethylpiperidin-4-yl)amino]-1-methyl-4,5-dihydro-1H-pyrazolo[4,3-h]quinazoline-3-carboxamide;

69) N-(2,6-diethylphenyl)-1-methyl-8-[(1-{[3-(methylamino)propyl]sulfonyl}piperidin-4-yl)amino]-4,5-dihydro-1H-pyrazolo[4,3-h]quinazoline-3-carboxamide, hydrochloride;

70) N-(2,6-diethylphenyl)-1-methyl-8-[(1-{[2-(4-methylpiperazin-1-yl)ethyl]sulfonyl}piperidin-4-yl)amino]-4,5-dihydro-1H-pyrazolo[4,3-h]quinazoline-3-carboxamide;

71) N-(2,6-diethylphenyl)-8-[(1-{[2-(dimethylamino)ethyl]sulfonyl}piperidin-4-yl)amino]-1-methyl-4,5-dihydro-1H-pyrazolo[4,3-h]quinazoline-3-carboxamide;

72) N-(2,6-diethylphenyl)-1-methyl-8-({1-[(2-piperidin-1-ylethyl)sulfonyl]piperidin-4-yl}amino)-4,5-dihydro-1H-pyrazolo[4,3-h]quinazoline-3-carboxamide;

73) N-(2,6-diethylphenyl)-1-methyl-8-({1-[(2-morpholin-4-ylethyl)sulfonyl]piperidin-4-yl}amino)-4,5-dihydro-1H-pyrazolo[4,3-h]quinazoline-3-carboxamide;

74) N-(2,6-diethylphenyl)-1-methyl-8-({1-[(2-pyrrolidin-1-ylethyl)sulfonyl]piperidin-4-yl}amino)-4,5-dihydro-1H-pyrazolo[4,3-h]quinazoline-3-carboxamide;

75) 8-({1-[(2-aminoethyl)sulfonyl]piperidin-4-yl}amino)-N-(2,6-diethylphenyl)-1-methyl-4,5-dihydro-1H-pyrazolo[4,3-h]quinazoline-3-carboxamide;

76) N-(2,6-diethylphenyl)-8-{[2-methoxy-4(4-pyrrolidin-1-ylpiperidin-1-yl)phenyl]amino}-1-methyl-4,5-dihydro-1H-pyrazolo[4,3-h]quinazoline-3-carboxamide;

77) N-(2,6-diethylphenyl)-8-{[2-methoxy-4-(tetrahydro-2H-pyran-4-ylamino)phenyl]amino}-1-methyl-4,5-dihydro-1H-pyrazolo[4,3-h]quinazoline-3-carboxamide;

78) tert-butyl 4-({3-[(2,6-diethylphenyl)carbamoyl]-1-methyl-4,5-dihydro-1H-pyrazolo[4,3-h]quinazolin-8-yl}amino)-3-methyl benzoate;

79) N-(2,6-diethylphenyl)-8-({2-methoxy-4-[(1-methylpiperidin-4-yl)amino]phenyl}amino)-1-methyl-4,5-dihydro-1H-pyrazolo[4,3-h]quinazoline-3-carboxamide;

80) 8-({1-[(3-chloromethyl)sulfonyl]piperidin-4-yl}amino)-N-(2,6-diethylphenyl)-1-methyl-4,5-dihydro-1H-pyrazolo[4,3-h]quinazoline-3-carboxamide;

81) 8-[(4-amino-2-methoxyphenyl)amino]-N-(2,6-diethylphenyl)-1-methyl-4,5-dihydro-1H-pyrazolo[4,3-h]quinazoline-3-carboxamide;

82) N-(2,6-diethylphenyl)-8-[(2-methoxy-4-{[(1-methylpiperidin-4-yl)carbonyl]amino}phenyl)amino]-1-methyl-4,5-dihydro-1H-pyrazolo[4,3-h]quinazoline-3-carboxamide;

83) 4-({3-[(2,6-diethylphenyl)carbamoyl]-1-methyl-4,5-dihydro-1H-pyrazolo[4,3-h]quinazolin-8-yl}amino)-3-methylbenzoic acid;

84) N-(2,6-diethylphenyl)-8-[(4-{[4-(dimethylamino)piperidin-1-yl]carbonyl}-2-methylphenyl)amino]-1-methyl-4,5-dihydro-1H-pyrazolo[4,3-h]quinazoline-3-carboxamide;

85) N-(2,6-diethylphenyl)-8-[(4-{[2-(dimethylamino)ethyl]carbamoyl}-2-methylphenyl)amino]-1-methyl-4,5-dihydro-1H-pyrazolo[4,3-h]quinazoline-3-carboxamide;

86) N-(2,6-diethylphenyl)-8-[(4-{[4-(dimethylamino)butanoyl]amino}-2-methoxyphenyl)amino]-1-methyl-4,5-dihydro-1H-pyrazolo[4,3-h]quinazoline-3-carboxamide trifluoroacetate;

87) 8-[(4-bromo-2-chlorophenyl)amino]-N-(2,6-diethylphenyl)-1-methyl-4,5-dihydro-1H-pyrazolo[4,3-h]quinazoline-3-carboxamide;

88) 8-{[2-chloro-4-(4-methylpiperazin-1-yl)phenyl]amino}-N-(2,6-diethylphenyl)-1-methyl-4,5-dihydro-1H-pyrazolo[4,3-h]quinazoline-3-carboxamide;

89) N-(2,6-diethylphenyl)-1-methyl-8-[(2-methyl-4-{[(2R)-2-(pyrrolidin-1-ylmethyl)pyrrolidin-1-yl]carbonyl}phenyl)amino]-4,5-dihydro-1H-pyrazolo[4,3-h]quinazoline-3-carboxamide;

90) 8-[(2-chloro-4-{[3-(dimethylamino)propyl](methyl)amino}phenyl)amino]-N-(2,6-diethylphenyl)-1-methyl-4,5-dihydro-1H-pyrazolo[4,3-h]quinazoline-3-carboxamide;

91) N-(2,6-diethylphenyl)-1-methyl-8-({2-methyl-4-[(4-methyl-1,4-diazepan-1-yl)carbonyl]phenyl}amino)-4,5-dihydro-1H-pyrazolo[4,3-h]quinazoline-3-carboxamide;

92) 8-({2-chloro-4-[4-(dimethylamino)piperidin-1-yl]phenyl}amino)-N-(2,6-diethylphenyl)-1-methyl-4,5-dihydro-1H-pyrazolo[4,3-h]quinazoline-3-carboxamide;

93) N-(2,6-diethylphenyl)-8-({4-[(4-hydroxycyclohexyl)amino]-2-methoxyphenyl}amino)-1-methyl-4,5-dihydro-1H-pyrazolo[4,3-h]quinazoline-3-carboxamide;

94) N-(2,6-diethylphenyl)-8-({2-methoxy-4-[(3-piperidin-1-ylpropanoyl)amino]phenyl}amino)-1-methyl-4,5-dihydro-1H-pyrazolo[4,3-h]quinazoline-3-carboxamide;

95) N-(2,6-diethylphenyl)-1-methyl-8-({2-methyl-4-[(4-pyrrolidin-1-ylpiperidin-1-yl)carbonyl]phenyl}amino)-4,5-dihydro-1H-pyrazolo[4,3-h]quinazoline-3-carboxamide;

96) 8-{[4-(1-azabicyclo[2.2.2]oct-3-ylamino)-2-methoxyphenyl]amino}-N-(2,6-diethylphenyl)-1-methyl-4,5-dihydro-1H-pyrazolo[4,3-h]quinazoline-3-carboxamide;

97) 8-{[4-({[tert-butyl(dimethyl)silyl]oxy}methyl)-2-methoxyphenyl]amino}-N-(2,6-diethylphenyl)-1-methyl-4,5-dihydro-1H-pyrazolo[4,3-h]quinazoline-3-carboxamide;

98) N-(2,6-diethylphenyl)-8-{[4-(hydroxymethyl)-2-methoxyphenyl]amino}-1-methyl-4,5-dihydro-1H-pyrazolo[4,3-h]quinazoline-3-carboxamide;

99) N-(2,6-diethylphenyl)-8-({2-methoxy-4-[(4-methylpiperazin-1-yl)methyl]phenyl}amino)-1-methyl-4,5-dihydro-1H-pyrazolo[4,3-h]quinazoline-3-carboxamide;

100) tert-butyl 4-({3-[(2,6-diethylphenyl)carbamoyl]-1-methyl-4,5-dihydro-1H-pyrazolo[4,3-h]quinazolin-8-yl}amino)-3,3-dimethylpiperidine-1-carboxylate;

101) N-(2,6-diethylphenyl)-8-[(3,3-dimethyl-1-{[2-(methylamino)ethyl]sulfonyl}piperidin-4-yl)amino]-1-methyl-4,5-dihydro-1H-pyrazolo[4,3-h]quinazoline-3-carboxamide;

102) N-(2,6-diethylphenyl)-1-methyl-8-({1-[(2,2,2-trifluoroethyl)sulfonyl]piperidin-4-yl}amino)-4,5-dihydro-1H-pyrazolo[4,3-h]quinazoline-3-carboxamide;

103) N-(2,6-diethylphenyl)-1-methyl-8-({1-[(trifluoromethyl)sulfonyl]piperidin-4-yl}amino)-4,5-dihydro-1H-pyrazolo[4,3-h]quinazoline-3-carboxamide;

104) N-(2,6-diethylphenyl)-1-methyl-8-{[1-(1H-pyrazol-4-ylsulfonyl)piperidin-4-yl]amino}-4,5-dihydro-1H-pyrazolo[4,3-h]quinazoline-3-carboxamide;

105) N-(2,6-diethylphenyl)-8-{[1-(1H-imidazol-4-ylsulfonyl)piperidin-4-yl]amino}-1-methyl-4,5-dihydro-1H-pyrazolo[4,3-h]quinazoline-3-carboxamide;

106) N-(2,6-diethylphenyl)-1-methyl-8-({1-[(4-methyl-3,4-dihydro-2H-1,4-benzoxazin-7-yl)sulfonyl]piperidin-4-yl}amino)-4,5-dihydro-1H-pyrazolo[4,3-h]quinazoline-3-carboxamide;

107) N-(2,6-diethylphenyl)-8-{[1-(dimethylsulfamoyl)piperidin-4-yl]amino}-1-methyl-4,5-dihydro-1H-pyrazolo[4,3-h]quinazoline-3-carboxamide;

108) N-(2,6-diethylphenyl)-1-methyl-8-({1-[(1-methyl-1H-imidazol-4-yl)sulfonyl]piperidin-4-yl}amino)-4,5-dihydro-1H-pyrazolo[4,3-h]quinazoline-3-carboxamide;

109) N-(2,6-diethylphenyl)-1-methyl-8-{[1-(pyridin-3-ylsulfonyl)piperidin-4-yl]amino}-4,5-dihydro-1H-pyrazolo[4,3-h]quinazoline-3-carboxamide;

110) 8-[(1-{[4-(acetylamino)phenyl]sulfonyl}piperidin-4-yl)amino]-N-(2,6-diethylphenyl)-1-methyl-4,5-dihydro-1H-pyrazolo[4,3-h]quinazoline-3-carboxamide;

111) 8-({1-[(4-aminophenyl)sulfonyl]piperidin-4-yl}amino)-N-(2,6-diethylphenyl)-1-methyl-4,5-dihydro-1H-pyrazolo[4,3-h]quinazoline-3-carboxamide hydrochloride;

112) N-(2,6-diethylphenyl)-8-({1-[(2-hydroxyethyl)sulfonyl]piperidin-4-yl}amino)-1-methyl-4,5-dihydro-1H-pyrazolo[4,3-h]quinazoline-3-carboxamide;

113) N-(2,6-diethylphenyl)-8-({1-[(2-methoxyethyl)sulfonyl]piperidin-4-yl}amino)-1-methyl-4,5-dihydro-1H-pyrazolo[4,3-h]quinazoline-3-carboxamide;

114) 8-[(trans-4-aminocyclohexyl)amino]-N-(2,6-diethylphenyl)-1-methyl-4,5-dihydro-1H-pyrazolo[4,3-h]quinazoline-3-carboxamide;

115) N-(2,6-diethylphenyl)-8-[(1-{[2-(ethylamino)ethyl]sulfonyl}piperidin-4-yl)amino]-1-methyl-4,5-dihydro-1H-pyrazolo[4,3-h]quinazoline-3-carboxamide;

116) N-(2,6-diethylphenyl)-1-methyl-8-({1-[(5-methylisoxazol-4-yl)carbonyl]piperidin-4-yl}amino)-4,5-dihydro-1H-pyrazolo[4,3-h]quinazoline-3-carboxamide;

117) N-(2,6-diethylphenyl)-1-methyl-8-({1-[(1-methyl-1H-imidazol-4-yl)carbonyl]piperidin-4-yl}amino)-4,5-dihydro-1H-pyrazolo[4,3-h]quinazoline-3-carboxamide;

118) N-(2,6-diethylphenyl)-1-methyl-8-{[1-(pyrimidin-4-ylcarbonyl)piperidin-4-yl]amino}-4,5-dihydro-1H-pyrazolo[4,3-h]quinazoline-3-carboxamide;

119) N-(2,6-diethylphenyl)-1-methyl-8-{[1-(1H-pyrrol-2-ylcarbonyl)piperidin-4-yl]amino}-4,5-dihydro-1H-pyrazolo[4,3-h]quinazoline-3-carboxamide;

120) N-(2,6-diethylphenyl)-8-{[1-(1H-imidazol-4-ylcarbonyl)piperidin-4-yl]amino}-1-methyl-4,5-dihydro-1H-pyrazolo[4,3-h]quinazoline-3-carboxamide;

121) N-(2,6-diethylphenyl)-1-methyl-8-{[1-(pyridin-3-ylcarbonyl)piperidin-4-yl]amino}-4,5-dihydro-1H-pyrazolo[4,3-h]quinazoline-3-carboxamide;

122) N-(2,6-diethylphenyl)-1-methyl-8-{[1-(pyridin-2-ylcarbonyl)piperidin-4-yl]amino}-4,5-dihydro-1H-pyrazolo[4,3-h]quinazoline-3-carboxamide;

123) N-(2,6-diethylphenyl)-1-methyl-8-{[1-(1H-pyrazol-4-ylcarbonyl)piperidin-4-yl]amino}-4,5-dihydro-1H-pyrazolo[4,3-h]quinazoline-3-carboxamide;
124) N-(2,6-diethylphenyl)-1-methyl-8-{[1-(thiophen-3-ylcarbonyl)piperidin-4-yl]amino}-4,5-dihydro-1H-pyrazolo[4,3-h]quinazoline-3-carboxamide;
125) N-(2,6-diethylphenyl)-1-methyl-8-{[1-(pyridin-4-ylcarbonyl)piperidin-4-yl]amino}-4,5-dihydro-1H-pyrazolo[4,3-h]quinazoline-3-carboxamide;
126) N-(2,6-diethylphenyl)-1-methyl-8-{[1-(1H-pyrrol-3-ylcarbonyl)piperidin-4-yl]amino}-4,5-dihydro-1H-pyrazolo[4,3-h]quinazoline-3-carboxamide;
127) N-(2,6-diethylphenyl)-1-methyl-8-{[trans-4-({[2-(methylamino)ethyl]sulfonyl}amino)cyclohexyl]amino}-4,5-dihydro-1H-pyrazolo[4,3-h]quinazoline-3-carboxamide and
128) N-(2,6-diethylphenyl)-8-[(4-formyl-2-methoxyphenyl)amino]-1-methyl-4,5-dihydro-1H-pyrazolo[4,3-h]quinazoline-3-carboxamide.

For a reference to any specific compound of the formula (I) of the invention, optionally in the form of a pharmaceutically acceptable salt, see the experimental section and claims.

The present inventions also provides processes for the preparation of compounds of the formula (I) as defined above.

Accordingly, a process of the present invention comprises:
st.A1) reacting a compound of the formula (II):

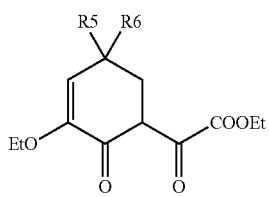

II wherein R5 and R6 are as defined above, with an hydrazine derivative of the formula (III):

 III wherein R2 is as defined above, in the presence of acetic acid, if necessary alkylating a resultant compound of the formula (IV):

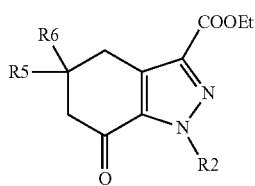

IV wherein R5 and R6 are as defined above and R2 is hydrogen, with a compound of the formula (V):

 V wherein Y is a suitable leaving group such as mesyl, tosyl, halogen atom, and R2 is as defined above but not hydrogen atom;
st.A2) reacting the resultant compound of the formula (IV) as defined above, if necessary after the alkylation, with dimethylformamide-di-tert-butylacetale or dimethylformamide-di-isopropylacetale;

st.A3) reacting the resultant compound of the formula (VI)

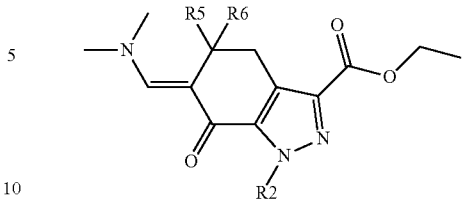

VI wherein R2, R5 and R6 are as defined above, according to any one of the alternative steps (st.A3a) or (st.A3b):
st.A3a) either with guanidine or a salt thereof, and replacing the amino group of the resultant compound of the formula (VII):

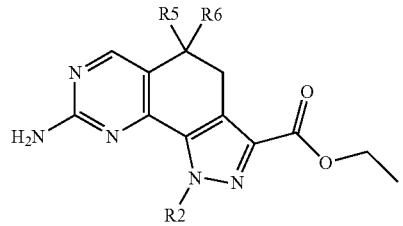

VII wherein R2, R5 and R6 are as defined above, with iodine, by reacting with iso-amylnitrite and diiodomethane or cesium iodide, in the presence of iodine and CuI, and then reacting the resulting iodo-derivative of the formula (VIII):

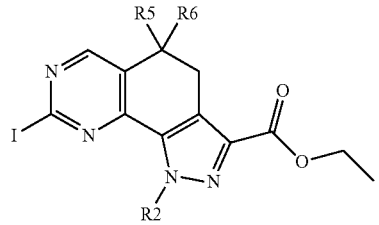

VIII wherein R1, R2, R5 and R6 are as defined above, with a compound of the formula R1-NH$_2$ (IX) wherein R1 is as defined above;
st.A3b) or with a guanidine derivative of the formula (XI):

 XI wherein R1 is as defined above;
st.A4) hydrolysing the resultant compound of the formula (X):

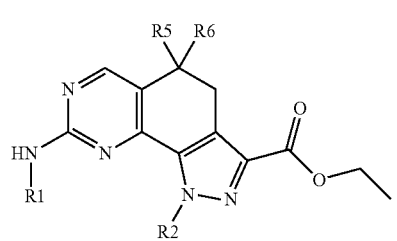

X wherein R1, R2, R5 and R6 are as defined above, in acidic or basic condition;

st.A5) reacting the resultant compound of the formula (XIII) or the corresponding salt:

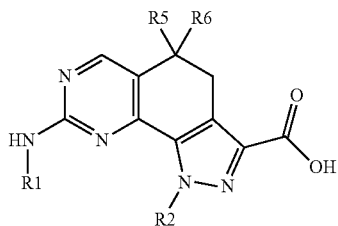

XIII wherein R1, R2, R5 and R6 are as defined above with an amine of the formula (XIV):

R3R4N—H        XIV wherein R3 and R4 are as defined above, in presence of the suitable condensing agents, to give a compound of the formula (I):

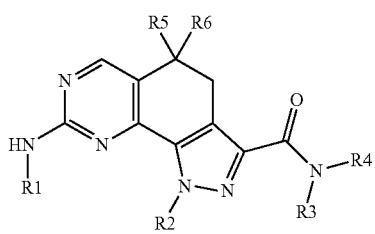

I wherein R1, R2, R3, R4, R5 and R6 are as defined above, and optionally converting a compound of the formula (I) into another different compound of the formula (I), and, if desired, converting a compound of the formula (I) into a pharmaceutically acceptable salt thereof or converting a salt into the free compound (I).

Another process of the present inventions comprises:

st.A4a1) reacting a compound of formula (X) as defined above with an amine of formula (IX) as defined above, in presence of a strong base, to give a compound of formula (I):

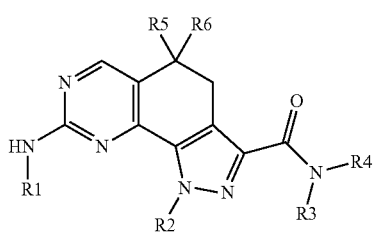

I wherein R1, R2, R3, R4, R5 and R6 are as defined above, and optionally converting a compound of the formula (I) into another different compound of the formula (I), and, if desired, converting a compound of the formula (I) into a pharmaceutically acceptable salt thereof or converting a salt into the free compound (I).

Another process of the present invention comprises:

st.B1) hydrolysing a compound of (VIII) as defined above in acidic or basic conditions;

st.B2) reacting the resultant compound of the formula (XV) or the corresponding salt:

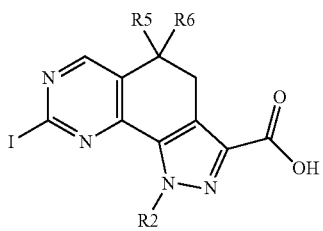

XV wherein R2, R5 and R6 are as defined, with an amine of the formula (XIV) as defined above, in presence of the suitable condensing agents;

st.B3) reacting the resultant compound of the formula (XVI):

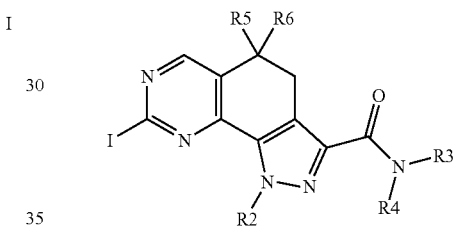

XVI wherein R2, R4, R5 and R6 are as defined above, with an amine of the formula (IX) as defined above, to give a compound of the formula (I):

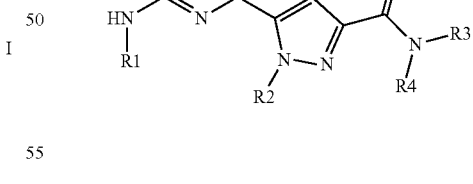

I wherein R1, R2, R3, R4, R5 and R6 are as defined above, and optionally converting a compound of the formula (I) into another different compound of the formula (I), and, if desired, converting a compound of the formula (I) into a pharmaceutically acceptable salt thereof or converting a salt into the free compound (I).

Another process of the present invention comprises:

either st.C1) hydrolysing a compound of the formula (VII) as defined above in acidic or basic conditions and st.C2) reacting the resultant compound of the formula (XVII) or its corresponding salt:

XVII

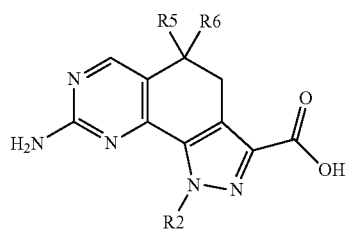

wherein R2, R5 and R6 are as defined above with an amine of the formula (XIV)
as defined above, in presence of the suitable condensing agents;
or st.C1a) reacting a compound of formula (VII) as defined above with an amine of formula (IX) as defined above, in presence of a strong base, to give a compound of formula (XVIII):

XVIII

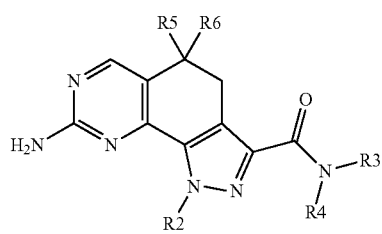

wherein R2, R3, R4, R5 and R6 are as defined above;
st.C3) reacting the compound of the formula (XVIII) as defined above with iso-amylnitrite and diiodomethane or cesium iodide, in the presence of iodine and CuI;
st.C4) converting the resultant compound of the formula (XVI) as defined above into a desired compound of the formula (I) as above defined by operating in as described under st.B3) above.

Another process of the present invention comprises:
st.D1) reacting a compound of (XVIII) as defined above with a compound of the formula (XII):

XII

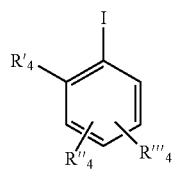

wherein R'4, R''4 and R'''4 are as defined above, to give a compound of the formula (Ia):

Ia

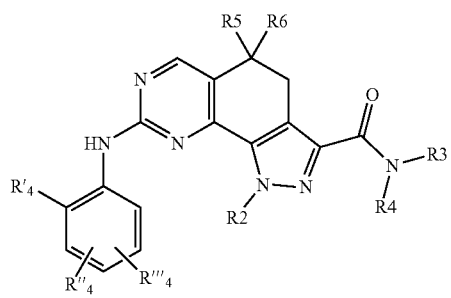

wherein R'4, R''4 and R'''4, R2, R3, R4, R5 and R6 are as defined above, and optionally converting a compound of the formula (Ia) into another different compound of the formula (Ia), and, if desired, converting a compound of the formula (Ia) into a pharmaceutically acceptable salt thereof or converting a salt into the free compound (Ia).

Another process of the present invention comprises:
st.E1) reacting a compound of the formula (XVIII'):

XVIII'

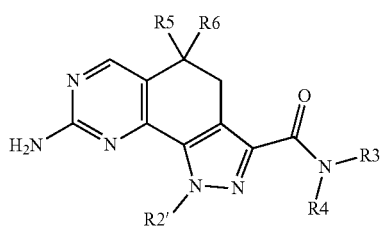

wherein R2' is a trityl group and R3, R4, R5 and R6 are as defined above, under acidic conditions;
st.E2) reacting the resultant compound of the formula (XXI):

XXI

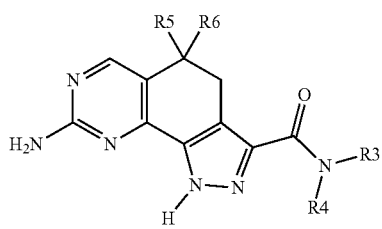

wherein R3, R4, R5 and R6 are as defined above, either with a compound of the formula (V) as defined above or with an alcohol of the formula R2-OH (XXXII) wherein R2 is as defined above but not hydrogen atom, and
st.E3) converting the resultant compound of the formula (XXII):

XXII

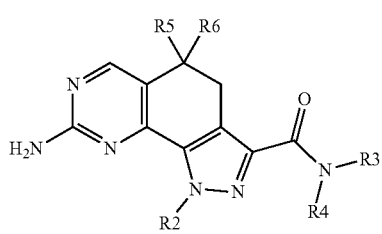

wherein R3, R4, R5 and R6 are as defined above, R2 is as defined above but not hydrogen atom, into a desired compound of the formula (I) as above defined by operating in an analogous way to that described under st.D1), st.C3) and st.C4) above or under st.F1) below.

Another process of the present invention comprises:
st.F1) reacting a compound of the formula (XVIII) as defined above with a compound of the formula (XXIII):

XXIII

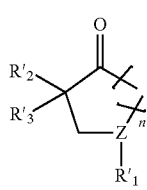

wherein n, Z, R'1, R'2 and R'3 are as defined above, in the presence of sodium triacetoxyborohydride [NaBH(OAc)3)]

and trifluoroacetic acid to give a compound of the formula (Ib) wherein Z, n, R'1, R'2, R'3, R2, R3, R4, R5 and R6 are as defined above, and optionally converting a compound of the formula (Ib) into another different compound of the formula (Ib), and, if desired, converting a compound of the formula (Ib) into a pharmaceutically acceptable salt thereof or converting a salt into the free compound of the formula (Ib).

Another process of the present invention comprises:
st.G1) reacting a compound of the formula (VII) as defined above, with a compound of the formula (XII) as defined above, and converting the resultant compound of the formula (X) wherein R1 is an ortho-substituted-aryl into a desired compound of the formula (Ia) as above defined by operating in an analogous way as described under st.A4) and st.A5) above.

Another process of the present invention comprises:
st.H1) reacting a compound of the formula (VII) as defined above with a compound of the formula (XXIII'):

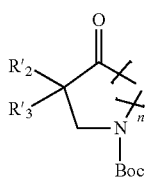

XXIII' wherein n, R'₂, and R'₃ are as defined above, and Boc is terbutoxycarbonyl group under analogous condition described under st.F1) above and
st.H2) reacting if necessary or wanted the resultant compound of the formula (XXV):

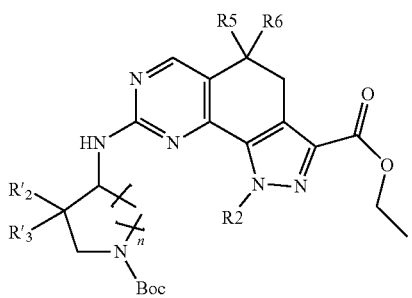

XXV wherein n, R'₂, R'₃, R2, R5, R6 and Boc are as defined, in acidic condition;
st.H3) reacting the resultant compound of the formula (XXVII):

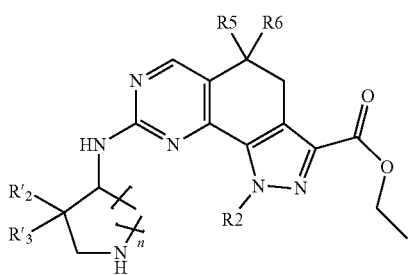

XXVII wherein n, R'₂, R'₃, R2, R5 and R6 are as defined above, with a compound of the formula R'₁Y (XXVI) wherein Y is as defined above and R'₁ is as defined above but not hydrogen atom, and st.H4) converting the resultant compound of the formula (XXVIII):

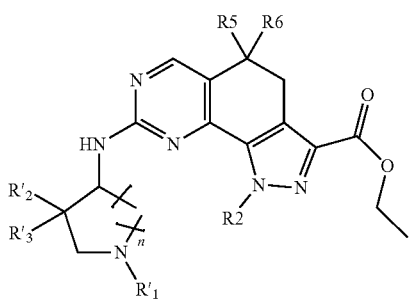

XXVIII wherein n, R'₁, R'₂, R'₃, R2, R5 and R6 are as defined above, into a desired compound of the formula (Ib) as above defined by operating in an analogous way to that described under described under st.A4) and st.A5) above.

Another process of the present invention comprises:
st.I1) reacting a compound of the formula (VIII) as defined above with a compound of the formula (XXXIV):

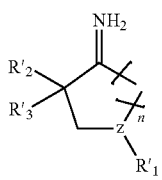

XXXIV wherein n, Z, R'₁, R'₂ and R'₃ are as defined above, and converting the resultant compound of formula (XXVIIIbis):

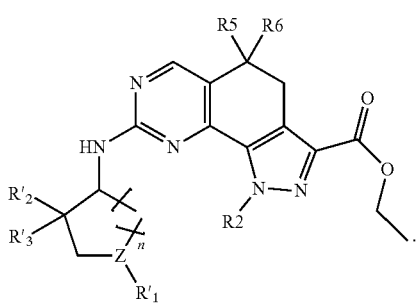

XXVIIIbis wherein n, R'₁, R'₂, R'₃, R2, R5 and R6 are as defined above, into a desired compound of the formula (Ib) as above defined by operating in an analogous way to that described under described under st.A4) and st.A5) above.

As said above, the compounds of the formula (I), (Ia) and (Ib) which are prepared according to the process object of the invention, can be conveniently converted into other compounds of the formula (I), (Ia), or (Ib) by operating according to well-known synthetic conditions, the following being examples of possible conversions.

conv.a) converting a compound of the formula (I) wherein R2 is Trityl and R1, R3, R4, R5 and R6 are as defined above into a compound of the formula (I) wherein R2 is hydrogen atom R1, R3, R4, R5 and R6 are as defined above, under acidic conditions:

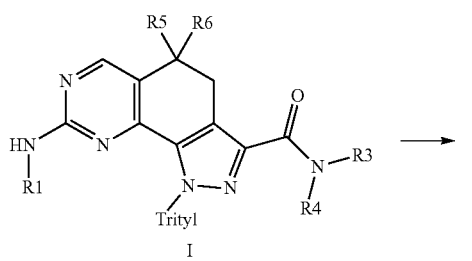

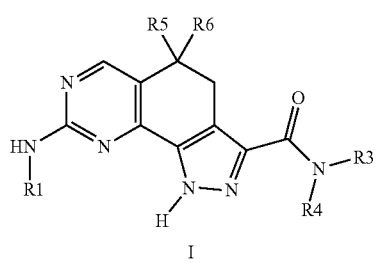

conv.b) converting a compound of the formula (I) wherein R2 is hydrogen atom and R1, R3, R4, R5 and R6 are as defined above into a compound of the formula (I) wherein R2 is as defined above but not hydrogen atom and R1, R3, R4, R and R6 are as defined above, through reaction with compound of the formula (V) as defined above:

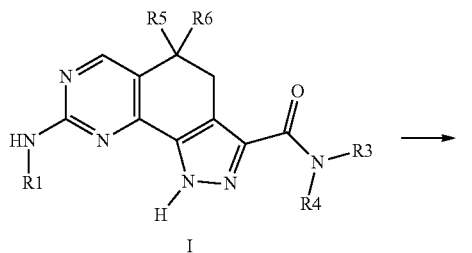

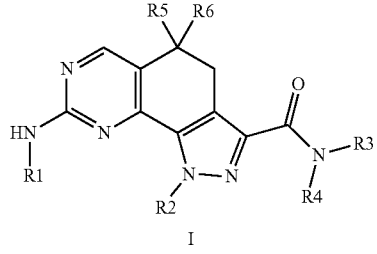

conv.c) converting a compound of the formula (I) wherein R2 is hydrogen atom and R1, R3, R4, R5 and R6 are as defined above into a compound of the formula (I) wherein R2 is as defined above but not hydrogen atom and R1, R3, R4, R and R6 are as defined above, through reaction with an alcohol of the formula R2-OH (XXXII) as defined above:

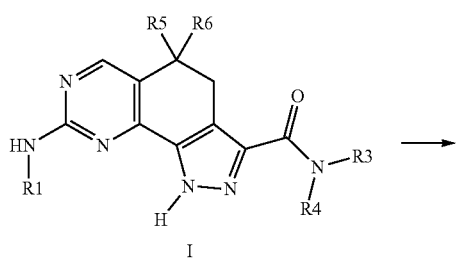

-continued

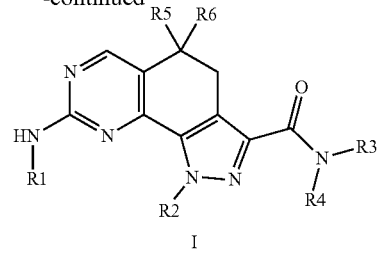

conv.d) converting a compound of the formula (Ia) as defined above wherein $R'_4$, $R''_4$ or $R'''_4$ is Br, and R2, R3, R4, R5 and R6 are as defined above, into a compound of the formula (Ia) wherein $R'_4$, $R''_4$ or $R'''_4$ is a group of the formula —NR7R8 wherein R7 and R8 are each independently hydrogen atom, or an optionally substituted $C_1$-$C_6$ alkyl, polyfluorinated alkyl, alkenyl, alkynyl, hydroxyalkyl, aryl, arylalkyl, heterocyclyl, $C_3$-$C_7$ cycloalkyl, alkylamino, arylamino or heterocyclyamino group, taken together with the nitrogen atom to which they are attached form an optionally substituted heterocyclic ring such as, for example, morpholino, pyrrolidino, pyrrolidin-1-ylmethyl-pyrrolidino, dimethylamino-pyrrolidino, 4-pyrrolidin-piperidino, piperidino, dimethylaminopiperidino, piperazino, N-methylpiperazino, 2-hydroxyethyl-piperazino, or 4-methyl-1,4-diazepano; by treatment with an amine of the formula R7R8-NH (XIV'), wherein R7 and R8 are as defined above.

conv.e) converting a compound of the formula (Ia) as defined above wherein $R'_4$, $R''_4$ or $R'''_4$ is $NO_2$, and R2, R3, R4, R5 and R6 are as defined above, into a compound of the formula (Ia) wherein $R'_4$, $R''_4$ or $R'''_4$ is an amino group by reduction using conventional methods.

conv.f) converting a compound of the formula (Ia) wherein $R'_4$, $R''_4$ or $R'''_4$ is $NH_2$, and R2, R3, R4, R5 and R6 are as defined above into a compound of the formula (Ia) wherein $R'_4$, $R''_4$ or $R'''_4$ is a group —NHCOR9, wherein R9 is an optionally substituted $C_1$-$C_6$ alkyl, polyfluorinated alkyl, alkenyl, alkynyl, aryl, arylalkyl, heterocyclyl, $C_3$-$C_6$ cycloalkyl, alkylamino, arylamino or heterocyclyamino, and R2, R3, R4, R5 and R6 are as defined above, by treatment with a compound of the formula R9-COOH (XX) wherein R9 is as defined above, in the presence of the suitable condensing agents.

conv.g) converting a compound of the formula (Ia) wherein $R'_4$, $R''_4$ or $R'''_4$ is t-butyloxycarbonyl group, and R2, R3, R4, R5 and R6 are as defined above, in acidic condition, into a compound of the formula (Ia) wherein $R'_4$, $R''_4$ or $R'''_4$ is —COOH, and R2, R3, R4, R5 and R6 are as defined above.

conv.h) converting a compound of the formula (Ia) wherein $R'_4$, $R''_4$ or $R'''_4$ is COOH, and R2, R3, R4, R5 and R6 are as defined above into a compound of the formula (Ia) wherein $R'_4$, $R''_4$ or $R'''_4$ is a group —CONR7R8, and R2, R3, R4, R5 and R6 are as defined above by treatment with an amine of the formula (XIV') as defined above in the presence of the suitable condensing agents.

conv.i) converting a compound of the formula (Ia) wherein $R'_4$, $R''_4$ or $R'''_4$ is Br, and R2, R3, R4, R5 and R6 are as defined above into a compound of the formula (Ia) wherein $R'_4$, $R''_4$ or $R'''_4$ is Iodine, and R2, R3, R4, R5 and R6 are as defined above by treatment with CuI, $I_2$ and NaI.

conv.l) converting a compound of the formula (Ia) wherein $R'_4$, $R''_4$ or $R'''_4$ is $CH_2OH$ and R2, R3, R4, R5 and R6 are as defined above into a compound of the formula (Ia) wherein $R'_4$, $R''_4$ or $R'''_4$ is CHO, and R2, R3, R4, R5 and R6 are as defined above by oxidation, for example with $MnO_2$.

conv.m) converting a compound of the formula (Ia) wherein $R'_4$, $R''_4$ or $R'''_4$ is CHO and R2, R3, R4, R5 and R6 are as defined above into a compound of the formula (Ia) wherein R'$_4$, R"$_4$ or R'"$_4$ is CH$_2$NR7R8, and R2, R3, R4, R5, R6, R7 and R8 are as defined above by reductive amination with an amine of formula (XIV') as defined above.

conv.n) converting a compound of the formula (Ia) wherein R'$_4$, R"$_4$ or R'"$_4$ is NH$_2$ and R2, R3, R4, R5 and R6 are as defined above into a compound of the formula (Ia) wherein R'$_4$, R"$_4$ or R'"$_4$ is NR7R8, and R2, R3, R4, R5, R6, R7 and R8 are as defined above by reductive amination with a compound of formula R7COR8 (XXXIII), wherein R7 and R8 are as defined above.

conv.o) converting a compound of the formula (Ib) wherein Z is nitrogen atom, R'$_1$ is t-butyloxycarbonyl group and R'$_2$, R'$_3$, n, R2, R3, R4, R5 and R6 are as defined, in acidic condition, into a compound of the formula (Ib) wherein Z is nitrogen atom, R'$_1$ is hydrogen atom and R'$_2$, R'$_3$, n, R2, R3, R4, R5 and R6 are as defined above.

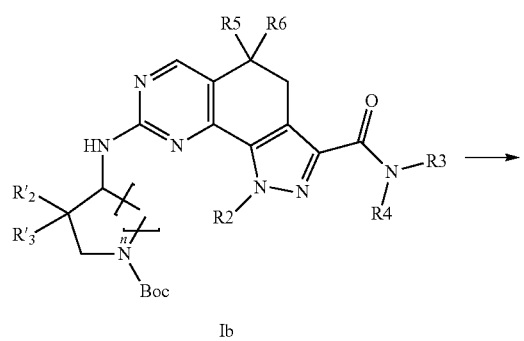

Ib

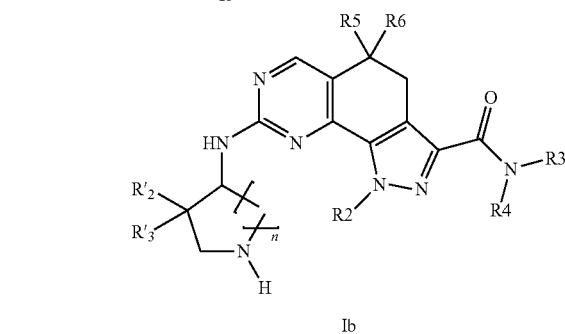

Ib conv.p) converting a compound of the formula (Ib) wherein Z is nitrogen atom, R'$_1$ is hydrogen atom and R'$_2$, R'$_3$, n, R2, R3, R4, R5 and R6 are as defined, by reaction with a compound of the formula (XXVI) as defined above, into a compound of the formula (Ib) wherein and Z is nitrogen atom, R'$_1$, R'$_2$, R'$_3$, n, R2, R3, R4, R5 and R6 are as defined above:

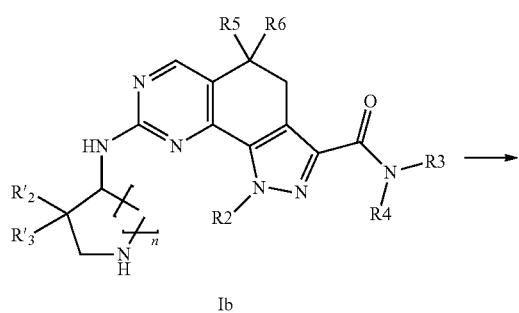

Ib

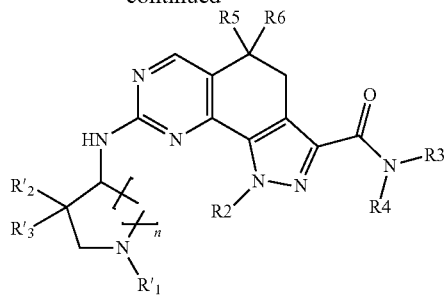

Ib conv.q) converting a compound of the formula (Ib) wherein Z is nitrogen atom, R'1 is hydrogen atom and R'$_2$, R'$_3$, n, R2, R3, R4, R5 and R6 are as defined, by reaction with a compound of the formula (XX) as defined above, into a compound of the formula (Ib) wherein and Z is nitrogen atom, R'$_1$ is —COR9, wherein R9 is as defined above and R'$_2$, R'$_3$, n, R2, R3, R4, R5 and R6 are as defined above:

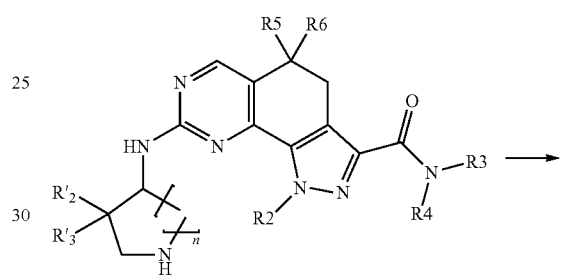

Ib

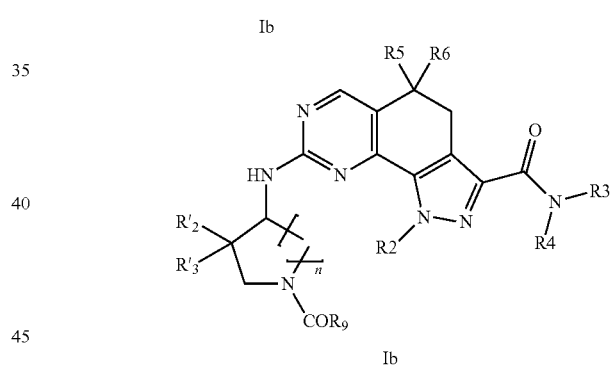

Ib conv.r) converting a compound of the formula (Ib) wherein Z is nitrogen atom, R'$_1$ is hydrogen atom and R'$_2$, R'$_3$, n, R2, R3, R4, R5 and R6 are as defined, by reaction with a compound of the formula R9-SO$_2$Cl (XIX) wherein R9 is as defined above, into a compound of the formula (Ib) wherein and Z is nitrogen atom, R'$_1$ is R9-SO$_2$ and R9, R'$_2$, R'$_3$, n, R2, R3, R4, R5 and R6 are as defined above:

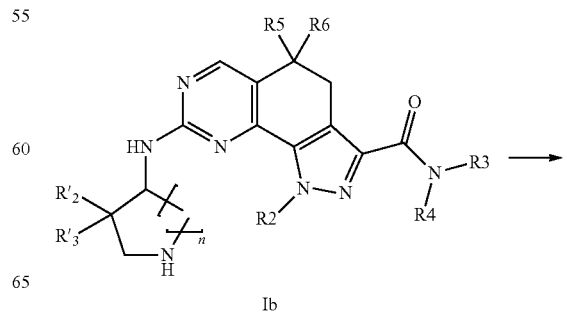

Ib

-continued

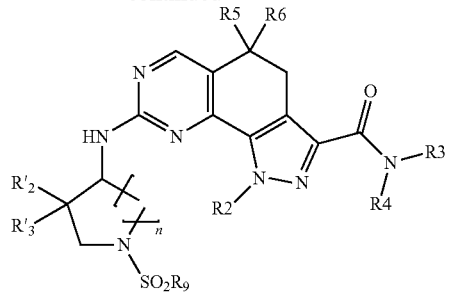
Ib conv.s) converting a compound of the formula (Ib) wherein Z is nitrogen atom, $R'_1$ is hydrogen atom and $R'_2$, $R'_3$, n, R2, R3, R4, R5 and R6 are as defined, by reaction with a compound of the formula $ClCH_2CH_2SO_2Cl$, into a compound of the formula (Ib) wherein and Z is nitrogen atom, $R'_1$ is $-SO_2CH=CH_2$, and $R'_2$, $R'_3$, n, R2, R3, R4, R5 and R6 are as defined above:

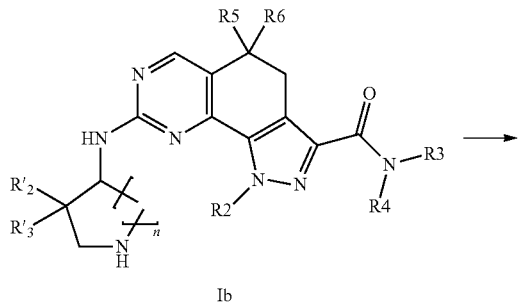
Ib

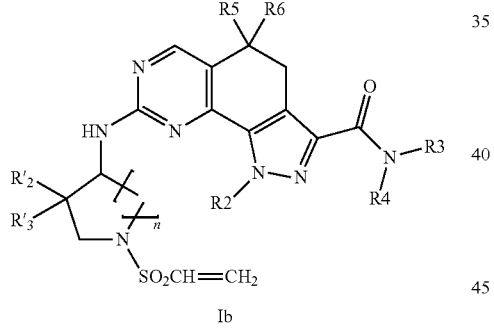
Ib conv.t) converting a compound of the formula (Ib) wherein Z is nitrogen atom, $R'_1$ is hydrogen atom and $R'_2$, $R'_3$, n, R2, R3, R4, R5 and R6 are as defined, by reaction with a compound of the formula $BrCH_2CH_2COCl$, into a compound of the formula (Ib) wherein and Z is nitrogen atom, $R'_1$ is $-COCH=CH_2$, $R'_2$, $R'_3$, n, R2, R3, R4, R5 and R6 are as defined above:

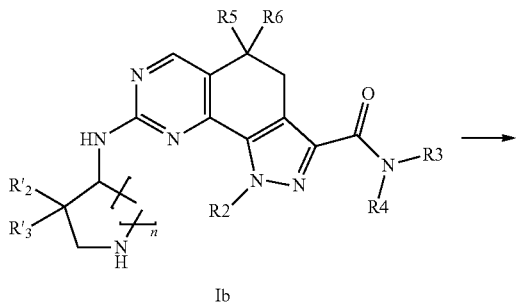
Ib conv.u) converting a compound of the formula (Ib) wherein Z is nitrogen atom, $R'_1$ is $-COCH=CH_2$ and $R'_2$, $R'_3$, n, R2, R3, R4, R5 and R6 are as defined, by reaction with a compound of the formula R7R8NH (XXX) wherein R7 and R8 are as defined above, into a compound of the formula (Ib) wherein and Z is nitrogen atom, $R'_1$ is $-COCH_2CH_2NR7R8$, and R7, R8, $R'_2$, $R'_3$, n, R2, R3, R4, R5 and R6 are as defined above:

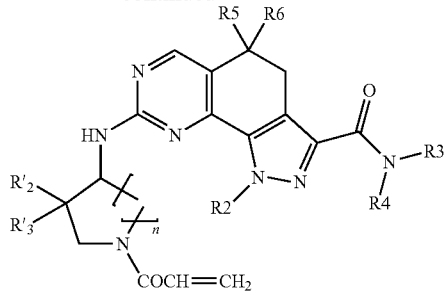
Ib

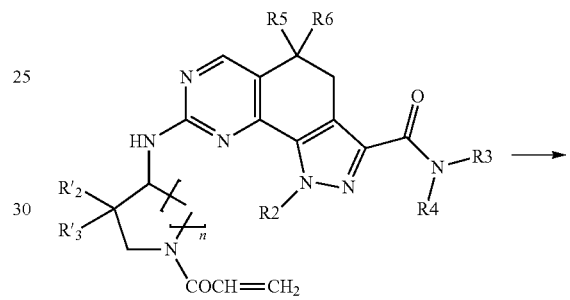
Ib conv.v) converting a compound of the formula (Ib) wherein Z is nitrogen atom, $R'_1$ is $-SO_2CH=CH_2$ and $R'_2$, $R'_3$, n, R2, R3, R4, R5 and R6 are as defined, by reaction with a compound of the formula (XXX) as defined above, into a compound of the formula (Ib) wherein and Z is nitrogen atom, R'1 is $-SO_2CH_2CH_2NR7R8$, $R'_2$, $R'_3$, n, R2, R3, R4, R5 and R6 are as defined above:

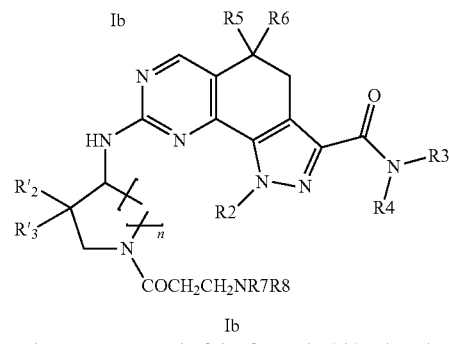
Ib

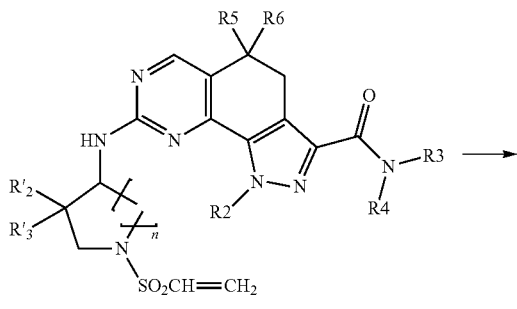
Ib

-continued

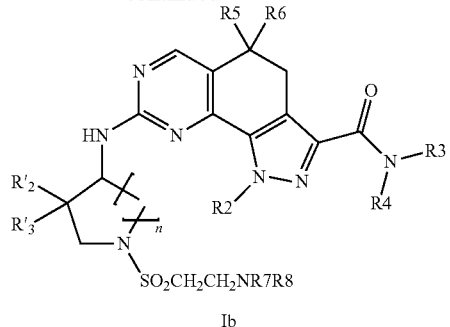

Ib

All the above processes, in any one of the aforementioned variants, are analogy processes which can be carried out according to well known methods and under suitable conditions known in the art.

According to step (st.A1) of the process, a compound of the formula (II) is reacted with the hydrazine derivative of the formula (III) in the presence of acetic acid, so as a compound of the formula (IV) is obtained. The reaction is preferably carried out at room temperature.

If wanted and necessary, the compound of the formula (IV) wherein R2 is hydrogen atom can be converted into a compound of the formula (IV) wherein R2 is as defined above but not hydrogen atom by reaction with a suitable compound of the formula (V) as defined above. When Y is halogen atom, it is preferably chlorine, bromine or iodine, and the reaction is carried out in the presence of a base such as sodium hydride or triethylamine or cesium carbonate, in a suitable solvent, for instance dichloromethane, tetrahydrofuran, dioxane or dimethylformamide, at a temperature ranging from room temperature to 100° C.

According to step (st.A2) of the process, the compound of the formula (IV) is reacted with N,N-dimethylformamide-di-tert-butylacetale or N,N-dimethylformamide-diisopropylacetale, in the presence of a suitable solvent such as, for instance, dimethylformamide, so as to get the compounds of the formula (VI) as defined above. Preferably, the reaction is carried out at a temperature ranging from room temperature to about 80° C.

According to step (st.A3a) of the process, the compound of the formula (VI) as defined above is reacted with guanidine or guanidine salts as to obtain a compound of the formula (VII) as defined above through pyrimidine ring formation.

Compounds of the formula (X) wherein R1 represents an ortho-substituted-aryl group can be obtained by the corresponding iodo-derivatives of the formula (VIII) which, in their turn, is prepared by the corresponding compounds of the formula (VII) as defined above. The preparation of the iodo-derivatives of the formula (VIII) as defined above may be carried out in a suitable solvent such as tetrahydrofuran, diethyl ether or dimethoxyethane, at a temperature ranging from room temperature to about 80° C., and for a time of about 2 to about 48 hours.

The subsequent conversion of the iodo-derivative of the formula (VIII) as defined above into compounds of the formula (X) as defined above may be carried out in the presence of an amine of the formula R1-NH$_2$ (IX) as defined above in a suitable solvent such as dimethylformamide, dimethoxyethane or acetonitrile and in the presence of catalytic amounts of palladium acetate, (2,2'-bis(diphenylphosphino)-1,1'-binaphtalene (BINAP) and a base such as potassium carbonate, potassium phosphate or cesium carbonate, at a temperature ranging from room temperature to 110° C. and for a time ranging from about 2 to about 24 hours.

According to step (st.A3b) of the process, the compound of the formula (VI) as defined above is reacted with a guanidine derivatives of the formula (XI) as defined above so as to obtain the corresponding compound of the formula (X) as defined above through pyrimidine ring formation. Any of the above reactions are carried out according to conventional methods. As an example, the reactions with guanidine or salts thereof such as hydrochloride, carbonate or nitrate, or with the guanidine derivative of the formula (XI) as defined above, as set forth in steps (st.A3a) or (st.A3b), are carried out in dimethylformamide at a temperature ranging from 80° C. to refluxing temperature eventually in the presence of potassium carbonate.

According to step (st.A4) of the process, the compounds of the formula (X) may be converted into carboxylic acid derivatives of the formula (XIII) or corresponding salt through basic or acidic hydrolysis conditions, widely known in the art.

According to step (st.A5) of the process, the compounds of the formula (XIII) as defined above may be converted into carboxamido derivatives of the formula (I) wherein R3 and R4 are as defined above. The reaction is carried out with an amine of the formula (XIV) as defined above, under basic conditions, preferably with N,N-diisopropyl-N-ethylamine or triethylamine, in a suitable solvent such as dichloromethane, dimethylformamide, tetrahydrofuran, or dioxane, and in the presence of a suitable condensing agent such as N,N'-dicyclohexylcarbodiimide (DCC), N-(3-dimethylaminopropyl)-N'-ethylcarbodiimide hydrochloride (EDCI) or O-(benzotriazol-1-yl)-N,N,N',N'-tetramethylisouronium tetrafluoroborate (TBTU); catalytic amounts of (benzotriazol-1-yloxy)tripyrrolidinophosphonium hexafluorophosphate (PyBOP) or N-hydroxybenzotriazole may be also required; at a temperature ranging from room temperature to 80° C. and for a time ranging from about 2 to about 24 hours.

According to step (st.A4a1) of the process, the compound of formula (X) may be converted into carboxamido derivatives of formula (I) wherein R3 and R4 are as defined above. The reaction is carried out with an amine of formula (IX), under basic conditions, preferably with lithium bis(trimethylsilyl)amide or sodium bis(trimethylsilyl)amide, in a suitable solvent such as tetrahydrofuran, or dioxane; at a temperature ranging from 0° C. to 40° C. and for a time ranging from about 1 to about 24 hours.

According to step (st.B1) of the process, the compounds of the formula (VIII) as defined above may be converted into carboxylic acid derivatives of the formula (XV) as defined above or their corresponding salts through basic or acidic hydrolysis conditions, widely known in the art.

According to step (st.B2) of the process, the compounds of the formula (XV) as defined above may be converted into carboxamido derivatives of the formula (XVI) wherein R3 and R4 are as defined above. The reaction is carried out with an amine of the formula (XIV) as defined above, under basic conditions, preferably with N,N-diisopropyl-N-ethylamine or triethylamine, in a suitable solvent such as dichloromethane, dimethylformamide, tetrahydrofuran, or dioxane, and in the presence of a suitable condensing agent such as N,N'-dicyclohexylcarbodiimide (DCC), N-(3-dimethylaminopropyl)-N'-ethylcarbodiimide hydrochloride (EDCI) or O-(benzotriazol-1-yl)-N,N,N',N'-tetramethylisouronium tetrafluoroborate (TBTU); catalytic amounts of (benzotriazol-1-yloxy)tripyrrolidinophosphonium hexafluorophosphate (PyBOP) or N-hydroxybenzotriazole may be also required, at a temperature ranging from room temperature to 80° C. and for a time ranging from about 2 to about 24 hours.

According to step (st.B3) of the process, the compound of the formula (XVI) as defined above is converted into a compound of the formula (I) wherein R1, R2, R3, R4a, R5 and R6 are as defined above, by reaction with an amine of the formula (IX) as defined above. The reaction is carried out in presence of the amine of the formula (IX) as defined above in a suitable solvent such as dimethylformamide, dimethoxyethane or acetonitrile, and in the presence of catalytic amounts of palladium acetate, (2,2'-bis(diphenylphosphino)-1,1'-binaphtalene (BINAP) and a base such as potassium carbonate, potassium phosphate or cesium carbonate, at a temperature ranging from room temperature to 110° C. and for a time ranging from about 2 to about 24 hours.

According to step (st.C1) of the process, the compounds of the formula (VII) as defined above may be converted into carboxylic acid derivatives of the formula (XVII) as defined above or their corresponding salts through basic or acidic hydrolysis conditions, widely known in the art.

According to step (st.C2) of the process, the compounds of the formula (XVII) as defined above may be converted into carboxamido derivatives of the formula (XVIII) wherein R3 and R4 are as defined above. The reaction is carried out in presence of an amine of the formula (XIV) as defined above, under basic conditions, preferably with N,N-diisopropyl-N-ethylamine or triethylamine, in a suitable solvent such as dichloromethane, dimethylformamide, tetrahydrofuran, or dioxane, and in the presence of a suitable condensing agent such as N,N'-dicyclohexylcarbodiimide (DCC), N-(3-dimethylaminopropyl)-N'-ethylcarbodiimide hydrochloride (EDCI) or 0-(benzotriazol-1-yl)-N,N,N',N'-tetramethylisouronium tetrafluoroborate (TBTU); catalytic amounts of (benzotriazol-1-yloxy)tripyrrolidinophosphonium hexafluorophosphate (PyBOP) or N-hydroxybenzotriazole may be also required.

According to step (st.C1a) of the process, the compound of formula (VII) may be converted into carboxamido derivatives of formula (XVIII) wherein R3 and R4 are as defined above. The reaction is carried out with an amine of formula (IX), under basic conditions, preferably with lithium bis(trimethylsilyl)amide or sodium bis(trimethylsilyl)amide, in a suitable solvent such as tetrahydrofuran, or dioxane; at a temperature ranging from 0° C. to 40° C. and for a time ranging from about 1 to about 24 hours.

According to step (st.C3) of the process compounds of the formula (XVIII) as defined above may be converted into derivatives of the formula (XVI) wherein R2, R3, R4, R5 and R6 are as defined above. The reaction is carried out in a suitable solvent such as dimethoxyethane, tetrahydrofuran or diethyl ether in presence of cesium iodide, iodine, copper iodide and isopentyl nitrite at a temperature ranging from 50 to 80° C. and for a time ranging from about 2 to about 24 hours.

According to step (st.D1) of the process, the compounds of the formula (XVIII) as defined above are reacted with compounds of the formula (XII) as defined above, according to conventional methods. As an example the reaction can be carried out in a suitable solvent such as dimethylformamide, dimethoxyethane or acetonitrile and in the presence of an ortho-substituted-aryliodine of the formula (XII), catalytic amounts of palladium acetate or tris(dibenzylideneacetone) dipalladium (Pd$_2$(dba)$_3$), (2,2'-bis(diphenylphosphino)-1,1'-binaphtalene (BINAP) or 2-(dicyclohexylphosphino)-2',4',6'-triisopropyl-1,1-biphenyl (X-phos) and a base such as potassium carbonate, potassium phosphate or cesium carbonate, at a temperature ranging from room temperature to 110° C. and for a time ranging from about 2 to about 24 hours.

According to step (st.E1) of the process, the compounds of the formula (XVIII') as defined above are reacted in acidic conditions, for instance with trifluoroacetic acid and in the presence of a suitable solvent such as dichloromethane, to give a compound of the formula (XXI) as defined above at a temperature ranging from room temperature to 50° C. and for a time ranging from about 1 to about 12 hours.

According to step (st.E2) of the process, the compound of the formula (XXI) as defined above is reacted
either with a suitable compound of the formula (V) as defined above, in the presence of a base such as sodium hydride or triethylamine or cesium carbonate, in a suitable solvent, for instance dichloromethane, tetrahydrofuran, dioxane or dimethylformamide, at a temperature ranging from room temperature to 100° C., and for a time ranging from about 1 to about 12 hours;
or with an alcohol of the formula (XXXI) as defined above, in the presence of di-t-butylazadicarboxylate and triphenylphosphine or triphenylphosphine supported on resin, in a suitable solvent such as, for instance, tetrahydrofurane, at a temperature ranging from room temperature to 60° C. and for a time ranging from about 1 to about 12 hours, so as to obtain a compound of the formula (XXII) as defined above.

According to (st.F1) of the process, a compound of the formula (XVIII) is reacted with a compound of the formula (XXIII) as defined above, in the presence of sodium triacetoxyborohydride (NaBH(OAc)$_3$) and trifluoroacetic acid in the presence of di-t-butylazadicarboxylate and triphenylphosphine or triphenylphosphine supported on resin, in a suitable solvent such as, for instance, tetrahydrofurane, at a temperature ranging from room temperature to 60° C. and for a time ranging from about 1 to about 12 hours to give a compound of the formula (Ib).

According to step (st.G1) of the process, a compound of the formula (VII) as defined above is reacted with compounds of the formula (XII) wherein R1 represents an ortho-substituted-aryliodide according to conventional methods. As an example the reaction can be carried out in a suitable solvent such as dimethylformamide, dimethoxyethane or acetonitrile and in the presence of an ortho-substituted-aryliodine of the formula (XII), catalytic amounts of palladium acetate, (2,2'-bis(diphenylphosphino)-1,1'-binaphtalene (BINAP) and a base such as potassium carbonate, potassium phosphate or cesium carbonate, at a temperature ranging from room temperature to 110° C. and for a time ranging from about 2 to about 24 hours.

According to (st.H1) of the process, a compound of the formula (VII) is reacted with a compound of the formula (XXIII') as defined above, in the presence of sodium triacetoxyborohydride (NaBH(OAc)$_3$) and trifluoroacetic acid in the presence of di-t-butylazadicarboxylate and triphenylphosphine or triphenylphosphine supported on resin, in a suitable solvent such as, for instance, tetrahydrofurane, at a temperature ranging from room temperature to 60° C. and for a time ranging from about 1 to about 12 hours to give a compound of the formula (XXV) as defined above.

According to (st.H2) of the process, a compound of the formula (XXV) as defined above is reacted in acidic conditions, for example with hydrochloric or trifluoric acid in a suitable solvent, for instance tetrahydrofurane or dioxane, at a temperature of from room temperature to 60° C. and for a period of from about 1 to about 12 hours, to give a compound of the formula (XXVII) as defined above.

According to step (st.H3) of the process, a compound of the formula (XXVII) as defined above is reacted with a suitable compound of the formula (XXVI) as defined above wherein when Y is a halogen atom, it is preferably chlorine, bromine or iodine, in the presence of a base such as sodium hydride or triethylamine or cesium carbonate, in a suitable solvent, for instance dichloromethane, tetrahydrofuran, dioxane or dimethylformamide, at a temperature ranging from room temperature to 100° C., and for a time ranging from about 1 to about 12 hours as to obtain compound (XXVIII) as defined above.

According to (st.I1) of the process, a compound of the formula (VIII) is reacted with a compound of the formula (XXXIV) as defined above, in a suitable solvent such as, for instance, tetrahydrofurane or acetonitrile, at reflux temperature and for a time ranging from about 30 minutes to about 12 hours to give a compound of the formula (XXVIII) as defined above.

According to conversion (con.a) of the process, a compound of the formula (I) wherein R2 is trytil may be converted into another compound of the formula (I) wherein R2 is hydrogen atom by reaction in acidic conditions, for instance with trifluoroacetic acid or hydrochloric acid and in the presence of a suitable solvent such as dichloromethane or dioxane, at a temperature ranging from room temperature to 50° C. and for a time ranging from about 1 to about 12 hours.

According to conversion (con.b) of the process, a compound of the formula (I) wherein R2 is hydrogen atom may be converted into another compound of the formula (I) wherein R2 is as defined above except hydrogen atom, by reaction with a suitable compound of the formula (V) as defined above and when Y is halogen atom, it is preferably chlorine, bromine or iodine, in the presence of a base such as sodium hydride or triethylamine or cesium carbonate, in a suitable solvent, for instance dichloromethane, tetrahydrofuran, dioxane or dimethylformamide, at a temperature ranging from room temperature to 100° C., so and for a time ranging from about 1 to about 12 hours.

According to conversion (con.c) of the process, a compound of the formula (I) wherein R2 is hydrogen atom may be converted into another compound of the formula (I) wherein R2 is as defined above except hydrogen atom, by reaction with an alcohol of the formula (XXXII) as defined above, in the presence of di-t-butylazadicarboxylate and triphenylphosphine or triphenylphosphine supported on resin, in a suitable solvent such as, for instance, tetrahydrofurane, at a temperature ranging from room temperature to 60° C. and for a time ranging from about 1 to about 12 hours.

According to conversion (con.d) of the process, a compound of the formula (Ia) wherein $R'_4$, $R''_4$ or $R'''_4$ is bromine, may be converted into another compound of the formula (Ia) wherein $R'_4$, $R''_4$ or $R'''_4$ is —NR7R8, wherein R7 and R8 are as defined above, by treatment with an amine of the formula (XIV') as defined above, in a suitable solvent such as tetrahydrofurane or dioxane, and in the presence of catalytic amounts of tris(dibenzilideneacetone)dipalladium, 2-dicyclohexylphosphino-2'-(N,N-dimethylamino)-biphenyl and a base such as $LiN(TMS)_2$ at a temperature ranging from room temperature to reflux and for a time ranging from 1 to about 24 hours.

According to conversion (con.e) of the process, a compound of the formula (Ia) wherein $R'_4$, $R''_4$ or $R'''_4$ is $NO_2$, may be converted into another compound of the formula (Ia) wherein $R'_4$, $R''_4$ or $R'''_4$ is —$NH_2$, into a variety of ways, according to conventional methods for reducing a nitro to an amino group. Preferably, this reaction is carried out in a suitable solvent such as, for instance, methanol, ethanol, water, tetrahydrofuran, 1,4-dioxane, N,N-dimethylformamide, acetic acid, or a mixture thereof, in the presence of a suitable reducing agent, such as, for instance, hydrogen and a hydrogenation catalyst, or by treatment with cyclohexene or cyclohexadiene, or formic acid or ammonium formate and a hydrogenation catalyst, or a metal such as iron or zinc in the presence of an inorganic acid, such as hydrochloric acid, or by treatment with tin (II) chloride, at a temperature ranging from 0° C. to reflux and for a time varying from about 1 hour to about 96 hours. The hydrogenation catalyst is usually a metal, most often palladium, which can be used as such or supported on carbon.

According to conversion (con.f) of the process, a compound of the formula (Ia) wherein $R'_4$, $R''_4$ or $R'''_4$ is —$NH_2$, may be converted into another compound of the formula (Ia) wherein $R'_4$, $R''_4$ or $R'''_4$ is —NHCOR9, by reaction with an acid of the formula (XX) as defined above, under basic conditions, preferably with N,N-diisopropyl-N-ethylamine or triethylamine, in a suitable solvent such as dichloromethane, dimethylformamide, tetrahydrofuran, or dioxane, and in the presence of a suitable condensing agent such as N,N'-dicyclohexylcarbodiimide (DCC), N-(3-dimethylaminopropyl)-N'-ethylcarbodiimide hydrochloride (EDCI) or O-(benzotriazol-1-yl)-N,N,N',N'-tetramethylisouronium tetrafluoroborate (TBTU); catalytic amounts of (benzotriazol-1-yloxy)tripyrrolidinophosphonium hexafluorophosphate (PyBOP) or N-hydroxybenzotriazole may be also required, at a temperature ranging from room temperature to 60° C. and for a time ranging from about 1 to about 24 hours.

According to conversion (con.g) of the process, a compound of the formula (Ia) wherein $R'_4$, $R''_4$ or $R'''_4$ is t-butyloxycarbonyl group, may be converted into another compound of the formula (Ia) wherein $R'_4$, $R''_4$ or $R'''_4$ is —COOH by reaction in acidic condition for example with hydrochloric acid or trifluoric acid in a suitable solvent, for instance, tetrahydrofurane or dioxane, at a temperature ranging from room temperature to 60° C. and for a time ranging from about 1 to about 12 hours.

According to conversion (con.h) of the process, a compound of the formula (Ia) wherein $R'_4$, $R''_4$ or $R'''_4$ is —COOH, may be converted into another compound of the formula (Ia) wherein $R'_4$, $R''_4$ or $R'''_4$ is —CONR7R8, wherein R7 and R8 are as defined above, by reaction with an amine of the formula (XIV') as defined above, under basic conditions, preferably with N,N-diisopropyl-N-ethylamine or triethylamine, in a suitable solvent such as dichloromethane, dimethylformamide, tetrahydrofuran, or dioxane, and in the presence of a suitable condensing agent such as N,N'-dicyclohexylcarbodiimide (DCC), N-(3-dimethylaminopropyl)-N'-ethylcarbodiimide hydrochloride (EDCI) or O-(benzotriazol-1-yl)-N,N,N',N'-tetramethylisouronium tetrafluoroborate (TBTU); catalytic amounts of (benzotriazol-1-yloxy)tripyrrolidinophosphonium hexafluorophosphate (PyBOP) or N-hydroxybenzotriazole may be also required, at a temperature ranging from room temperature to 60° C. and for a time ranging from about 1 to about 24 hours.

According to conversion (con.i) of the process, a compound of the formula (Ia) wherein $R'_4$, $R''_4$ or $R'''_4$ is —Br, may be converted into another compound of the formula (Ia) wherein $R'_4$, $R''_4$ or $R'''_4$ is —I, the reaction being be carried out in a suitable solvent such as tetrahydrofuran, diethyl ether dioxane or dimethoxyethane, using as iodine source for example NaI, CuI and $I_2$, at a temperature ranging from room temperature to about 180° C., and for a time of about 2 to about 48 hours.

According to (con.l) of the process a compound of the formula (Ia) wherein $R'_4$, $R''_4$ or $R'''_4$ is $CH_2OH$ may be converted into another compound of the formula (Ia) wherein $R'_4$, $R''_4$ or $R'''_4$ is —CHO, into a variety of ways, according to conventional methods for oxiding a benzylic ancohol into an aldehydro group. Preferably, this reaction is carried out in a suitable solvent such as, for instance, dichlorometnae or chloroform, in the presence of a suitable oxidizing agent, such as, for instance, $MnO_2$, at a temperature ranging from 0° C. to reflux and for a time varying from about 1 hour to about 96 hours.

According to (con.m) of the process a compound of the formula (Ia) wherein $R'_4$, $R''_4$ or $R'''_4$ is CHO may be converted into another compound of the formula (Ia) wherein $R'_4$, $R''_4$ or $R'''_4$ is—is $CH_2NR7R8$, into a variety of ways, according to conventional methods for reductive amination. Preferably, this reaction is carried out in a suitable solvent such as, for instance, methanol, ethanol, dichloromethane, tetrahydrofuran, 1,4-dioxane, acetic acid, or a mixture thereof, in the presence of reductive agent such as for example $NaBH(AcO)_3$ and a suitable amine, R7R8-NH (XIV'), at a temperature ranging from 0° C. to reflux and for a time varying from about 1 hour to about 96 hours.

According to (con.n) of the process a compound of the formula (Ia) wherein $R'_4$, $R''_4$ or $R'''_4$ is $NH_2$ may be converted into another compound of the formula (Ia) wherein $R'_4$, $R''_4$ or $R'''_4$ is—is NR7R8, into a variety of ways, according to conventional methods for reductive amination. Preferably, this reaction is carried out in a suitable solvent such as, for instance, methanol, ethanol, dichloromethane, tetrahydrofuran, 1,4-dioxane, acetic acid, or a mixture thereof, in the presence of reductive agent such as for example $NaBH(AcO)_3$ and a suitable ketone, such as, for instance, R7COR8 (XXXIII), at a temperature ranging from 0° C. to reflux and for a time varying from about 1 hour to about 96 hours.

According to conversion (con.o) of the process, a compound of the formula (Ib) wherein Z is nitrogen atom and $R'_1$ is t-butyloxycarbonyl group may be converted into another compound of the formula (Ib) wherein Z is nitrogen atom and $R'_1$ is hydrogen atom by reaction in acidic condition for example with hydrochloric acid or trifluoric acid in a suitable solvent, for instance, tetrahydrofurane or dioxane, at a temperature ranging from room temperature to 60° C. and for a time ranging from about 1 to about 12 hours.

According to conversion (con.p) of the process, a compound of the formula (Ib) wherein Z is nitrogen atom and $R'_1$ is hydrogen atom, may be converted into another compound of the formula (Ib) wherein Z is nitrogen atom and $R'_1$ is as defined above except hydrogen atom by reaction with a suitable compound of the formula $R'_1$—Y (XXXI) wherein $R'_1$ is as defined above but not hydrogen atom and Y is halogen atom preferably chlorine, bromine or iodine in the presence of a base such as sodium hydride or triethylamine or cesium carbonate, in a suitable solvent, for instance dichloromethane, tetrahydrofuran, dioxane or dimethylformamide, at a temperature ranging from room temperature to 100° C., so and for a time ranging from about 1 to about 12 hours.

According to conversion (con.q) of the process, a compound of the formula (Ib) wherein Z is nitrogen atom and $R'_1$ is hydrogen atom may be converted into another compound of the formula (Ib) wherein Z is nitrogen atom and $R'_1$ is —NHCOR9 wherein R9 is as defined above by reaction with an acid of the formula (XX) as defined above, under basic conditions, preferably with N,N-diisopropyl-N-ethylamine or triethylamine, in a suitable solvent such as dichloromethane, dimethylformamide, tetrahydrofuran, or dioxane, and in the presence of a suitable condensing agent such as N,N'-dicyclohexylcarbodiimide (DCC), N-(3-dimethylaminopropyl)-N'-ethylcarbodiimide hydrochloride (EDCI) or O-(benzotriazol-1-yl)-N,N,N',N'-tetramethylisouronium tetrafluoroborate (TBTU); catalytic amounts of (benzotriazol-1-yloxy)tripyrrolidinophosphonium hexafluorophosphate (PyBOP) or N-hydroxybenzotriazole may be also required, at a temperature ranging from room temperature to 60° C. and for a time ranging from about 1 to about 24 hours.

According to conversion (con.r) of the process, a compound of the formula (Ib) wherein Z is nitrogen atom and $R'_1$ is hydrogen atom, may be converted into another compound of the formula (Ib) wherein Z is nitrogen atom and $R'_1$ is $SO_2R9$, wherein R9 is as defined above by reaction with an acid of the formula (XIX) as defined above, under basic conditions, preferably with N,N-diisopropyl-N-ethylamine or triethylamine, in a suitable solvent such as dichloromethane, dimethylformamide, tetrahydrofuran, or dioxane, at a temperature ranging from room temperature to 60° C. and for a time ranging from about 1 to about 24 hours.

According to conversion (con.s) of the process, a compound of the formula (Ib) wherein Z is nitrogen atom and $R'_1$ is hydrogen atom, may be converted into another compound of the formula (Ib) wherein Z is nitrogen atom and $R'_1$ is —$SO_2$—CH=$CH_2$ by reaction with a compound of the formula $ClCH_2CH_2SO_2Cl$, under basic conditions, preferably with N,N-diisopropyl-N-ethylamine or triethylamine, in a suitable solvent such as dichloromethane, dimethylformamide, tetrahydrofuran, or dioxane, at a temperature ranging from room temperature to 60° C. and for a time ranging from about 1 to about 24 hours.

According to conversion (con.t) of the process, a compound of the formula (Ib) wherein Z is nitrogen atom and $R'_1$ is hydrogen atom, may be converted into another compound of the formula (Ib) wherein Z is nitrogen atom and $R'_1$ is —CO—CH=$CH_2$, by reaction with an compound of the formula $BrCH_2CH_2COCl$, under basic conditions, preferably with N,N-diisopropyl-N-ethylamine or triethylamine, in a suitable solvent such as dichloromethane, dimethylformamide, tetrahydrofuran, or dioxane, in the presence of a suitable condensing agent such as N,N'-dicyclohexylcarbodiimide (DCC), N-(3-dimethylaminopropyl)-N'-ethylcarbodiimide hydrochloride (EDCI) or O-(benzotriazol-1-yl)-N,N,N',N'-tetramethylisouronium tetrafluoroborate (TBTU); catalytic amounts of (benzotriazol-1-yloxy)tripyrrolidinophosphonium hexafluorophosphate (PyBOP) or N-hydroxybenzotriazole may be also required at a temperature ranging from room temperature to 60° C. and for a time ranging from about 1 to about 24 hours.

According to conversion (con.u) of the process, a compound of the formula (Ib) wherein Z is nitrogen atom and $R'_1$ is —COCH=$CH_2$, may be converted into another compound of the formula (Ib) wherein Z is nitrogen atom and $R'_1$ is —$COCH_2CH_2NR7R8$, wherein R7 and R8 are as above defined by reaction with an amine of the formula (XXX) as defined above, in a suitable solvent such as dichloromethane, dimethylformamide, tetrahydrofuran, or dioxane, at a temperature ranging from room temperature to 60° C. and for a time ranging from about 1 to about 24 hours.

According to conversion (con.v) of the process, a compound of the formula (Ib) wherein Z is nitrogen atom and $R'_1$ is $SO_2CHCH_2$, may be converted into another compound of the formula (Ib) wherein Z is nitrogen atom and $R'_1$ is —$SO_2CH_2CH_2NR7R8$, wherein R7 and R8 are as defined above, by reaction with an amine of the formula (XXX) as defined above, in a suitable solvent such as dichloromethane, dimethylformamide, tetrahydrofuran, or dioxane, at a temperature ranging from room temperature to 60° C. and for a time ranging from about 1 to about 24 hours. Needless to say, also any of the intermediates of the above described processes could be converted into a different intermediate, if wanted and necessary, by operating in an analogous way as in any one of the conversion reaction here above described.

From all of the above it is clear to the skilled person that any compound of the formula (I) bearing a functional group which can be further derivatized to another functional group, by working according to methods well known in the art thus leading to other compounds of the formula (I), is intended to be comprised within the scope of the present invention.

According to any variant of the process for preparing the compounds of the formula (I), the starting materials and any other reactants are known or easily prepared according to known methods. As an example, whilst the starting material of the compounds of the formula (II) is commercially available, the compounds of the formula (II) can be prepared as described in the aforementioned WO 04/104007. Compounds of the formula (III), (V), (IX), (XI), (XIV), (XIV'), (XIX), (XX), (XXIII), (XXVI), (XXIX), (XXX), (XXXI) and (XXXIII) are commercially available, others can be prepared, see following examples.

From all of the above, it is clear to the skilled person that when preparing the compounds of the formula (I) according to any one of the aforementioned process variants, optional functional groups within the starting materials or the intermediates thereof that could give rise to unwanted side reactions, need to be properly protected according to conventional techniques. Likewise, the conversion of these latter into the free deprotected compounds may be carried out according to known procedures.

As it will be readily appreciated, if the compounds of the formula (I) prepared according to the process described above are obtained as mixture of isomers, their separation using conventional techniques into the single isomers of the formula (I), is within the scope of the present invention.

Conventional techniques for racemate resolution include, for instance, partitioned crystallization of diastereoisomeric salt derivatives or preparative chiral HPLC.

In addition, the compounds of the formula (I) of the invention may be also prepared according to combinatorial chemistry techniques widely known in the art, for instance by accomplishing the aforementioned reactions between the several intermediates in a parallel and/or serial manner and by working under solid-phase-synthesis (SPS) conditions.

Pharmacology

The compounds of the formula (I) are active as protein kinase inhibitors and are therefore useful, for instance, to restrict the unregulated proliferation of tumor cells.

In therapy, they may be used in the treatment of various tumors, such as those formerly defined, as well as in the treatment of other cell proliferative disorders such as benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

The inhibiting activity of putative MPS1 inhibitors and the potency of selected compounds was determined through the assays below described.

The short forms and abbreviations used herein have the following meaning:
Ci Curie
DMSO dimethylsulfoxide
KDa kiloDalton
microCi microCurie
Et ethyl
Cloning, Expression and Purification of Recombinant MPS1 Full Length Protein.

MPS1 full length (corresponding to residues 2-857 of the full length sequence, see Swiss-Prot accession number P33981) was PCR amplified from the full-length human MPS1 gene present in house as clone pGEX4t_MPS1.

Amplification was performed using the forward oligonucleotide: 5' ggggacaagtttgtacaaaaaagcaggcttactggaagttctgttccaggggcccgaatccgaggatttaagtggcagag3' [SEQ ID NO: 1] and the reverse oligonucleotide: 5' ggggaccactttgtacaagaaagctgggttt-tatttttttcccctttttttttcaaaagtcttggaggatgaag3' [SEQ ID NO: 2].

For cloning purposes, the oligonucleotides included attB sites in order to obtain an attB-flanked PCR product suitable for cloning using the Gateway® technology (Invitrogen). Furthermore, for purification purposes, forward primer included a protease cleavage site. The resulting PCR product was cloned in the pDONR201 plasmid and then transferred in the baculovirus expression vector pVL1393GST (Invitrogen) Gateway®-modified. Cloning was performed according to the protocols described in the Gateway® manual.

Baculoviruses were generated by cotransfecting Sf9 insect cells with the expression vector and the viral DNA using the BaculoGold® transfection kit (Pharmingen). Viral supernatant was recovered after 5 days and subjected to 3 rounds of amplification to increase viral titer. Recombinant protein was produced by infecting High5 insect cells. After 72 hours of infection at 21° C., cells were recovered, pelletted and freezed at −80° C. For purification of recombinant protein, pellet was thawed, resuspended in lysis buffer (PBS, NaCl 150 mM, Glycerol 10%, CHAPS 0.1%, DTT 20 mM, protease and phosphatase inhibitors) and lysed by Gaulin. Lysate was cleared by centrifugation and loaded on a GST affinity column. After extensive wash, recombinant protein was cleaved by a specific protease and eluted by incubation.

To get a fully activated enzyme, the protein was then subjected to auto-phosphorylation in presence of ATP 1 mM at 25° C. for 2 hours in kinase buffer (Hepes pH7.5 50 mM, MgCl2 2.5 mM, MnCl2 1 mM, DTT 1 mM, phosphatase inhibitors); ATP was then removed whit a desalting column.

Biochemical Assay for Inhibitors of MPS1 Kinase Activity

The inhibitory activity of putative kinase inhibitors and the potency of selected compounds were determined using a trans-phosphorylation assay.

Specific peptide or protein substrates are trans-phosphorylated by their specific ser-thr or tyr kinase in the presence of ATP traced with $^{33}P$-γ-ATP, and in the presence of their own optimal buffer and cofactors.

At the end of the phosphorylation reaction, more than 98% unlabeled ATP and radioactive ATP is captured by an excess of the ion exchange dowex resin; the resin then settles down to the bottom of the reaction plate by gravity. Supernatant is subsequently withdrawn and transferred into a counting plate, then evaluated by β-counting.

Reagents/Assay Conditions i. Dowex Resin Preparation 500 g of wet resin (SIGMA, custom prepared resin DOWEX 1×8 200-400 mesh, 2.5 Kg) are weighed out and diluted to 2 l in 150 mM sodium formate, pH 3.00.

The resin is allowed to settle down (some hours) and then the supernatant is discarded.

After three washes as above over a couple of days, the resin is allowed to settle and two volumes (wrt the resin volume) of 150 mM sodium formate buffer are added.

The pH is then measured and should be around 3.00

The washed resin is stable for more than one week; the stock resin is kept at 4° C. before use.

ii. Kinase Buffer (KB)

The buffer for MPS1 assay was composed of HEPES 50 mM, at pH 7.5, with 2.5 mM MgCl$_2$, 1 mM MnCl$_2$, 1 mM DTT, 3 microM NaVO$_3$, 2 mM □-glycerophosphate and 0.2 mg/mL BSA iii. Assay Conditions The assay was run with a final concentration MPS1 of 5 nM, in the presence of 15 microM ATP and 1.5 nM $^{33}$P-□-ATP; the substrate was P38-□tide, used at 200 microM.

Robotized Dowex Assay

The test mix consisted of:
1) 3× Enzyme mix (done in Kinase Buffer 3×), 5 microL/well
2) 3× substrate and ATP mix (done in ddH2O), together with $^{33}$P-γ-ATP, 5 microL/well
3) 3× test compounds (diluted into ddH2O—3% DMSO)—5 microL/well See below for compound dilution and assay scheme.

Compound Dilution and Assay Scheme is Defined Below:

i. Dilution of Compounds

Test compounds are received as a 1 mM solution in 100% DMSO, distributed into 96 or 384 well plates:
a) for percent inhibition studies (HTS), individual dilution plates at 1 mM are diluted at a 3× concentration (30 microM) in ddH$_2$O (3% DMSO=final concentration) using a Beckman NX automated pipetting platform. The same instrument is used for distributing the diluted mother plates into the test plates.
b) for IC$_{50}$ determination (KSS platform), 100 □l of each compound at 1 mM in 100% DMSO are transferred from the original plate into the first column of another 96 well plate (A1 to G1); well H1 is left empty for the internal standard inhibitor, usually staurosporine.

An automated station for serial dilutions (Biomek FX, Beckman) is used for producing 1:3 dilutions in 100% DMSO, from line A1 to A10, and for all the seven compounds in the column. Moreover, 4-5 copies of daughter plates are prepared by reformatting 5 microL of this first set of 100% DMSO dilution plates into 384 deep well-plates: one copy of the daughter plates with the serial dilutions of test compounds will be thaw the day of the experiments, reconstituted at a 3× concentration with water and used in the IC$_{50}$ determination assays. In a standard experiment, the highest concentration (3×) of all compounds is 30 microM, while the lowest one is 1.5 nM.

Each 384 well-plate will contain reference wells (total enzyme activity vs. no enzymatic activity) for the Z' and signal to background evaluation.

ii. Assay Scheme 384-well plates, V bottom (test plates) are prepared with 5 microL of the compound dilution (3×) and then placed onto a PlateTrak 12 robotized station (Perkin Elmer; the robot has one 384-tips pipetting head for starting the assay plus one 96-tips head for dispensing the resin) together with one reservoir for the Enzyme mix (3×) and one for the ATP mix (3×).

At the start of the run, the robot aspirates 5 microL of ATP mix, makes an air gap inside the tips (2 microL) and aspirates 2 microL of MPS1 mix. The following dispensation into the plates allows the kinase reaction to start upon 3 cycles of mixing, done by the robot itself.

At this point, the correct concentration is restored for all reagents.

The robot incubates the plates for 60 minutes at room temperature, and then stops the reaction by pipetting 70 microL of dowex resin suspension into the reaction mix. Three cycles of mixing are done immediately after the addition of the resin.

The resin suspension is very dense; in order to avoid tip clogging, wide bore tips are used to dispense it.

Another mixing cycle is performed after all the plates are stopped, this time using normal tips: the plates are then allowed to rest for about one hour in order to maximize ATP capture. At this point, 20 microL of the supernatant are transferred into 384-Optiplates (Perkin-Elmer), with 70 microL of Microscint 40 (Perkin-Elmer); after 5 min of orbital shaking the plates are read on a Perkin-Elmer Top Count radioactivity counter.

iii. Data Analysis

Data are analysed by an internally customized version of the SW package "Assay Explorer" that provides either % inhibition for primary assays or sigmoidal fittings of the ten-dilutions curves for IC$_{50}$ determination in the secondary assays/hit confirmation routines.

Biochemical Assay for Inhibitors of PLK-1 Kinase Activity

The inhibitory activity of putative kinase inhibitors and the potency of selected compounds were determined using a trans-phosphorylation assay.

Specific peptide or protein substrates are trans-phosphorylated by their specific serine-threonine or tyrosine kinase, in the presence of ATP traced with $^{33}$P-γ-ATP, and in the presence of their own optimal buffer and cofactors.

At the end of the phosphorylation reaction, more than 98% cold ATP and radioactive ATP is captured by an excess of the ion exchange dowex resin; the resin then settles down to the bottom of the reaction plate by gravity. Supernatant, containing the phosphorylated substrate, is subsequently withdrawn and transferred into a counting plate, then evaluated by β-counting.

Reagents/Assay Conditions i. Dowex Resin Preparation 500 g of wet resin (SIGMA, custom prepared resin DOWEX 1×8 200-400 mesh, 2.5 Kg) are weighed out and diluted to 2 L in 150 mM sodium formate, pH 3.00.

The resin is allowed to settle down (some hours) and then the supernatant is discarded.

After three washes as above over a couple of days, the resin is allowed to settle, the supernatant is discarded and two volumes of 150 mM sodium formate buffer are added per volume of pellet. The pH is then measured and should be around 3.00. The washed resin is stable for more than one week; the stock resin is kept at 4° C. before use.

ii. Kinase Buffer (KB)

Kinase buffer was composed of 50 mM HEPES pH 7.9 containing 10 mM MgCl$_2$, 1 mM DTT, 3 microM NaVO$_3$, and 0.2 mg/mL BSA, 10 mM □β-glycerophosphate.

iii. Assay Conditions

The kinase assay was run with a final enzyme concentration PLK-1 of 3 nM, in presence of 40 microM ATP, 3 nM $^{33}$P-γ-ATP and 85 microM substrate alpha-casein, SIGMA, #C-3240.

Robotized Dowex Assay
1) 3× Enzyme mix (done in Kinase Buffer 3×), 5 microL/well
2) 3× substrate and ATP mix (done in ddH$_2$O), together with $^{33}$P-γ-ATP, 5 microL/well
3) 3× test compounds (diluted into ddH$_2$O—3% DMSO)—5 microL/well Compound Dilution and Assay Scheme is Defined Below.

i. Dilution of Compounds 10 mM stock solutions of test compounds in 100% DMSO were distributed into 96 well 12×8 format microtiter plates.

For % inhibition studies, individual dilution plates at 1 mM, 100 microM and 10 microM are prepared in 100% DMSO, then diluted at a 3× concentration (30, 3 and 0.3 microM) in ddH$_2$O, 3% DMSO. A Multimek 96 (Beckman) is used for dilutions and compound pipetting into the test plates.

For IC$_{50}$ determination, compounds are received as 1 mM, 100% DMSO solutions, plated into the first column of a microtiter plate (A1 to G1), 100 microL.

A Biomek 2000 (Beckman) is used for serial 1:3 dilutions in water, 3% DMSO, from column A1 to A10 and for all the seven compounds in the plate. In a standard experiment, the highest concentration of all compounds is 30 microM, then diluted in the final test mixture down to 10 microM.

ii. Assay Scheme 384-well plates, V bottom (test plates) are prepared with 5 microL of the compound dilution (3×) and then placed onto a PlateTrak 12 robotized station (Perkin Elmer; the robot has one 384-tips pipetting head for starting the assay plus one 96-tips head for dispensing the resin) together with one reservoir for the Enzyme mix (3×) and one for the ATP mix (3×). At the start of the run, the robot aspirates 5 microL of ATP mix, makes an air gap inside the tips (3 microL) and aspirates 5 microL of PLK1 mix. The following dispensation into the plates allows the kinase reaction to start upon 3 cycles of mixing, done by the robot itself.

At this point, the correct concentration is restored for all reagents.

The robot incubates the plates for 60 minutes at room temperature, and then stops the reaction by pipetting 70 microL of dowex resin suspension into the reaction mix. Three cycles of mixing are done immediately after the addition of the resin.

Another mixing cycle is performed after all the plates are stopped, this time using normal tips: the plates are then allowed to rest for about one hour in order to maximize ATP capture. At this point, 20 microL of the supernatant are transferred into 384-Optiplates (Perkin-Elmer), with 70 microL of Microscint 40 (Perkin-Elmer); after 5 min of orbital shaking the plates are read on a Perkin-Elmer Top Count radioactivity counter.

iii. Data Analysis

Data are analysed by an internally customized version of the SW package "Assay Explorer" that provides either % inhibition for primary assays or sigmoidal fittings of the ten-dilutions curves for IC$_{50}$ determination, for the secondary assays/hit confirmation routines.

Biochemical Assay for Inhibitors of Aurora-2 Kinase Activity

The in vitro kinase inhibition assay was conducted in the same way as described for PLK-1 enzyme.

i. Kinase Buffer (KB) for Aurora-2

The kinase buffer was composed of 50 mM HEPES, pH 7.0, 10 mM MgCl$_2$, 1 mM DTT, 3 microM NaVO$_3$, and 0.2 mg/mL BSA.

ii. Assay Conditions for Aurora-2 (Final Concentrations)

The kinase assay was run with an enzyme concentration of 2.5 nM, 10 microM ATP, 1 nM $^{33}$P-γ-ATP, and 8 microM substrate, composed of 4 LRRWSLG repeats.

Inhibition Assay of Cdk2/Cyclin A Activity

Kinase reaction: 1.5 microM histone H1 substrate, 25 microM ATP (0.2 microCi P33γ-ATP), 30 ng of baculovirus co-expressed Cdk2/Cyclin A, 10 microM inhibitor in a final volume of 100 microL buffer (TRIS HCl 10 mM pH 7.5, MgCl$_2$ 10 mM, 7.5 mM DTT) were added to each well of a 96 U bottom well plate. After 10 min at 37° C. incubation, reaction was stopped by 20 microL EDTA 120 mM.

Capture: 100 microL were transferred from each well to MultiScreen plate, to allow substrate binding to phosphocellulose filter. Plates were then washed 3 times with 150 microL/well PBS Ca$^{++}$/Mg$^{++}$ free and filtered by Multi-Screen filtration system.

In Vitro Cell Proliferation Assay

A2780 human ovarian and MCF7 human breast cancer cells (1250 cells/well) were seeded in white 384 well-plates in complete medium (RPMI 1640 or EMEM plus 10% Fetal bovine serum) and treated with compounds dissolved in 0.1% DMSO, 24 h after seeding. The cells were incubated at 37° C. and 5% CO$_2$ and after 72 hours the plates were processed using CellTiter-Glo assay (Promega) following the manufacturer's instruction. CellTiter-Glo is a homogenous method based on the quantification of the ATP present, an indicator of metabolitically active cells. ATP is quantified using a system based on luciferase and D-luciferin resulting into light generation. The luminescent signal is proportional to the number of cells present in culture.

Briefly 25 μl/well reagent solution were added to each well and after 5 minutes shacking microplates were red by Envision (PerkinElmer) luminometer. The luminescent signal was proportional to the number of cells present in culture.

Inhibitory activity was evaluated comparing treated versus control data using Assay Explorer (MDL) program. IC$_{50}$ was calculated using sigmoidal interpolation curve.

Given the above inhibition assays, the compounds of the formula (I) of the invention resulted to possess a good MPS1 inhibitory activity, typically with an IC$_{50}$ in the range between 0.001 and 1 microM. Moreover, the compounds of the formula (I) of the invention show good cellular proliferation inhibitory activity, typically with an IC$_{50}$ in the range of from 0.010 to 1 μM in A2780 cells.

The following Table A reports the experimental data (IC$_{50}$ μM) obtained testing some representative compounds of the formula (I) of the invention, identified with the number used above, in A2780 cell proliferation assay, in comparison with a prior art compound, described in the aforementioned WO 04/104007, page 124, chemical name N-cyclohexyl-8-(cyclopentylamino)-N-hydroxy-1-methyl-4,5-dihydro-1H-pyrazolo[4,3-h]quinazoline-3-carboxamide, and coded therein B73-X00-M00(C01)-D29.

TABLE A

| Cell proliferation Assay Results | |
|---|---|
| Tested compound | A2780 IC$_{50}$ (μM) |
| Prior art compound | 3.4 |
| Compound number 2 | 0.15 |
| 3 | 0.35 |
| 5 | 0.10 |
| 7 | 0.14 |
| 13 | 0.10 |
| 56 | 0.15 |
| 57 | 0.13 |
| 66 | 0.65 |

The compounds of the present invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

If formulated as a fixed dose, such combination products employ the compounds of this invention within the dosage range described below and the other pharmaceutically active agent within the approved dosage range. Compounds of the formula (I) may be used sequentially with known anticancer agents when a combination formulation is inappropriate.

The compounds of the formula (I) of the present invention, suitable for administration to a mammal, e.g., to humans, can be administered by the usual routes and the dosage level depends upon the age, weight, conditions of the patient and administration route.

For example, a suitable dosage adopted for oral administration of a compound of the formula (I) may range from about 10 to about 500 mg per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of the formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form. For example, the solid oral forms may contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions. As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

With the aim of better illustrating the present invention, without posing any limitation to it, the following examples are now given.

EXAMPLES

The synthetic preparation of some compounds of the formula (I) of the invention is described in the following examples.

The compounds of the present invention, as prepared according to the following examples, were also characterized by $^1$H NMR or by HPLC/MS analytical data; HPLC/MS data were collected following any one of methods 1, 2, 3 and 4.

HPLC/MS Analytic Method 1

The HPLC equipment consisted of a Waters Acquity™ HPLC system equipped with a 2996 Waters PDA detector and Micromass mod. ZQ single quadrupole mass spectrometer, equipped with an electrospray (ESI) ion source. Instrument control, data acquisition and data processing were providen by Empower and MassLynx 4.0 software. HPLC was carried out at 45° C. at a flow rate of 0.8 mL/min using a BEH C18 1.7 microm Waters Acquity HPLC (2.1×50 mm) column. Mobile phase A was formic acid 0.1% pH=3.3 buffer with acetonitrile (98:2), and mobile phase B was $H_2O$/acetonitrile (5:95); the gradient was from 5 to 95% B in 2 minutes then hold 95% B 0.1 minutes. The injection volume was 2 microL. The mass spectrometer was operated in positive and in negative ion mode, the capillary voltage was set up at 3.5 KV ($ES^+$) and 28 V ($ES^-$); the source temperature was 120° C.; cone was 14 V ($ES^+$) and 2.8 KV ($ES^-$); full scan, mass range from 100 to 800 amu was set up.

HPLC/MS Analytic Method 2

The HPLC equipment consisted of a Waters 2795 Alliance HT system equipped with a 2996 Waters PDA detector and Micromass mod. ZQ single quadrupole mass spectrometer, equipped with an electrospray (ESI) ion source. Instrument control, data acquisition and data processing were providen by Empower and MassLynx 4.0 software. HPLC was carried out at 30° C. at a flow rate of 1.0 mL/min using a C18, 3 microm Phenomenex (4.6×50 mm) column. Mobile phase A was ammonium acetate 5 mM pH=5.2 buffer with acetonitrile (95:5), and mobile phase B was $H_2O$/acetonitrile (5:95); the gradient was from 10 to 90% B in 8 minutes then ramp to 100% B in 1.0 minutes. The injection volume was 10 microL. The mass spectrometer was operated in positive and in negative ion mode, the capillary voltage was set up at 3.5 KV ($ES^+$) and 28 V ($ES^-$); the source temperature was 120° C.; cone was 14 V ($ES^+$) and 2.8 KV ($ES^-$); full scan, mass range from 100 to 800 amu was set up.

HPLC/MS Analytic Method 3

The HPLC equipment consisted of a Waters Acquity™ HPLC system equipped with a 2996 Waters PDA detector and Micromass mod. ZQ single quadrupole mass spectrometer, equipped with an electrospray (ESI) ion source. Instrument control, data acquisition and data processing were providen by Empower and MassLynx 4.0 software. HPLC was carried out at 45° C. at a flow rate of 0.8 mL/min using a BEH C18 1.7 microm Waters Acquity HPLC (2.1×50 mm) column. Mobile phase A was ammonium hydroxide 0.05% pH=10 buffer with acetonitrile (95:5), and mobile phase B was $H_2O$/acetonitrile (5:95); the gradient was from 5 to 95% B in 2 minutes then hold 95% B 0.1 minutes. The injection volume was 2 microL. The mass spectrometer was operated in positive and in negative ion mode, the capillary voltage was set up at 3.5 KV ($ES^+$) and 28 V ($ES^-$); the source temperature was 120° C.; cone was 14 V ($ES^+$) and 2.8 KV ($ES^-$); full scan, mass range from 100 to 800 amu was set up.

HPLC/MS Analytical Method 4

The HPLC equipment consisted of a Waters 2790 HPLC system equipped with a 996 Waters PDA detector and Micromass mod. ZQ single quadrupole mass spectrometer, equipped with an electrospray (ESI) ion source. Instrument control, data acquisition and data processing were providen by Empower and MassLynx 4.0 software. HPLC was carried out at 25° C. at a flow rate of 1 mL/min using a RP18 Waters X Terra (3.0×20 mm) column. Mobile phase A was ammonium hydroxide 0.05% pH=10 buffer with acetonitrile (95:5), and Mobile phase B was $H_2O$/acetonitrile (5:95); the gradient was from 10 to 90% B in 4 minutes then hold 90% B1 minutes. The injection volume was 10 microL. The mass spectrometer was operated in positive and in negative ion mode, the capillary voltage was set up at 2.5 KV; the source temperature was 120° C.; cone was 10 V; full scan, mass range from 100 to 800 amu was set up.

Several compounds of the invention of the formula (I), as prepared according to the following examples, were purified by preparative HPLC.

The operative conditions are defined below:
HPLC/MS Preparative Method 1

The HPLC equipment consisted of a Waters 2790 HPLC system equipped with a 996 Waters PDA detector and Micromass mod. ZQ single quadrupole mass spectrometer, equipped with an electrospray (ESI) ion source. Instrument control, data acquisition and data processing were providen by Empower and MassLynx 4.0 software. HPLC was carried out at 25° C. at a flow rate of 20 ml/min using a RP18 Waters X Terra 10 microm (19×250 mm) column. Mobile phase A was ammonium hydroxide 0.05% pH=10 buffer with acetonitrile (95:5), and Mobile phase B was acetonitrile; the gradient was from 10 to 90% B in 15 minutes then hold 90% B 3 minutes. The injection volume was 10 microL.

The mass spectrometer was operated in positive and in negative ion mode, the capillary voltage was set up at 2.5 KV; the source temperature was 120° C.; cone was 10 V; full scan, mass range from 100 to 800 amu was set up.
HPLC/MS Preparative Method 2

The HPLC equipment consisted of a Waters 2790 HPLC system equipped with a 996 Waters PDA detector and Micromass mod. ZQ single quadrupole mass spectrometer, equipped with an electrospray (ESI) ion source. Instrument control, data acquisition and data processing were providen by Empower and MassLynx 4.0 software. HPLC was carried out at 25° C. at a flow rate of 20 ml/min using a RP18 Waters X Terra 10 microm (19×250 mm) column. Mobile phase A was 0.1% trifluoro acetic acid in water/acetonitrile (95:5), and mobile phase B was acetonitrile; the gradient was from 10 to 90% B in 15 minutes then hold 90% B 3 minutes. The injection volume was 10 microL.

The mass spectrometer was operated in positive and in negative ion mode, the capillary voltage was set up at 2.5 KV; the source temperature was 120° C.; cone was 10 V; full scan, mass range from 100 to 800 amu was set up.
MS Exact Exact mass data ESI(+) were obtained on a Waters Q-T of Ultima directly connected with micro HPLC 1100 Agilent as previously described (M. Colombo, F. Riccardi-Sirtori, V. Rizzo, *Rapid Commun. Mass Spectrom.* 2004, 18, 511-517).

The intermediate (VI) was prepared as described in WO 04/104007, Example 7 when R5 and R6 are hydrogen atom and Example 15 when R5 and R6 are both a methyl group.

Preparation 1

Ethyl 8-amino-1-methyl-1H-pyrazolo[4,3-h]quinazoline-3-carboxylate

To a solution of 16.62 g (60 mmol) of ethyl 6-[(dimethylamino)methylene]-7-oxo-1-methyl-4,5,6,7-tetrahydro-1H-indazole-3-carboxylate in 0.5 L of DMF, 27 g (150 mmol) of guanidine carbonate was added. The mixture was stirred at 110° C. overnight. After cooling the mixture was poured into water (2.5 L) and stirred for 30 minutes. The precipitate was filtered, washed with water and dried to yield 26.83 g of title compound (91%).

$^1$H NMR (400 MHz, DMSO-$d_6$) δ ppm: 1.28 (t, J=7.07 Hz, 3H) 2.68-2.93 (m, 4H) 4.25 (q, J=7.07 Hz, 2H) 4.30 (s, 3H) 6.54 (bs, 2H) 8.15 (m, 1H).

According to this same methodology, but employing a suitable substituted derivatives, the following compounds were prepared:

ethyl 8-(5-bromo-2-trifluoromethoxy-phenylamino)-4,5-dihydro-1H-pyrazolo[4,3-h]quinazoline-3-carboxylate $^1$H NMR (400 MHz, DMSO-$d_6$) δ ppm 1.34 (t, J=7.13 Hz, 3H) 2.89 (m, 2H) 2.99 (m, 2H) 4.33 (q, J=7.13 Hz, 2H) 7.34 (m, 2H) 8.31 (s, 1H) 8.43 (m, 1H) 8.70 (s, 1H) 9.06 (s, 1H) 14.28 (br. s., 1H);

ethyl 8-[5-(4-methyl-piperazin-1-yl)-2-trifluoromethoxy-phenylamino]-4,5-dihydro-1H-pyrazolo[4,3-h]quinazoline-3-carboxylate;

$^1$H NMR (400 MHz, DMSO-$d_6$) δ ppm 1.32 (t, J=7.1 Hz, 3H) 2.25 (s, 3H) 2.46 (m, 4H) 2.84 (m, 2H) 2.98 (m, 2H) 3.15 (m, 4H) 4.19 (s, 3H) 4.31 (q, J=7.1 Hz, 2H) 6.79 (m, 1H) 7.20 (m, 1H) 7.30 (m, 1H) 8.38 (bs, 1H) 8.94 (s, 1H);

ethyl 8-[2-methoxy-5-bromo-phenylamino]-4,5-dihydro-1H-pyrazolo[4,3-h]quinazoline-3-carboxylate;

$^1$H NMR (400 MHz, DMSO-$d_6$) δ ppm 1.32 (t, J=7.07 Hz, 3H) 2.88 (d, J=7.93 Hz, 2H) 2.96-3.03 (m, 2H) 3.88 (s, 3H) 4.30 (q, J=7.15 Hz, 2H) 4.34 (s, 3H) 7.03 (d, J=8.78 Hz, 1H) 7.19 (dd, J=8.66, 2.44 Hz, 1H) 8.26 (s, 1H) 8.37 (d, J=2.44 Hz, 1H) 8.47 (s, 1H);

ethyl 1-methyl-8-({4-[(1-methylpiperidin-4-yl)carbamoyl]-2-(trifluoromethoxy)phenyl}amino)-4,5-dihydro-1H-pyrazolo[4,3-h]quinazoline-3-carboxylate MS calc.: 574.2384; MS found: 574.2376 ethyl 8-{[2-methoxy-4-(4-methylpiperazin-1-yl)phenyl]amino}-1-methyl-4,5-dihydro-1H-pyrazolo[4,3-h]quinazoline-3-carboxylate MS calc.: 478.2561; MS found: 478.2574 ethyl 8-({2-methoxy-4-[(1-methylpiperidin-4-yl)carbamoyl]phenyl}amino)-1-methyl-4,5-dihydro-1H-pyrazolo[4,3-h]quinazoline-3-carboxylate MS calc.: 520.2667; MS found: 520.2667 ethyl 1-methyl-8-{[4-(4-methylpiperazin-1-yl)-2-(trifluoromethoxy)phenyl]amino}-4,5-dihydro-1H-pyrazolo[4,3-h]quinazoline-3-carboxylate MS calc.: 532.2278; MS found: 532.2275 ethyl 8-{[4-bromo-2-(trifluoromethoxy)phenyl]
amino}-1-methyl-4,5-dihydro-1H-pyrazolo[4,3-h]
quinazoline-3-carboxylate MS calc.: 512.0539; MS found: 512.0527 ethyl 1,5,5-trimethyl-8-({4-[(1-methylpiperidin-4-yl)
carbamoyl]-2-(trifluoromethoxy)phenyl}amino)-4,5-
dihydro-1H-pyrazolo[4,3-h]quinazoline-3-carboxylate MS calc.: 602.2697; MS found: 602.2703 and ethyl 8-({2-methoxy-4-[(1-methylpiperidin-4-yl)
carbamoyl]phenyl}amino)-1,5,5-trimethyl-4,5-dihydro-1H-pyrazolo[4,3-h]quinazoline-3-carboxylate MS calc.: 548.2980; MS found: 548.2978

Preparation 2

Ethyl 8-iodo-1-methyl-4,5-dihydro-1H-pyrazolo[4,3-h]quinazoline-3-carboxylate; To a well stirred suspension of ethyl 8-amino-1-methyl-4,5-dihydro-1H-pyrazolo[4,3-h]quinazoline-3-carboxylate (9.0 g, 33 mmol) in dimethoxyethane (0.7 L) under N2, cesium iodide (8.6 g, 33 mmol), bisublimated iodine (4.19 g, 16.5 mmol), copper iodide (2.0 g, 10 mmol) and isopentyl nitrite (6.62 mL, 49.5 mmol) were added in sequence. The reaction mixture was stirred vigorously at 65-70° C. for 3 hours. After cooling in an ice-water bath, the solid was filtered off. The filtrate was diluted with dichloromethane (2.0 L), washed with 30% ammonium hydroxide (150 mL), sodium thiosulphate (300 mL), brine, dried over anhydrous Na2SO4 and concentrated to give 5.69 g of the title compound (46% yield).

$^1$H NMR (400 MHz), DMSO-$d_6$), δ ppm 1.28 (t, J=7.07 Hz, 3H) 2.81-3.07 (2t, J=8.90 Hz, 4H) 4.24 (s, 3H) 4.27 (q, J=7.07 Hz, 2H) 8.5 (bs, 1H).

According to this same methodology, but employing suitable substituted derivatives, the following compounds were prepared:

ethyl 8-iodo-1-trityl-4,5-dihydro-1H-pyrazolo[4,3-h]
quinazoline-3-carboxylate $^1$H NMR (400 MHz, DMSO-$d_6$) δ ppm: 1.28 (t, J=7.07 Hz, 3H) 2.77 (m, 2H) 3.06 (m, 2H) 4.28 (q, J=7.07 Hz, 2H) 7.06-7.28 (m, 15H) 8.21 (s, 1H);

Preparation 3

Ethyl 8-[(4-bromo-2-cyanophenyl)amino]-1-methyl-4,5-dihydro-1H-pyrazolo[4,3-h]quinazoline-3-carboxylate To a solution of ethyl 8-amino-1-methyl-4,5-dihydro-1H-pyrazolo[4,3-h]quinazoline-3-carboxylate (207 mg, 0.753 mmol) in dioxane (6 mL), 5-bromo-2-iodobenzonitrile (260 mg, 0.627 mmol) and cesium carbonate (290 mg, 0.753 mmol) were added and the flask was evacuated and backfilled with argon. [Pd$_2$(dba)$_3$] (13 mg, 0.014 mmol) and X-phos (19 mg, 0.033 mmol) were then charged and the mixture was heated at 80° C. under argon for 8 hours. After cooling to room temperature, the reaction mixture was concentrated, suspended in water (10 mL) and extracted with ethyl acetate. The organic phase was anidrified on Na$_2$SO$_4$, filtered and evaporated to dryness, the crude solid was purified by flash chromatography on silica gel (eluant: dichloromethane/methanol 98/2) to afford 70 mg (20% yield) of the title compound.

MS calc.: 453.0669; MS found: 453.0659

According to this same methodology, but employing suitable substituted derivatives, the following compounds were prepared:

ethyl 8-[(4-bromo-2-methoxyphenyl)amino]-1-methyl-4,5-dihydro-1H-pyrazolo[4,3-h]quinazoline-3-carboxylate MS calc.: 458.0823; MS found: 458.0825 ethyl 8-[(4-bromo-2-methoxyphenyl)amino]-1,5,5-trimethyl-4,5-dihydro-1H-pyrazolo[4,3-h]quinazoline-3-carboxylate MS calc.: 486.1136; MS found: 486.1147 and ethyl 8-{[2-cyano-4-(4-methylpiperazin-1-yl)phenyl]
amino}-1-methyl-4,5-dihydro-1H-pyrazolo[4,3-h]
quinazoline-3-carboxylate MS calc.: 473.2408; MS found: 473.2394

Example 1

According to this same methodology described in Preparation 3 above, but employing suitable substituted derivatives, the following final compounds were analogously prepared:

tert-butyl 4-({3-[(2,6-diethylphenyl)carbamoyl]-1-methyl-4,5-dihydro-1H-pyrazolo[4,3-h]quinazolin-8-yl}amino)-3-methoxybenzoate MS calc.: 583.3028; MS found: 583.3025

8-[(2-chlorophenyl)amino]-N-(2,6-diethylphenyl)-1-methyl-4,5-dihydro-1H-pyrazolo[4,3-h]quinazoline-3-carboxamide MS calc.: 487.2008; MS found: 487.2005

8-[(4-bromo-2-cyanophenyl)amino]-N-(2,6-diethylphenyl)-1-methyl-4,5-dihydro-1H-pyrazolo[4,3-h]
quinazoline-3-carboxamide MS calc.: 556.1455; MS found; 556.1466

8-[(2-bromophenyl)amino]-N-(2,6-diethylphenyl)-1-methyl-4,5-dihydro-1H-pyrazolo[4,3-h]quinazoline-3-carboxamide MS calc.: 531.1503; MS found: 531.1502

N-(2,6-diethylphenyl)-8-[(2-methoxyphenyl)amino]-1-methyl-4,5-dihydro-1H-pyrazolo[4,3-h]quinazoline-3-carboxamide MS calc.: 483.2503; MS found: 483.2498

8-[(4-bromo-2-methoxyphenyl)amino]-N-(2,6-dimethylphenyl)-1,5,5-trimethyl-4,5-dihydro-1H-pyrazolo[4,3-h]quinazoline-3-carboxamide MS calc.: 561.1608; MS found 561.1617

8-[(5-bromo-2-methoxyphenyl)amino]-N-(2,6-diethylphenyl)-1-methyl-4,5-dihydro-1H-pyrazolo[4,3-h]quinazoline-3-carboxamide MS calc.: 561.1608; MS found: 561.1612

8-[(4-bromo-2-chlorophenyl)amino]-N-(2,6-diethylphenyl)-1-methyl-4,5-dihydro-1H-pyrazolo[4,3-h]quinazoline-3-carboxamide MS calc.: 565.1113; MS found: 565.1129 tert-butyl 4-({3-[(2,6-diethylphenyl)carbamoyl]-1-methyl-4,5-dihydro-1H-pyrazolo[4,3-h]quinazolin-8-yl}amino)-3-methylbenzoate N-(2,6-diethylphenyl)-8-[(2-methoxy-4-nitrophenyl)amino]-1-methyl-4,5-dihydro-1H-pyrazolo[4,3-h]quinazoline-3-carboxamide Preparation 4

Ethyl 1-methyl-8-({4-[(1-methylpiperidin-4-yl)carbamoyl]-2-(trifluoromethoxy)phenyl}amino)-4,5-dihydro-1H-pyrazolo[4,3-h]quinazoline-3-carboxylate Palladium acetate [Pd(OAc)$_2$] (101 mg, 0.45 mmol), (+)-BINAP (280 mg, 0.45 mmol) and dimethylformamide (70 mL) were charged to a round-bottom flask flushed with argon. The flask was evacuated and backfilled with argon. The mixture was stirred under argon for 30 minutes and added to a mixture of 4-amino-N-(1-methylpiperidin-yl)-3-(trifluoromethoxy)benzamide (3.78 g, 12.5 mmol), ethyl 8-iodo-1-methyl-4,5-dihydro-1H-pyrazolo[4,3-h]quinazoline-3-carboxylate (1.6 g, 4.16 mmol), and potassium carbonate (5.74 g, 41.6 mmol) in dimethylformamide (50 mL). The resulting mixture was stirred at 70° C. for 8 hours under argon. After cooling to room temperature, the reaction mixture was filtered on a pad of celite. The solvent was concentrated, the crude solid was purified by flash chromatography on silica gel (eluant: dichloromethane/ethanol 9/1) to afford 850 mg (45% yield) of the title compound.

MS calc.: 574.2384; MS found: 574.2376

Operating in an analogous way, the following compound was also prepared:

Ethyl 8-{[4-(tert-butyloxycarbonyl)-2-methoxyphenyl]amino}-1,5,5-trimethyl-4,5-dihydro-1H-pyrazolo[4,3-h]quinazoline-3-carboxylate MS calc.: 508.2555; MS found: 508.2553

Ethyl 8-{[4-({[tert-butyl(dimethyl)silyl]oxy}methyl)-2-methoxyphenyl]amino}-1-methyl-4,5-dihydro-1H-pyrazolo[4,3-h]quinazoline-3-carboxylate MS calc.: 524.2688; MS found: 524.2684

Preparation 5

8-Amino-1-methyl-4,5-dihydro-1H-pyrazolo[4,3-h]quinazoline-3-carboxylic acid

Ethyl 8-amino-1-methyl-4,5-dihydro-1H-pyrazolo[4,3-h]quinazoline-3-carboxylate (275 mg, 1 mmol) was to suspended in anhydrous ethanol (10 mL) and treated with a 2 M solution of sodium hydroxide (0.5 mL, 1 eq.) at reflux temperature for 1 hour. Solvent was evaporated to dryness and the residue dissolved in water. After treatment with acetic acid and the resulting precipitate was collected by filtration to give the title compound (180 mg, 74% yield) as a white solid.

MS calc.: 246.0986; MS found: 246.0984

According to this same methodology, but employing suitable substituted derivatives, the following compounds were prepared:

1-methyl-8-({4-[(1-methylpiperidin-4-yl)carbamoyl]-2-(trifluoromethoxy)phenyl}amino)-4,5-dihydro-1H-pyrazolo[4,3-h]quinazoline-3-carboxylic acid MS calc.: 546.2071; MS found: 546.2075

8-[(4-bromo-2-methoxyphenyl)amino]-1,5,5-trimethyl-4,5-dihydro-1H-pyrazolo[4,3-h]quinazoline-3-carboxylic acid MS calc.: 458.0823; MS found: 458.0822

8-({2-methoxy-4-[(1-methylpiperidin-4-yl)carbamoyl]phenyl}amino)-1-methyl-4,5-dihydro-1H-pyrazolo[4,3-h]quinazoline-3-carboxylic acid MS calc.: 478.2198; MS found: 478.2195

8-{[2-(methoxy)phenyl]amino}-1-methyl-4,5-dihydro-1H-pyrazolo[4,3-h]quinazoline-3-carboxylic acid MS calc.: 352.1404; MS found: 352.1404

8-amino-4,5-dihydro-1H-pyrazolo[4,3-h]quinazoline-3-carboxylic acid

MS calc.: 232.0829; Ms found 232.0824

8-[(4-bromo-2-frifluoromethoxyphenyl)amino]-1-methyl-4,5-dihydro-1H-pyrazolo[4,3-h]quinazoline-3-carboxylic acid MS calc.: 484.0227; MS found: 484.0213

8-{[4-({[tert-butyl(dimethyl)silyl]oxy}methyl)-2-methoxyphenyl]amino}-1-methyl-4,5-dihydro-1H-pyrazolo[4,3-h]quinazoline-3-carboxylic acid MS calc.: 496.2375; MS found: 496.2380

Preparation 6

8-Amino-N-(2,6-diethylphenyl)-1-methyl-4,5-dihydro-1H-pyrazolo[4,3-h]quinazoline-3-carboxamide A suspension of potassium 8-amino-1-methyl-4,5-dihydro-1H-pyrazolo[4,3-h]quinazoline-3-carboxylic acid (180 mg, 0.73 mmol) in anhydrous dimethylformamide (5.0 mL) was treated with N-ethyl-N,N-diisopropylamine (0.258 mL, 1.47 mmol) and N-ethyl-N',N'-diisopropyl carbodiimide hydrochloride (EDCI) (280 mg, 1.47 mmol) and 1-hydroxybenzotriazole (200 mg, 1.47 mmol). The mixture was then treated with 2,6-diethylaniline (0.170 mL, 1.1 mmol). The reaction was stirred at room temperature overnight. The reaction was diluted with water and the resulting precipitate was collected by filtration to afford the title compound (190 mg, 70% yield).

MS calc.: 377.2085; MS found: 377.2097

Example 2

According to this same methodology described in Preparation 6 above, but employing suitable derivatives as to starting materials, the following final compounds were analogously prepared:

N-(2,6-diethylphenyl)-1-methyl-8-({4-[(1-methylpiperidin-4-yl)carbamoyl]-2-(trifluoromethoxy)phenyl}amino)-4,5-dihydro-1H-pyrazolo[4,3-h]quinazoline-3-carboxamide MS calc.: 677.3170; MS found: 677.3181

N-(2,6-diethylphenyl)-8-({2-methoxy-4-[(1-methylpiperidin-4-yl)carbamoyl]phenyl}amino)-1-methyl-4,5-dihydro-1H-pyrazolo[4,3-h]quinazoline-3-carboxamide MS calc.: 623.3453; MS found: 623.3454

N-(2,6-diethylphenyl)-1-methyl-8-{[4-(4-methylpiperazin-1-yl)-2-(trifluoromethoxy)phenyl]amino}-4,5-dihydro-1H-pyrazolo[4,3-h]quinazoline-3-carboxamide MS calc.: 635.3065; MS found: 635.3071

8-[(4-carbamoyl-2-methylphenyl)amino]-N-(2,6-diethylphenyl)-1-methyl-4,5-dihydro-1H-pyrazolo[4,3-h]quinazoline-3-carboxamide MS calc.: 510.2612; MS found: 510.2617

N-(2,6-diethylphenyl)-8-{[2-methoxy-4-(4-methylpiperazin-1-yl)phenyl]amino}-1-methyl-4,5-dihydro-1H-pyrazolo[4,3-h]quinazoline-3-carboxamide MS calc.: 581.3347; MS found: 581.3344

8-[(4-bromo-2-methoxyphenyl)amino]-N-(2,6-diethylphenyl)-1-methyl-4,5-dihydro-1H-pyrazolo[4,3-h]quinazoline-3-carboxamide MS calc.: 561.1608; MS found: 561.1591

N-(2,6-diethylphenyl)-8-[(4-{[3-(dimethylamino)propyl](methyl)amino}-2-methoxyphenyl)amino]-1-methyl-4,5-dihydro-1H-pyrazolo[4,3-h]quinazoline-3-carboxamide MS calc.: 597.3660; MS found: 597.3638

1-methyl-8-({4-[(1-methylpiperidin-4-yl)carbamoyl]-2-(trifluoromethoxy)phenyl}amino)-N-phenyl-4,5-dihydro-1H-pyrazolo[4,3-h]quinazoline-3-carboxamide MS calc: 621.2544; MS found: 621.2535

N-(2-ethylphenyl)-1-methyl-8-({4-[(1-methylpiperidin-4-yl)carbamoyl]-2-(trifluoromethoxy)phenyl}amino)-4,5-dihydro-1H-pyrazolo[4,3-h]quinazoline-3-carboxamide MS calc.: 649.2857; MS found: 649.2847

1-methyl-N-(2-methylphenyl)-5-[2-({4-[(1-methylpiperidin-4-yl)carbamoyl]-2-(trifluoromethoxy)phenyl}amino)pyrimidin-4-yl]-1H-pyrrole-3-carboxamide MS calc.: 608.2592; MS found: 608.2579

N-(2-ethylphenyl)-8-{[2-methoxy-4-(4-methylpiperazin-1-yl)phenyl]amino}-1-methyl-4,5-dihydro-1H-pyrazolo[4,3-h]quinazoline-3-carboxamide MS calc.: 553.3034; MS found: 553.3024

N-(2,3-dihydro-1H-inden-5-yl)-8-{[2-methoxy-4-(4-methylpiperazin-1-yl)phenyl]amino}-1-methyl-4,5-dihydro-1H-pyrazolo[4,3-h]quinazoline-3-carboxamide MS calc.: 565.3034; MS found: 565.3040

8-{[2-methoxy-4-(4-methylpiperazin-1-yl)phenyl]amino}-1-methyl-N-(5,6,7,8-tetrahydronaphthalen-1-yl)-4,5-dihydro-1H-pyrazolo[4,3-h]quinazoline-3-carboxamide MS calc.: 579.3191; MS found: 579.3190

3-(2,3-dihydro-1H-indol-1-ylcarbonyl)-N-[2-methoxy-4-(4-methylpiperazin-1-yl)phenyl]-1-methyl-4,5-dihydro-1H-pyrazolo[4,3-h]quinazolin-8-amine MS calc.: 551.2878; MS found: 551.2873

N-(2,6-dimethylphenyl)-8-{[2-methoxy-4-(4-methylpiperazin-1-yl)phenyl]amino}-1-methyl-4,5-dihydro-1H-pyrazolo[4,3-h]quinazoline-3-carboxamide MS calc.: 553.3034; MS found: 553.3036

N-(2-ethyl-6-methylphenyl)-8-{[2-methoxy-4-(4-methylpiperazin-1-yl)phenyl]amino}-1-methyl-4,5-dihydro-1H-pyrazolo[4,3-h]quinazoline-3-carboxamide MS calc.: 567.3191; MS found: 567.3179

8-{[2-methoxy-4-(4-methylpiperazin-1-yl)phenyl]amino}-N-(2-methoxyphenyl)-1-methyl-4,5-dihydro-1H-pyrazolo[4,3-h]quinazoline-3-carboxamide MS calc: 555.2827; MS found: 555.2807

N-1,3-benzothiazol-5-yl-8-{[2-methoxy-4-(4-methylpiperazin-1-yl)phenyl]amino}-1-methyl-4,5-dihydro-1H-pyrazolo[4,3-h]quinazoline-3-carboxamide MS calc.: 582.2394; MS found: 582.2393

N-(2-chloro-6-methylphenyl)-8-{[2-methoxy-4-(4-methylpiperazin-1-yl)phenyl]amino}-1-methyl-4,5-dihydro-1H-pyrazolo[4,3-h]quinazoline-3-carboxamide MS calc.: 573.2488; MS found: 573.2487

N-[2,6-bis(1-methylethyl)phenyl]-8-{[2-methoxy-4-(4-methylpiperazin-1-yl)phenyl]amino}-1-methyl-4,5-dihydro-1H-pyrazolo[4,3-h]quinazoline-3-carboxamide MS calc.: 609.3660; MS found: 609.3656

N-(2,6-dimethylphenyl)-8-{[2-methoxy-4-(4-methylpiperazin-1-yl)phenyl]amino}-1,5,5-trimethyl-4,5-dihydro-1H-pyrazolo[4,3-h]quinazoline-3-carboxamide MS calc.: 581.3347; MS found: 581.3359

8-{[4-({[tert-butyl(dimethyl)silyl]oxy}methyl)-2-methoxyphenyl]amino}-N-(2,6-diethylphenyl)-1-methyl-4,5-dihydro-1H-pyrazolo[4,3-h]quinazoline-3-carboxamide MS calc.: 627.3474; MS found: 627.3478

Example 3 tert-Butyl 4-({3-[(2,6-diethylphenyl)carbamoyl]-1-methyl-4,5-dihydro-1H-pyrazolo[4,3-h]quinazolin-8-yl}amino)piperidine-1-carboxylate To a solution of 8-amino-N-(2,6-diethylphenyl)-1-methyl-4,5-dihydro-1H-pyrazolo[4,3-h]quinazoline-3-carboxamide (1.0 g, 2.66 mmol) in dry dimethylformamide (20 mL), were added 1-Boc-4-piperidone (1.06 g mL, 5.32 mmol), $CF_3COOH$ (1.7 mL, 22.7 mmol) and $NaBH(OAc)_3$ (1.12 g, 5.32 mmol). After 20 hours, NaOH 2N (12 mL, 24 mmol) was added dropwise to the mixture. The precipitate was filtered, washed with water and dried. The crude material was purified by flash chromatography on silica gel eluted with dichloromethane/methanol 97:3 to give the 1.2 g of to the pure title compound (80% yield).

MS calc: 560.3365; MS found: 560.3344

Example 4

N-(2,6-Diethylphenyl)-1-methyl-8-(piperidin-4-ylamino)-4,5-dihydro-1H-pyrazolo[4,3-h]quinazoline-3-carboxamide hydrochloride To a solution of tert-butyl 4-({3-[(2,6-diethylphenyl)carbamoyl]-1-methyl-4,5-dihydro-1H-pyrazolo[4,3-h]quinazolin-8-yl}amino)piperidine-1-carboxylate (7.1 g, 12.7 mmol) in dioxane (50 mL), 4M HCl in dioxane (10 mL, 32 mmol) was added. The mixture was stirred at room temperature for 1 h. The solvent was removed under reduced pressure to give the title compound as a hydrochloride salt in quantitative yield. The title compound:

MS calc.: 460.2840; MS found: 460.2820

Example 5

8-[(1-Benzylpiperidin-4-yl)amino]-N-(2,6-diethylphenyl)-1-methyl-4,5-dihydro-1H-pyrazolo[4,3-h]quinazoline-3-carboxamide To a solution of N-(2,6-diethylphenyl)-1-methyl-8-(piperidin-4-ylamino)-4,5-dihydro-1H-pyrazolo[4,3-h]quinazoline-3-carboxamide hydrochloride (40 mg, 0.075 mmol) in dichloromethane (1 mL), DIPEA (0.2 mL, 1.1 mmol) and benzylbromide (0.011 mL, 0.090 mmol) were added. The mixture was stirred at room temperature for 2 h. Dichloromethane was added and the solution was washed water. The organic layer was then dried over $Na_2SO_4$ and the solvent evaporated to dryness. The crude solid was purified by flash chromatography on silica gel (eluant: dichloromethane/methanol: 95/5) to 31 mg of the title compound. (75% yield)

MS calc.: 550.3284 MS found: 550.3289

According to this same methodology, but employing suitable substituted derivatives, the following compound was prepared:

N-(2,6-diethylphenyl)-8-[(1-ethylpiperidin-4-yl)amino]-1-methyl-4,5-dihydro-1H-pyrazolo[4,3-h]quinazoline-3-carboxamide MS calc.: 488.3133; MS found: 488.3133

Example 6

8-[(1-acetylpiperidin-4-yl)amino]-N-(2,6-diethylphenyl)-1-methyl-4,5-dihydro-1H-pyrazolo[4,3-h]quinazoline-3-carboxamide To a solution of N-(2,6-diethylphenyl)-1-methyl-8-(piperidin-4-ylamino)-4,5-dihydro-1H-pyrazolo[4,3-h]quinazoline-3-carboxamide hydrochloride (40 mg, 0.075 mmol) in dimethylformamide (1 mL), DIPEA (0.2 mL, 1.1 mmol), N-ethyl-N',N'-diisopropyl carbodiimide hydrochloride (EDCI) (22 mg, 0.113 mmol), 1-hydroxy-benzotriazole (18 mg, 0.113 mmol) and acetic acid (0.005 mL, 0.009 mmol) were added. The mixture was stirred at room temperature for 6 h. Water was added and the mixture extracted with ethylacetate. The organic layer was washed with brine then dried over $Na_2SO_4$ and the solvent evaporated to dryness. The crude solid was purified by flash chromatography on silica gel (eluant: dichloromethane/methanol: 97/3) to 29 mg of the title compound. (77% yield)

MS calc.: 502.2927 MS found: 502.2925

According to this same methodology, but employing suitable substituted derivatives, the following compounds were prepared:

N-(2,6-diethylphenyl)-1-methyl-8-{[1-(phenylcarbonyl)piperidin-4-yl]amino}-4,5-dihydro-1H-pyrazolo[4,3-h]quinazoline-3-carboxamide Ms calc.: 564.3084; MS found: 564.3082 and N-(2,6-diethylphenyl)-1-methyl-8-({1-[(1-methylpiperidin-4-yl)carbonyl]piperidin-4-yl}amino)-4,5-dihydro-1H-pyrazolo[4,3-h]quinazoline-3-carboxamide MS calc.: 585.3660; MS found: 585.3660

N-(2,6-diethylphenyl)-1-methyl-8-({1-[(5-methyl-isoxazol-4-yl)carbonyl]piperidin-4-yl}amino)-4,5-dihydro-1H-pyrazolo[4,3-h]quinazoline-3-carboxamide MS calc.: 569.2983; MS found: 569.2993

N-(2,6-diethylphenyl)-1-methyl-8-({1-[(1-methyl-1H-imidazol-4-yl)carbonyl]piperidin-4-yl}amino)-4,5-dihydro-1H-pyrazolo[4,3-h]quinazoline-3-carboxamide MS calc.: 568.3143; MS found: 568.3149

N-(2,6-diethylphenyl)-1-methyl-8-{[1-(pyrimidin-4-ylcarbonyl)piperidin-4-yl]amino}-4,5-dihydro-1H-pyrazolo[4,3-h]quinazoline-3-carboxamide MS calc.: 566.2987; MS found: 566.2983

N-(2,6-diethylphenyl)-1-methyl-8-{[1-(1H-pyrrol-2-ylcarbonyl)piperidin-4-yl]amino}-4,5-dihydro-1H-pyrazolo[4,3-h]quinazoline-3-carboxamide MS calc.: 553.3034; MS found: 553.3035

N-(2,6-diethylphenyl)-8-{[1-(1H-imidazol-4-ylcarbonyl)piperidin-4-yl]amino}-1-methyl-4,5-dihydro-1H-pyrazolo[4,3-h]quinazoline-3-carboxamide MS calc.: 554.2987; MS found: 554.2989

N-(2,6-diethylphenyl)-1-methyl-8-{[1-(pyridin-3-ylcarbonyl)piperidin-4-yl]amino}-4,5-dihydro-1H-pyrazolo[4,3-h]quinazoline-3-carboxamide MS calc.: 565.3034; MS found: 565.3038

N-(2,6-diethylphenyl)-1-methyl-8-{[1-(pyridin-2-ylcarbonyl)piperidin-4-yl]amino}-4,5-dihydro-1H-pyrazolo[4,3-h]quinazoline-3-carboxamide MS calc.: 565.3034; MS found: 565.3046

N-(2,6-diethylphenyl)-1-methyl-8-{[1-(1H-pyrazol-4-ylcarbonyl)piperidin-4-yl]amino}-4,5-dihydro-1H-pyrazolo[4,3-h]quinazoline-3-carboxamide MS calc.: 554.2987; MS found: 554.3000

N-(2,6-diethylphenyl)-1-methyl-8-{[1-(thiophen-3-ylcarbonyl)piperidin-4-yl]amino}-4,5-dihydro-1H-pyrazolo[4,3-h]quinazoline-3-carboxamide MS calc.: 570.2646; MS found: 570.2636

N-(2,6-diethylphenyl)-1-methyl-8-{[1-(pyridin-4-ylcarbonyl)piperidin-4-yl]amino}-4,5-dihydro-1H-pyrazolo[4,3-h]quinazoline-3-carboxamide MS calc.: 565.3034; MS found: 565.3038

N-(2,6-diethylphenyl)-1-methyl-8-{[1-(1H-pyrrol-3-ylcarbonyl)piperidin-4-yl]amino}-4,5-dihydro-1H-pyrazolo[4,3-h]quinazoline-3-carboxamide MS calc.: 553.3034; MS found: 553.3039

Example 7

N-(2,6-Diethylphenyl)-1-methyl-8-{[1-(methylsulfonyl)piperidin-4-yl]amino}-4,5-dihydro-1H-pyrazolo[4,3-h]quinazoline-3-carboxamide To a solution of N-(2,6-diethylphenyl)-1-methyl-8-(piperidin-4-ylamino)-4,5-dihydro-1H-pyrazolo[4,3-h]quinazoline-3-carboxamide hydrochloride (40 mg, 0.075 mmol) in dichloromethane (1 mL) at 0° C., DIPEA (0.2 mL, 1.1 mmol), and methanesulfonyl chloride (0.007 mL, 0.009 mmol) were added. The mixture was then stirred at room temperature for 3 h. Solvent evaporated to dryness and the crude solid was purified by flash chromatography on silica gel (eluant: dichloromethane/methanol: 97/3) to 26 mg of the title compound. (64% yield)

MS calc.: 538.2581; MS found: 538.2595

According to this same methodology, but employing suitable substituted derivatives, the following compounds were prepared:

N-(2,6-diethylphenyl)-1-methyl-8-{[1-(phenylsulfonyl)piperidin-4-yl]amino}-4,5-dihydro-1H-pyrazolo[4,3-h]quinazoline-3-carboxamide MS calc.: 600.2755; MS found: 600.2752 and 8-({1-[(3-chloropropyl)sulfonyl]piperidin-4-yl}amino)-N-(2,6-diethylphenyl)-1-methyl-4,5-dihydro-1H-pyrazolo[4,3-h]quinazoline-3-carboxamide MS calc.: 600.2512; MS found: 600.2518

N-(2,6-diethylphenyl)-1-methyl-8-({1-[(2,2,2-trifluoroethyl)sulfonyl]piperidin-4-yl}amino)-4,5-dihydro-1H-pyrazolo[4,3-h]quinazoline-3-carboxamide MS calc.: 606.2469; MS found: 606.2456

N-(2,6-diethylphenyl)-1-methyl-8-({1-[(trifluoromethyl)sulfonyl]piperidin-4-yl}amino)-4,5-dihydro-1H-pyrazolo[4,3-h]quinazoline-3-carboxamide MS calc.: 592.2312; MS found: 592.2302

N-(2,6-diethylphenyl)-1-methyl-8-{[1-(1H-pyrazol-4-ylsulfonyl)piperidin-4-yl]amino}-4,5-dihydro-1H-pyrazolo[4,3-h]quinazoline-3-carboxamide MS calc.: 590.2657; MS found: 590.2643

N-(2,6-diethylphenyl)-8-{[1-(1H-imidazol-4-ylsulfonyl)piperidin-4-yl]amino}-1-methyl-4,5-dihydro-1H-pyrazolo[4,3-h]quinazoline-3-carboxamide MS calc.: 590.2657; MS found: 590.2657

N-(2,6-diethylphenyl)-1-methyl-8-({1-[(4-methyl-3,4-dihydro-2H-1,4-benzoxazin-7-yl)sulfonyl]piperidin-4-yl}amino)-4,5-dihydro-1H-pyrazolo[4,3-h]quinazoline-3-carboxamide MS calc.: 671.3123; MS found: 671.3129

N-(2,6-diethylphenyl)-8-{[1-(dimethylsulfamoyl)
piperidin-4-yl]amino}-1-methyl-4,5-dihydro-1H-
pyrazolo[4,3-h]quinazoline-3-carboxamide MS calc.: 567.2861; MS found: 567.2863

N-(2,6-diethylphenyl)-1-methyl-8-({1-[(1-methyl-
1H-imidazol-4-yl)sulfonyl]piperidin-4-yl}amino)-4,
5-dihydro-1H-pyrazolo[4,3-h]quinazoline-3-car-
boxamide MS calc.: 604.2813; MS found: 604.2797

N-(2,6-diethylphenyl)-1-methyl-8-{[1-(pyridin-3-
ylsulfonyl)piperidin-4-yl]amino}-4,5-dihydro-1H-
pyrazolo[4,3-h]quinazoline-3-carboxamide MS calc.: 601.2704; MS found: 601.2691

8-[(1-{[4-(acetylamino)phenyl]sulfonyl}piperidin-4-
yl)amino]-N-(2,6-diethylphenyl)-1-methyl-4,5-dihy-
dro-1H-pyrazolo[4,3-h]quinazoline-3-carboxamide MS calc.: 657.2966; MS found: 657.2986

8-({1-[(chloromethyl)sulfonyl]piperidin-4-
yl}amino)-N-(2,6-diethylphenyl)-1-methyl-4,5-dihy-
dro-1H-pyrazolo[4,3-h]quinazoline-3-carboxamide MS calc.: 572.2205; MS found: 572.2219

N-(2,6-diethylphenyl)-8-({1-[(2-hydroxyethyl)sulfo-
nyl]piperidin-4-yl}amino)-1-methyl-4,5-dihydro-1H-
pyrazolo[4,3-h]quinazoline-3-carboxamide MS calc.: 568.2701; MS found: 568.2685

N-(2,6-diethylphenyl)-8-({1-[(2-methoxyethyl)sulfo-
nyl]piperidin-4-yl}amino)-1-methyl-4,5-dihydro-1H-
pyrazolo[4,3-h]quinazoline-3-carboxamide MS calc.: 582.2857; MS found: 582.2873

N-(2,6-diethylphenyl)-1-methyl-8-{[trans-4-({[2-
(methylamino)ethyl]sulfonyl}amino)cyclohexyl]
amino}-4,5-dihydro-1H-pyrazolo[4,3-h]quinazoline-
3-carboxamide MS calc.: 595.3174; MS found: 595.3177

8-({1-[(4-aminophenyl)sulfonyl]piperidin-4-
yl}amino)-N-(2,6-diethylphenyl)-1-methyl-4,5-dihy-
dro-1H-pyrazolo[4,3-h]quinazoline-3-carboxamide
hydrochloride MS calc.: 615.2861; MS found: 615.2858

N-(2,6-diethylphenyl)-8-[(3,3-dimethyl-1-{[2-(me-
thylamino)ethyl]sulfonyl}piperidin-4-yl)amino]-1-
methyl-4,5-dihydro-1H-pyrazolo[4,3-h]quinazoline-
3-carboxamide MS calc.: 609.3330 MS found: 609.3336

Example 8

N-(2,6-diethylphenyl)-8-{[1-(ethenylsulfonyl)piperi-
din-4-yl]amino}-1-methyl-4,5-dihydro-1H-pyrazolo
[4,3-h]quinazoline-3-carboxamide To a solution of N-(2,6-diethylphenyl)-1-methyl-8-(piperidin-4-ylamino)-4,5-dihydro-1H-pyrazolo[4,3-h]quinazoline-3-carboxamide hydrochloride (300 mg, 0.606 mmol) under nitrogen, in dry dichloromethane (15 mL), DIPEA (0.527 mL, 3.03 mmol) and 300 mg of molecular sieves were added, and the mixture was cooled at −78° C. 2-chloroethane-sulfonyl chloride (0.063 mL, 0.606 mmol) was added. Temperature was allow to rise to room temperature then the solvent was evaporated to dryness and the crude was purified by flash chromatography on silica gel (eluant: ethyl acetate/dichloromethane: 2/8) to give 185 mg of the title compound (56% yield).

MS calc.: 550.2596; MS found: 550.2595

Example 9

N-(2,6-diethylphenyl)-8-[(1-{[2-(dimethylamino)
ethyl]sulfonyl}piperidin-4-yl)amino]-1-methyl-4,5-
dihydro-1H-pyrazolo[4,3-h]quinazoline-3-carboxa-
mide To a solution of N-(2,6-diethylphenyl)-8-{[1-(ethenylsul-fonyl)piperidin-4-yl]amino}-1-methyl-4,5-dihydro-1H-pyrazolo[4,3-h]quinazoline-3-carboxamide (30 mg, 0.0055 mmol) in ethanol (3 mL) dimethylamine (20% acqueous solution) (1 mL) was added. The mixture was then stirred at room temperature for 30 minutes. Solvent evaporated to dryness and the crude solid was purified by flash chromatography on silica gel (eluant: dichloromethane/methanol: 97/3) to 28 mg of the title compound (86% yield).

MS calc.: 595.3174; MS found: 595.3179

According to this same methodology, but employing suitable substituted derivatives, the following compounds were prepared:

N-(2,6-diethylphenyl)-1-methyl-8-[(1-{[2-(methy-
lamino)ethyl]sulfonyl}piperidin-4-yl)amino]-4,5-
dihydro-1 H-pyrazolo[4,3-h]quinazoline-3-carboxa-
mide MS calc.: 581.3024; MS found: 581.3017

N-(2,6-diethylphenyl)-1-methyl-8-[(1-{[2-(4-meth-
ylpiperazin-1-yl)ethyl]sulfonyl}piperidin-4-yl)
amino]-4,5-dihydro-1H-pyrazolo[4,3-h]quinazoline-
3-carboxamide MS calc.: 650.3596; MS found: 650.3613

N-(2,6-diethylphenyl)-8-[(1-{[2-(dimethylamino)
ethyl]sulfonyl}piperidin-4-yl)amino]-1-methyl-4,5-
dihydro-1H-pyrazolo[4,3-h]quinazoline-3-carboxa-
mide MS calc.: 595.3174; MS found: 595.3179

N-(2,6-diethylphenyl)-1-methyl-8-({1-[(2-piperidin-
1-ylethyl)sulfonyl]piperidin-4-yl}amino)-4,5-dihy-
dro-1H-pyrazolo[4,3-h]quinazoline-3-carboxamide MS calc.: 635.3487; MS found: 635.3507

N-(2,6-diethylphenyl)-1-methyl-8-({1-[(2-morpho-
lin-4-ylethyl)sulfonyl]piperidin-4-yl}amino)-4,5-
dihydro-1H-pyrazolo[4,3-h]quinazoline-3-carboxa-
mide MS calc.: 637.3279; MS found: 637.3291

N-(2,6-diethylphenyl)-1-methyl-8-({1-[(2-pyrrolidin-1-ylethyl) sulfonyl]piperidin-4-yl}amino)-4,5-dihydro-1H-pyrazolo[4,3-h]quinazoline-3-carboxamide MS calc.: 621.333; MS found 621.3337

8-({1-[(2-aminoethyl)sulfonyl]piperidin-4-yl}amino)-N-(2,6-diethylphenyl)-1-methyl-4,5-dihydro-1H-pyrazolo[4,3-h]quinazoline-3-carboxamide MS calc.: 567.2861; MS found: 567.2854

N-(2,6-diethylphenyl)-8-[(1-{[2-(ethylamino)ethyl]sulfonyl}piperidin-4-yl)amino]-1-methyl-4,5-dihydro-1H-pyrazolo[4,3-h]quinazoline-3-carboxamide MS calc.: 595.3174; MS found: 595.3183

Example 10

N-(2,6-Diethylphenyl)-1-methyl-8-[(1-{[3-(methylamino)propyl]sulfonyl}piperidin-4-yl)amino]-4,5-dihydro-1H-pyrazolo[4,3-h]quinazoline-3-carboxamide hydrochloride To a solution of 8-({1-[(3-chloropropyl)sulfonyl]piperidin-4-yl}amino)-N-(2,6-diethylphenyl)-1-methyl-4,5-dihydro-1H-pyrazolo[4,3-h]quinazoline-3-carboxamide (30 mg, 0.050 mmol) in tetrahydrofurane (2 mL) in a sealed tube, methylamine (40% aqueous solution) (0.5 mL) was added. The mixture was then heated at 60° C. for 20 h. Solvent evaporated to dryness and the crude solid was purified by flash chromatography on silica gel (eluant: dichloromethane/methanol: 8/2) to 23 mg of the title compound (76% yield).
MS calc.: 595.3199; MS found: 595.3174

Example 11

N-(2,6-Diethylphenyl)-8-{[2-methoxy-4-(4-methylpiperazin-1-yl)phenyl]amino}-1-methyl-4,5-dihydro-1H-yrazolo[4,3-h]quinazoline-3-carboxamide Tris(dibenzilideneacetone)dipalladium, Pd$_2$(dba)$_3$, (3.97 mg, 0.004 mmol), 2-dicyclohexylphosphino-2'-(N,N-dimethylamino)-biphenyl (3.86 mg, 0.009 mmol), 8-[(4-bromo-2-methoxyphenyl)amino]-N-(2,6-diethylphenyl)-1-methyl-4,5-dihydro-1H-pyrazolo[4,3-h]quinazoline-3-carboxamide (250 mg, 0.433 mmol) in THF (2.25 mL) were charged in a round-bottom flask flushed with argon. The flask was evacuated and backfilled with argon. LiN(TMS)$_2$ solution (1M in THF, 3.5 mL) and N—N-methyl ethylpiperazine (0.14 mL, 1.3 mmol) were added and the reaction mixture refluxed for 0.5 h. The reaction mixture was then allowed to cool to room temperature and concentrated. The crude solid was purified by flash chromatography on silica gel (eluant: DCM/EtOH 97/3) to afford 228 mg (90% yield) of the title compound.
MS calc.: 581.3347; MS found: 581.334399
According to this same methodology, but employing suitable substituted derivatives, the following compounds were prepared:

N-(2,6-diethylphenyl)-8-{[2-methoxy-4-(4-methyl-1,4-diazepan-1-yl)phenyl]amino}-1-methyl-4,5-dihydro-1H-pyrazolo[4,3-h]quinazoline-3-carboxamide MS calc.: 595.3504; MS found: 595.3506

N-(2,6-diethyl phenyl)-8-[(4-{[2-(dimethylamino)ethyl](methyl)amino}-2-methoxyphenyl)amino]-1-methyl-4,5-dihydro-1H-pyrazolo[4,3-h]quinazoline-3-carboxamide MS calc.: 583.3504; MS found: 583.3506

8-{[2-cyano-4-(4-methylpiperazin-1-yl)phenyl]amino}-N-(2,6-diethylphenyl)-1-methyl-4,5-dihydro-1H-pyrazolo[4,3-h]quinazoline-3-carboxamide MS calc.: 576.3194; MS found: 576.3188

8-{[2-cyano-4-(4-methyl-1,4-diazepan-1-yl)phenyl]amino}-N-(2,6-diethylphenyl)-1-methyl-4,5-dihydro-1H-pyrazolo[4,3-h]quinazoline-3-carboxamide MS calc.: 590.3351; MS found: 590.3367

N-(2,6-diethylphenyl)-8-({2-methoxy-4-[(2-methoxyethyl)amino]phenyl}amino)-1-methyl-4,5-dihydro-1H-pyrazolo[4,3-h]quinazoline-3-carboxamide MS calc.: 556.3031; MS found: 556.3022

N-(2,6-diethylphenyl)-8-{[2-methoxy-5-(4-methylpiperazin-1-yl)phenyl]amino}-1-methyl-4,5-dihydro-1H-pyrazolo[4,3-h]quinazoline-3-carboxamide MS calc.: 581.3347; MS found: 581.3340

N-(2,6-diethylphenyl)-8-({4-[(3R)-3-(dimethylamino)pyrrolidin-1-yl]-2-methoxyphenyl}amino)-1-methyl-4,5-dihydro-1H-pyrazolo[4,3-h]quinazoline-3-carboxamide MS calc.: 595.3504; MS found: 595.3512

N-(2,6-diethylphenyl)-8-({4-[(3S)-3-(dimethylamino)pyrrolidin-1-yl]-2-methoxyphenyl}amino)-1-methyl-4,5-dihydro-1H-pyrazolo[4,3-h]quinazoline-3-carboxamide MS calc.: 595.3504; MS found: 595.3502

N-(2,6-diethylphenyl)-8-({4-[4-(2-hydroxyethyl)piperazin-1-yl]-2-methoxyphenyl}amino)-1-methyl-4,5-dihydro-1H-pyrazolo[4,3-h]quinazoline-3-carboxamide MS calc.: 611.3453; MS found: 611.3432

N-(2,6-diethylphenyl)-8-[(4-{[2-(dimethylamino)ethyl]amino}-2-methoxyphenyl)amino]-1-methyl-4,5-dihydro-1H-pyrazolo[4,3-h]quinazoline-3-carboxamide MS calc.: 569.3347; MS found: 569.3345

N-(2,6-diethylphenyl)-8-{[2-methoxy-4-(4-pyrrolidin-1-ylpiperidin-1-yl)phenyl]amino}-1-methyl-4,5-dihydro-1H-pyrazolo[4,3-h]quinazoline-3-carboxamide MS calc.: 635.3817; MS found: 635.3815

N-(2,6-diethylphenyl)-8-{[2-methoxy-4-(tetrahydro-2H-pyran-4-ylamino)phenyl]amino}-1-methyl-4,5-dihydro-1H-pyrazolo[4,3-h]quinazoline-3-carboxamide MS calc: 582.3187; MS found: 582.3195

8-{[2-chloro-4-(4-methylpiperazin-1-yl)phenyl]amino}-N-(2,6-diethylphenyl)-1-methyl-4,5-dihydro-1H-pyrazolo[4,3-h]quinazoline-3-carboxamide MS calc.: 585.2852; MS found: 585.2851

8-[(2-chloro-4-{[3-(dimethylamino)propyl](methyl)amino}phenyl)amino]-N-(2,6-diethylphenyl)-1-methyl-4,5-dihydro-1H-pyrazolo[4,3-h]quinazoline-3-carboxamide MS calc.: 601.3165; MS found: 601.3169

8-({2-chloro-4-[4-(dimethylamino)piperidin-1-yl]phenyl}amino)-N-(2,6-diethylphenyl)-1-methyl-4,5-dihydro-1H-pyrazolo[4,3-h]quinazoline-3-carboxamide MS calc.: 613.3165; MS found: 613.3167

Example 12

4-({3-[(2,6-Diethylphenyl)carbamoyl]-1-methyl-4,5-dihydro-1H-pyrazolo[4,3-h]quinazolin-8-yl}amino)-3-methoxybenzoic acid To a solution of tert-butyl 4-({3-[(2,6-diethylphenyl)carbamoyl]-1-methyl-4,5-dihydro-1H-pyrazolo[4,3-h]quinazolin-8-yl}amino)-3-methoxybenzoate (500 mg, 0.857 mmol) in dimethylformamide (8 mL), trifluoro acetic acid (0.600 mL), were added. The mixture was stirred at room temperature overnight. Water was added and the mixture extracted with ethylacetate. The organic solvent evaporated to dryness. To give 450 mg of the title compound in quantitative yield.
The title compound:
MS calc.: 527.2402; MS found: 527.2405
According to this same methodology, but employing suitable substituted derivatives, the following compound was prepared:

4-({3-[(2,6-diethylphenyl)carbamoyl]-1-methyl-4,5-dihydro-1H-pyrazolo[4,3-h]quinazolin-8-yl}amino)-3-methylbenzoic acid MS calc.: 511.2452; MS found: 511.2466

Example 13

N-(2,6-Diethylphenyl)-8-[(4-{[2-(dimethylamino)ethyl]carbamoyl}-2-methoxyphenyl)amino]-1-methyl-4,5-dihydro-1H-pyrazolo[4,3-h]quinazoline-3-carboxamide A suspension of 4-({3-[(2,6-diethylphenyl)carbamoyl]-1-methyl-4,5-dihydro-1H-pyrazolo[4,3-h]quinazolin-8-yl}amino)-3-methoxybenzoic acid (80 mg, 0.152 mmol) in anhydrous dimethylformamide (1.5 mL) was treated with N-ethyl-N,N-diisopropylamine (1.05 mL, 0.60 mmol) and TBTU (60 mg, 0.182 mmol). The mixture was then treated with N,N-dimethylethylenediemine (0.025 mL, 0.228 mmol). The reaction was stirred at room temperature for 24 h. The reaction was diluted with water and the resulting precipitate was collected by filtration to afford the title compound (72 mg, 80% yield).
The title compound:
MS calc.: 597.3296; MS found: 597.3307
According to this same methodology, but employing suitable substituted derivatives, the following compounds were prepared:

8-[(4-carbamoyl-2-methoxyphenyl)amino]-N-(2,6-diethylphenyl)-1-methyl-4,5-dihydro-1H-pyrazolo[4,3-h]quinazoline-3-carboxamide MS calc.: 526.2561; MS found: 526.2567

N-(2,6-diethylphenyl)-8-({2-methoxy-4-[(2-methoxyethyl)carbamoyl]phenyl}amino)-1-methyl-4,5-dihydro-1H-pyrazolo[4,3-h]quinazoline-3-carboxamide MS calc.: 584.2980; MS found: 584.2974

N-(2,6-diethylphenyl)-8-[(4-{[4-(dimethylamino)piperidin-1-yl]carbonyl}-2-methoxyphenyl)amino]-1-methyl-4,5-dihydro-1H-pyrazolo[4,3-h]quinazoline-3-carboxamide MS calc.: 637.3609; MS found: 637.3604

N-(2,6-diethylphenyl)-8-[(2-methoxy-4-{[(2S)-2-(pyrrolidin-1-ylmethyl)pyrrolidin-1-yl]carbonyl}phenyl)amino]-1-methyl-4,5-dihydro-1H-pyrazolo[4,3-h]quinazoline-3-carboxamide MS calc.: 663.3766; MS found: 663.3762

N-(2,6-diethylphenyl)-8-[(2-methoxy-4-{[(2R)-2-(pyrrolidin-1-ylmethyl)pyrrolidin-1-yl]carbonyl}phenyl)amino]-1-methyl-4,5-dihydro-1H-pyrazolo[4,3-h]quinazoline-3-carboxamide MS calc.: 663.3766; MS found: 663.3774

N-(2,6-diethylphenyl)-8-({4-[(2-hydroxyethyl)carbamoyl]-2-methoxyphenyl}amino)-1-methyl-4,5-dihydro-1H-pyrazolo[4,3-h]quinazoline-3-carboxamide MS calc.: 570.2824; MS found: 570.2828

N-(2,6-diethylphenyl)-8-({2-methoxy-4-[(3-pyrrolidin-1-ylazetidin-1-yl)carbonyl]phenyl}amino)-1-methyl-4,5-dihydro-1H-pyrazolo[4,3-h]quinazoline-3-carboxamide MS calc.: 635.3453 MS found: 635.3459

N-(2,6-diethylphenyl)-8-{[2-methoxy-4-(3-pyrrolidin-1-ylazetidin-1-yl)phenyl]amino}-1-methyl-4,5-dihydro-1H-pyrazolo[4,3-h]quinazoline-3-carboxamide MS calc.: 607.3504; MS found: 607.3506

N-(2,6-diethylphenyl)-8-({2-methoxy-4-[(4-methyl-1,4-diazepan-1-yl)carbonyl]phenyl}amino)-1-methyl-4,5-dihydro-1H-pyrazolo[4,3-h]quinazoline-3-carboxamide MS calc.: 623.3453; MS found: 623.3461

N-(2,6-diethylphenyl)-8-({2-methoxy-4-[(4-methylpiperazin-1-yl)carbonyl]phenyl}amino)-1-methyl-4,5-dihydro-1H-pyrazolo[4,3-h]quinazoline-3-carboxamide MS calc.: 609.3296; MS found: 609.3309

N-(2,6-diethylphenyl)-8-[(2-methoxy-4-{[(1-methylpiperidin-4-yl)carbonyl]amino}phenyl)amino]-1-methyl-4,5-dihydro-1H-pyrazolo[4,3-h]quinazoline-3-carboxamide MS calc.: 623.3453; MS found: 623.3439

N-(2,6-diethylphenyl)-8-[(4-{[4-(dimethylamino)piperidin-1-yl]carbonyl}-2-methylphenyl)amino]-1-methyl-4,5-dihydro-1H-pyrazolo[4,3-h]quinazoline-3-carboxamide MS calc.: 621.366; MS found: 621.3659

N-(2,6-diethylphenyl)-8-[(4-{[2-(dimethylamino)ethyl]carbamoyl}-2-methylphenyl)amino]-1-methyl-4,5-dihydro-1H-pyrazolo[4,3-h]quinazoline-3-carboxamide MS calc.: 581.3347; MS found: 581.3347

N-(2,6-diethylphenyl)-8-[(4-{[4-(dimethylamino)butanoyl]amino}-2-methoxyphenyl)amino]-1-methyl-4,5-dihydro-1H-pyrazolo[4,3-h]quinazoline-3-carboxamide trifluoroacetate MS calc.: 611.3453; MS found: 611.3451

N-(2,6-diethylphenyl)-1-methyl-8-[(2-methyl-4-{[(2R)-2-(pyrrolidin-1-ylmethyl)pyrrolidin-1-yl]carbonyl}phenyl)amino]-4,5-dihydro-1H-pyrazolo[4,3-h]quinazoline-3-carboxamide MS calc.: 647.3817; MS found: 647.3823

N-(2,6-diethylphenyl)-1-methyl-8-({2-methyl-4-[(4-methyl-1,4-diazepan-111)carbonyl]phenyl}amino)-4,5-dihydro-1H-pyrazolo[4,3-h]quinazoline-3-carboxamide MS calc.: 607.3504; MS found: 607.3504

N-(2,6-diethylphenyl)-8-({2-methoxy-4-[(3-piperidin-1-ylpropanoyl)amino]phenyl}amino)-1-methyl-4,5-dihydro-1H-pyrazolo[4,3-h]quinazoline-3-carboxamide MS calc.: 637.3609; MS found: 637.3610

N-(2,6-diethylphenyl)-1-methyl-8-({2-methyl-4-[(4-pyrrolidin-1-ylpiperidin-1-yl)carbonyl]phenyl}amino)-4,5-dihydro-1H-pyrazolo[4,3-h]quinazoline-3-carboxamide MS calc.: 647.3817; MS found: 647.3817

Example 14

N-(2,6-Diethylphenyl)-1-methyl-8-({1-[(4-methylpiperazin-1-yl)carbonyl]piperidin-4-yl}amino)-4,5-dihydro-1H-pyrazolo[4,3-h]quinazoline-3-carboxamide To a solution of N-(2,6-diethylphenyl)-1-methyl-8-(piperidin-4-ylamino)-4,5-dihydro-1H-pyrazolo[4,3-h]quinazoline-3-carboxamide hydrochloride (40 mg, 0.075 mmol) in dichloromethane (1 mL) at 0° C., DIPEA (0.2 mL, 1.1 mmol), and 4-methylpiperazine-1-carbonyl chloride (17 mg, 0.09 mmol) were added. The mixture was then stirred at room temperature for 3 h. Solvent evaporated to dryness and the crude solid was purified by flash chromatography on silica gel (eluant: dichloromethane/methanol: 9/1) to 38 mg of the title compound (86% yield).

MS calc.: 586.3627; MS found: 586.3613

Example 15

8-[(1-Acryloylpiperidin-4-yl)amino]-N-(2,6-diethylphenyl)-1-methyl-4,5-dihydro-1H-pyrazolo[4,3-h]quinazoline-3-carboxamide To a solution of N-(2,6-diethylphenyl)-1-methyl-8-(piperidin-4-ylamino)-4,5-dihydro-1H-pyrazolo[4,3-h]quinazoline-3-carboxamide hydrochloride (40 mg, 0.075 mmol) in dichloromethane (1 mL) at 0° C., DIPEA (0.4 mL, 2.2 mmol), and 3-bromopropionyl chloride (0.023 mL, 0.226 mmol) were added. The mixture was then stirred at room temperature for 3 h. Solvent evaporated to dryness and the crude solid was purified by flash chromatography on silica gel (eluant: dichloromethane/methanol: 9/1) to 73 mg of the title compound. (75% yield)

MS calc.: 514.2924; MS found: 514.2925

Example 16

N-(2,6-Diethylphenyl)-1-methyl-8-{[1-(N-methyl-beta-alanyl)piperidin-4-yl]amino}-4,5-dihydro-1H-pyrazolo[4,3-h]quinazoline-3-carboxamide To a solution 8-[(1-acryloylpiperidin-4-yl)amino]-N-(2,6-diethylphenyl)-1-methyl-4,5-dihydro-1H-pyrazolo[4,3-h]quinazoline-3-carboxamide (30 mg, 0.058 mmol) in tetrahydrofurane (1 mL) in a sealed tube, methylamine (2M in tetrahydrofurane) (0.3 mL) was added. The mixture was then heated at 60° C. for 2 h. Solvent evaporated to dryness and the crude solid was purified by flash chromatography on silica gel (eluant: dichloromethane/methanol/30% ammonium hydroxide: 8/2/0.2) to 27 mg of the title compound (77% yield).

MS calc.: 545.3345; MS found: 545.3347

According to this same methodology, but employing suitable substituted derivatives, the following compound was prepared:

N-(2,6-diethylphenyl)-8-{[1-(N,N-dimethyl-beta-alanyl)piperidin-4-yl]amino}-1-methyl-4,5-dihydro-1H-pyrazolo[4,3-h]quinazoline-3-carboxamide MS calc.: 559.3493; MS found: 559.3504

Example 17

N-(2,6-Diethylphenyl)-8-[(2-iodophenyl)amino]-1-methyl-4,5-dihydro-1H-pyrazolo[4,3-h]quinazoline-3-carboxamide To a solution 8-[(2-bromophenyl)amino]-N-(2,6-diethylphenyl)-1-methyl-4,5-dihydro-1H-pyrazolo[4,3-h]quinazoline-3-carboxamide (68 mg, 0.129 mmol) in dioxane (0.5 mL) in a sealed tube, NaI (38 mg, 0.257 mmol), CuI (1.2 mg, 0.006 mmol), iodine (74 mg, 0.129 mmol) and trans-N,N'-dimethylcycloesane-1,2-diammine were added. The mixture was then heated at 150° C. for 12 h. Solvent evaporated to dryness and the crude solid was purified by flash chromatography on silica gel (eluant: dichloromethane/methanol: 8/2/) to 35 mg of the title compound (50% yield).

MS calc.: 579.1364; MS found: 579.1370

Preparation 7

4-(4-Methyl-piperazin-1-yl)-2-trifluoromethoxy-phenylamine

Tris(dibenzilideneacetone)dipalladium, $Pd_2(dba)_3$ (1.1 g, 1.2 mmol), 2-dicyclohexylphosphino-2'-(N,N-dimethylamino)-biphenyl (0.94 g, 2.4 mmol), 5-bromo-2-trifluoromethoxy-phenylamine (30.7 g, 120 mmol) in THF (50 mL) were charged in a round-bottom flask flushed with argon. The flask was evacuated and backfilled with argon. $LiN(TMS)_2$ solution (1M in THF, 288 mL) and N-methylpiperazine (26.7 mL, 194 mmol) were added and the reaction refluxed for 1 h. The reaction mixture was then allowed to cool to room temperature and filtered through a pad of celite. The organic phase was concentrated, the residue dissolved in DCM (200 mL) and washed with water (1×100 mL). The organic phases were dried over anhydrous $Na_2SO_4$, the solvent evaporated in vacuo and the crude solid was purified by flash chromatography on silica gel (eluant: DCM/EtOH 90/10) to afford 23 g of 4-(4-methyl-piperazin-1-yl)-2-trifluoromethoxy-phenylamine (70% yield) as a light brown powder.

MS calc: 276.1318; MS found: 276.1320

According to this same methodology, but employing suitable substituted derivatives, the following compounds were prepared:

4-(4-Methyl-piperazin-1-yl)-2-methoxy-phenylamine

MS calc.: 222.1601; MS found: 222.1596

5-(4-Methyl-piperazin-1-yl)-2-trifluoromethoxy-phenylamine

MS calc.: 276.1318; MS found: 276.1324

5-(4-Methyl-piperazin-1-yl)-2-methoxy-phenylamine

MS calc.: 222.1601; MS found: 222.1609

Preparation 8

N-[4-(4-Methyl-piperazin-1-yl)-2-trifluoromethoxy-phenyl]-guanidine

To a solution of 4-(4-methyl-piperazin-1-yl)-2-trifluoromethoxy-phenylamine (275 mg, 1 mmol) in HCl 6N (1 mL), cyanamide (336 mg, 8.0 mmol) was added and the reaction was stirred at 60° C. for 1 h. The mixture was cooled down to room temperature, diluted with water (3 mL), extracted with DCM (10 mL). NaOH 2N was added to pH>11. The aqueous phase was extracted with $Et_2O$ (3×10 mL), dried over sodium sulfate and concentrated. The residue was crystallized from diethyl ether to give the title compound (240 mg, 76% yield) as a white solid.

MS calc: 318.1536; MS found: 318.1526

According to this same methodology, but employing suitable substituted derivatives, the following compounds were prepared:

N-[4-(4-Methyl-piperazin-1-yl)-2-methoxy-phenyl]-guanidine

MS calc.: 264.1819; MS found: 264.1817

N-[4-(tert-butylcarboxamido)-2-methoxy-phenyl]-guanidine

MS calc.: 266.1499; MS found: 266.1491

Preparation 9

4-Iodo-3-methoxybenzoic acid

To a solution of 4-amino-3-methoxybenzoic acid (5 mg, 29.9 mmol) in $H_2O$ (30 mL) and HCl 37% (30 mL) at 0° C., was slowly added a solution of $NaNO_2$ (2.27 g, 32.9 mmol) in $H_2O$ (10 mL). The solution obtained was then stirred for 20 minutes and then added at 0° C. to a solution of KI (34.75 g, 7 mmol) in $H_2O$ (10 mL). The mixture was stirred for 3 hours. After cooling in an ice-water bath, the solid was filtered off. The filtrate was diluted with ethyla actetae, washed with 10% sodium methabisulphite, dried over anhydrous $Na_2SO_4$ and concentrated to give 3.7 g of the title compound (46% yield).

$^1$H NMR (400 MHz, DMSO-$d_6$) δ ppm: 3.90 (s, 3H) 7.31 (dd, J=1.71 Hz and J 8.05 Hz, 1H), 7.43 (d, J=1.71 Hz, 1H), 7.92 (d, J=8.05 Hz, 1H), 13.15 (b.s., 1H).

Preparation 10 tert-Butyloxy 4-Iodo-3-methoxybenzoate

To a solution of 4-iodo-3-methoxybenzoic acid (2.7 g, 11 mmol) in dichloromethane (40 mL) and tert-butanol (10 mL), di-tert-butyldicarbonate (4.2 g, 19.2 mmol) and a catalytic amount of 4-dimethylaminopyridine were added. The mixture was heated at reflux for 24 hours. The mixture was cooled down to room temperature, and the solvent evaporated to dryness. The residue was crystallized from diethyl ether to give the title compound (2.3 g, 62% yield) as a white solid.

$^1$H NMR (400 MHz, DMSO-$d_6$) δ ppm: 1.55 (s, 9H) 3.89 (s, 3H) 7.27 (dd, J=1.71 Hz and J 8.05 Hz, 1H), 7.38 (d, J=1.71 Hz, 1H), 7.92 (d, J=8.05 Hz, 1H).

According to this same methodology, but employing suitable substituted derivatives, the following compounds were prepared:

4-[Iodo-3-(trifluoromethoxy)phenyl]-4-methylpiperazine

MS calc.: 387.0176; MS found: 387.0182

4-Iodo-N-(1-methylpiperidin-yl)-3-(trifluoromethoxy)benzamide

MS calc.: 429.0282; MS found: 429.0289

Preparation 11

4-Iodo-3-methoxy-N-(1-methylpiperidin-yl)benzamide

A solution of tert-butyloxy 4-iodo-3-methoxybenzoate (250 mg, 0.90 mmol) in anhydrous dimethylformamide (8 mL) was treated with N-ethyl-N,N-diisopropylamine (0.63 mL, 3.6 mmol) and TBTU (404 mg, 1.26 mmol). The mixture was then treated with 1-methylpiperidin-4-amine (0.160 mL, 1.26 mmol). The reaction mixture was stirred at room temperature for 24 h. The reaction was diluted with water and the resulting precipitate was collected by filtration to afford the title compound (250 mg, 71% yield).
MS calc.: 375.0564; MS found: 375.0576.

Example 18

N-(2,6-diethylphenyl)-8-{[4-(hydroxymethyl)-2-methoxyphenyl]amino}-1-methyl-4,5-dihydro-1H-pyrazolo[4,3-h]quinazoline-3-carboxamide To a solution of 8-{[4-({[tert-butyl(dimethyl)silyl]oxy}methyl)-2-methoxyphenyl]amino}-N-(2,6-diethylphenyl)-1-methyl-4,5-dihydro-1H-pyrazolo[4,3-h]quinazoline-3-carboxamide (300 mg, 0.48 mmol) in 6 ml of dry THF, 800 µl of commercial TBAF solution in THF were added. The mixture was stirred at room temperature for 1 h and the to solvent removed in vacuo. The crude was washed with water, extracted with ethyl acetate, dried on anhydrous $Na_2SO_4$ and evaporated to dryness affording the title compound in 85% yield.
MS calc.: 513.2609; MS found: 513.2601

Example 19

N-(2,6-diethylphenyl)-8-[(4-formyl-2-methoxyphenyl)amino]-1-methyl-4,5-dihydro-1H-pyrazolo[4,3-h]quinazoline-3-carboxamide To a solution of N-(2,6-diethylphenyl)-8-{[4-(hydroxymethyl)-2-methoxyphenyl]amino}-1-methyl-4,5-dihydro-1H-pyrazolo[4,3-h]quinazoline-3-carboxamide (50 mg, 0.097 mmol) in 1 ml of dry DCM, $MnO_2$ (68 mg, 0.78 mmol) was added. The mixture was stirred at room temperature for 5 h, $MnO_2$ filtered off and the solvent removed in vacuo affording the title compound in 80% yield.

Example 20

N-(2,6-diethylphenyl)-8-({2-methoxy-4-[(4-methylpiperazin-1-yl)methyl]phenyl}amino)-1-methyl-4,5-dihydro-1H-pyrazolo[4,3-h]quinazoline-3-carboxamide To a solution of N-(2,6-diethylphenyl)-8-[(4-formyl-2-methoxyphenyl)amino]-1-methyl-4,5-dihydro-1H-pyrazolo[4,3-h]quinazoline-3-carboxamide (50 mg, 0.097 mmol) and N-methyl-piperazine (49 mg, 0.49 mmol) in 1 ml of dry DCM, $NaBH(AcO)_3$ (123 mg, 0.58 mmol) and AcOH (25 µl) were added. The mixture was stirred at room temperature for 3 h, washed with aqueous $NaHCO_3$, dried over $Na_2SO_4$ and evaporated to dryness. The crude was purified by flash column chromatography (DCM/MeOH 9:1) affording the title compound in 75% yield.
MS calc.: 595.3504; MS found: 595.3498

Example 21

8-[(4-amino-2-methoxyphenyl)amino]-N-(2,6-diethylphenyl)-1-methyl-4,5-dihydro-1H-pyrazolo[4,3-h]quinazoline-3-carboxamide To a suspension of N-(2,6-diethylphenyl)-8-[(2-methoxy-4-nitrophenyl)amino]-1-methyl-4,5-dihydro-1H-pyrazolo[4,3-h]quinazoline-3-carboxamide (1.4 g, 2.656 mmol) in 27 ml of dioxane, zinc (695 mg, 10.624 mmol) and ammonium chloride (1.4 g, 26.56 mmol) in 2.7 ml of water were added and heated at 100° C. under stirring for 8 h. The mixture was cooled, the insoluble material filtered off and washed with ethyl acetate, the combined organic solutions are washed with aqueous citric acid solution, dried on $Na_2SO_4$ and evaporated in vacuo leaving a pink foam as crude title product that has been used without any further purification.
MS calc.: 498.2612; MS found: 498.2600

Example 21

N-(2,6-diethylphenyl)-8-({2-methoxy-4-[(1-methylpiperidin-4-yl)amino]phenyl}amino)-1-methyl-4,5-dihydro-1H-pyrazolo[4,3-h]quinazoline-3-carboxamide To a stirred solution of 8-[(4-amino-2-methoxyphenyl)amino]-N-(2,6-diethylphenyl)-1-methyl-4,5-dihydro-1H-pyrazolo[4,3-h]quinazoline-3-carboxamide (80 mg, 0.158 mmol) in 1.5 ml of $CH_2Cl_2$ under argon atmosphere, tetrahydro-4H-pyran-4-one (20 mg, 0.198 mmol), TFA (0.428 mmol; 2.7 eq) and tetramethylammonium triacetoxyborohydride (63 mg, 0.238 mmol) were added. The mixture was stirred at room temperature for 1 h. Saturated aqueous $NaHCO_3$ was added and the organic layer separated, dried on anhydrous $Na_2SO_4$ and evaporated to dryness. The residue was purified by flash chromatography (97.5/2.5 $CH_2Cl_2$/$CH_3OH$) giving the to desired product as a brown foam in a 34% yield.
MS calc.: 582.3187; MS found: 582.3195
According to this same methodology, but employing suitable substituted derivatives, the following compounds were prepared:

N-(2,6-diethylphenyl)-8-({2-methoxy-4-[(1-methylpiperidin-4-yl)amino]phenyl}amino)-1-methyl-4,5-dihydro-1H-pyrazolo[4,3-h]quinazoline-3-carboxamide MS calc.: 595.3504; MS found: 595.3505

N-(2,6-diethylphenyl)-8-({4-[(4-hydroxycyclohexyl)amino]-2-methoxyphenyl}amino)-1-methyl-4,5-dihydro-1H-pyrazolo[4,3-h]quinazoline-3-carboxamide MS calc.: 596.3344; MS found: 596.3342

8-{[4-(1-azabicyclo[2.2.2]oct-3-ylamino)-2-methoxyphenyl]amino}-N-(2,6-diethylphenyl)-1-methyl-4,5-dihydro-1H-pyrazolo[4,3-h]quinazoline-3-carboxamide MS calc.: 607.3504; MS found: 607.3493

Preparation 12

N-(2,6-diethylphenyl)-8-iodo-1-methyl-4,5-dihydro-1H-pyrazolo[4,3-h]quinazoline-3-carboxamide Ethyl 8-iodo-1-methyl-4,5-dihydro-1H-pyrazolo[4,3-h]quinazoline-3-carboxylate (4.0 g, 10.4 mmol) prepared as described in WO2004/104007 was dissolved in anhydrous ethanol (150 mL) and treated with potassium hydroxide (5.83 g, 104 mmol.) at RT for 24 hour. The white precipitate formed during the reaction was collected by filtration. The solid was then suspended in anhydrous dimethylformamide (5.0 mL) and treated with N-ethyl-N,N-diisopropylamine (10 ml) and O-(Benzotriazol-1-yl)-N,N,N',N'-tetramethyluronium tetrafluoroborate (TBTU) (4.5 g, 14.1 mmol). The mixture was then treated with 2,6-diethylaniline (2.3 ml, 14.1 mmol) and stirred at room temperature overnight. The solvent was removed under reduced pressure and the crude was purified by column chromatography to afford the title compound.

MS calc.: 487.3450; MS found: 487.3448.

According to this same methodology, but employing suitable substituted derivatives, the following compound was prepared:

8-Amino-N-(2,6-diethylphenyl)-1-methyl-4,5-dihydro-1H-pyrazolo[4,3-h]quinazoline-3-carboxamide MS calc.: 377.2085; MS found: 377.2097

Example 22

8-[(trans-4-aminocyclohexyl)amino]-N-(2,6-diethylphenyl)-1-methyl-4,5-dihydro-1H-pyrazolo[4,3-h]quinazoline-3-carboxamide N-(2,6-diethylphenyl)-8-iodo-1-methyl-4,5-dihydro-1H-pyrazolo[4,3-h]quinazoline-3-carboxamide (500 mg, 1.01 mmol) was dissolved in CH3CN (3 ml) and treated with trans-1,4-diaminecyclohexane (346 mg, 303 mmol). The mixture was heated at 110° C. for 10 minutes under microwave irradiation. The solvent was removed under reduced pressure and the crude was purified by column chromatography to afford the title compound.

MS calc.: 474.2976; MS found: 474.2974

According to this same methodology, but employing suitable substituted derivatives, the following compound was prepared:

tert-butyl 4-({3-[(2,6-diethylphenyl)carbamoyl]-1-methyl-4,5-dihydro-1H-pyrazolo[4,3-h]quinazolin-8-yl}amino)-3,3-dimethylpiperidine-1-carboxylate MS calc.: 588.3657; MS found: 588.3661

Preparation 13

8-Amino-N-(2,6-diethylphenyl)-1-methyl-4,5-dihydro-1H-pyrazolo[4,3-h]quinazoline-3-carboxamide Sodium hexamethyldisilazide (NaHMDS) in THF (1.0 M, 11.0 mL, 11.0 mmol) was added over 30 min to a solution of 2,6-diethylaniline (1.2 mL, 8.32 mmol) and ethyl 8-amino-1-methyl-4,5-dihydro-1H-pyrazolo[4,3-h]quinazoline-3-carboxylate (0.760 g, 2.77 mmol) in THF (30 mL) at 0° C. The resulting brown solution was stirred at 0° C. for 10 min and allowed to warm to room temperature over a period of 30 min. After stirring at room temperature for 3 h, the reaction was quenched by the addiction of saturated acqueous $NH_4Cl$ (10 mL). The reaction was partitioned between ethyl acetate (50 mL) and water (50 mL). The acqueos layer was extracted with ethyl acetate (2×30 mL). The combined organic solution was washed with brine (50 mL), dried over $Na_2SO_4$, filtered and evaporated to dryness, the crude solid was purified by flash chromatography on silica gel (eluant: dichloromethane/methanol 95/5) to afford 0.830 g (80% yield) of the title compound.

MS calc.: 377.2085; MS found: 377.2097

Example 23

According to this same methodology described in Preparation 13 above, but employing suitable derivatives as starting materials, the following final compounds were analogously prepared:

8-[(4-bromo-2-methoxyphenyl)amino]-N-(2,6-diethylphenyl)-1-methyl-4,5-dihydro-1H-pyrazolo[4,3-h]quinazoline-3-carboxamide MS calc.: 561.1608; MS found: 561.1591

N-(2,6-Diethylphenyl)-8-{[2-methoxy-4-(4-methylpiperazin-1-yl)phenyl]amino}-1-methyl-4,5-dihydro-1H-pyrazolo[4,3-h]quinazoline-3-carboxamide MS calc.: 581.3347; MS found: 581.3344

The invention claimed is:

1. A compound of formula (I):

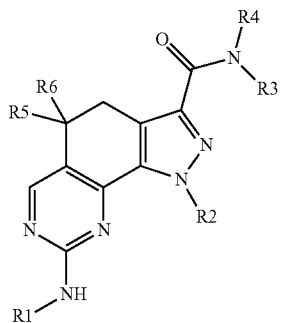

(I)

wherein:

R1 is an ortho-substituted-aryl group or a heterocyclyl or $C_3$-$C_7$ cycloalkyl group;

R2 is hydrogen atom or a straight or branched $C_1$-$C_6$ alkyl, $C_2$-$C_6$ alkenyl, $C_2$-$C_6$ alkynyl, $C_3$-$C_7$ cycloalkyl or heterocyclyl group;

R3 is aryl;

R4 is hydrogen atom, hydroxyl or $C_1$-$C_6$ alkyl group, which group may be optionally cyclized together with one of the atom of the group which R3 may represent so as to form a fused $C_4$-$C_7$ cyclic group;

R5 and R6: are each independently hydrogen atom, $C_1$-$C_6$ alkyl, or are optionally cyclized together with the carbon atom to which they are bonded so as to form a $C_3$-$C_7$ cycloalkyl group;

wherein the groups ortho-substituted-aryl, aryl, heterocyclyl, $C_3$-$C_7$ cycloalkyl, $C_4$-$C_7$ cycloalkyl, $C_1$-$C_6$ alkyl, $C_2$-$C_6$ alkenyl and $C_2$-$C_6$ alkynyl may be optionally (further) substituted;

and the pharmaceutically acceptable salts thereof.

2. A compound of the formula (I) according to claim 1 characterized in that R1 is an ortho-substituted-aryl of the formula A, B or C:

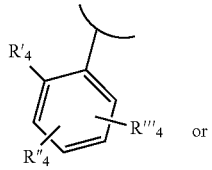

A

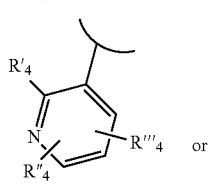

B

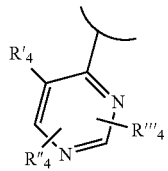

C wherein $R'_4$ is halogen atom, nitro, cyano, $C_1$-$C_6$ alkyl, polyfluorinated alkyl, polyfluorinated alkoxy, alkenyl, alkynyl, hydroxyalkyl, aryl, arylalkyl, heterocyclyl, $C_3$-$C_7$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclyloxycarbonyl, amino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl, alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate or alkylphosphonate; $R''_4$ and $R'''_4$ are independently hydrogen or one of the above meaning for $R'_4$; and the pharmaceutically acceptable salts thereof.

3. A compound of the formula (I) according to claim 1, having the formula (Ia):

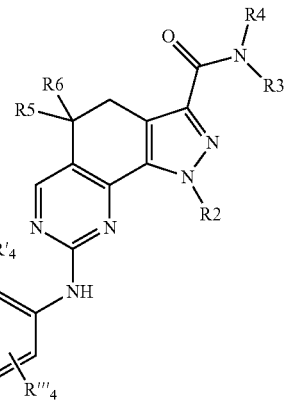

Ia wherein R'₄, is halogen atom, nitro, cyano, $C_1$-$C_6$ alkyl, polyfluorinated alkyl, polyfluorinated alkoxy, alkenyl, alkynyl, hydroxyalkyl, aryl, arylalkyl, heterocyclyl, $C_3$-$C_7$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclyloxycarbonyl, amino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl, alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate or alkylphosphonate; R"₄ and R"'₄ are independently hydrogen or one of the above meaning for R'₄;

R2 is an optionally substituted straight or branched $C_1$-$C_6$ alkyl or $C_2$-$C_6$ alkenyl group;

R3 is an optionally substituted aryl group;

R4 is hydrogen atom or a $C_1$-$C_6$ alkyl group which may be optionally cyclized together with one of the atom of the group which R3 represents so as to form a fused $C_4$-$C_7$ cyclic group and R5 and R6 are as defined in claim 1, or a pharmaceutically acceptable salt thereof.

4. A compound of the formula (I) according to claim 1, having the formula (Ia'):

![Structure Ia']

wherein R'₄, is halogen atom, nitro, cyano, $C_1$-$C_6$ alkyl, polyfluorinated alkyl, polyfluorinated alkoxy, alkenyl, alkynyl, hydroxyalkyl, aryl, arylalkyl, heterocyclyl, $C_3$-$C_7$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclyloxycarbonyl, amino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl, alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate or alkylphosphonate; R"₄ and R"'₄ are independently hydrogen or one of the above meaning for R'₄ R"₄ and R"'₄ are as defined in claim 2;

R2 is an optionally substituted straight or branched $C_1$-$C_6$ alkyl or $C_2$-$C_6$ alkenyl group;

R3 is aryl, heterocyclyl or $C_3$-$C_7$ cycloalkyl group;

R4 is hydrogen atom or a $C_1$-$C_6$ alkyl group which may be optionally cyclized together with one of the atom of the group which R3 represents so as to form a fused $C_4$-$C_7$ cyclic group and R5 and R6 are hydrogen atom or a methyl group, or a pharmaceutically acceptable salt thereof.

5. A compound of the formula (I) according to claim 1 characterized in that R1 is a heterocyclyl or $C_5$-$C_7$ cycloalkyl group of the formula D:

wherein Z is carbon or nitrogen atom, n is 1, 2 or 3; R'₁ is hydrogen atom, $C_1$-$C_6$ alkyl, polyfluorinated alkyl, polyfluorinated alkoxy, alkenyl, alkynyl, hydroxyalkyl, aryl, arylalkyl, heterocyclyl, $C_3$-$C_7$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclyloxycarbonyl, amino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl, alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate; and R'₂ and R'₃ are each independently hydrogen atom or a $C_1$-$C_3$ alkyl optionally cyclized together with the carbon atom to which they are bonded so as to form a cyclopropyl group.

6. A compound of the formula (I) according to claim 1, having the formula (Ib):

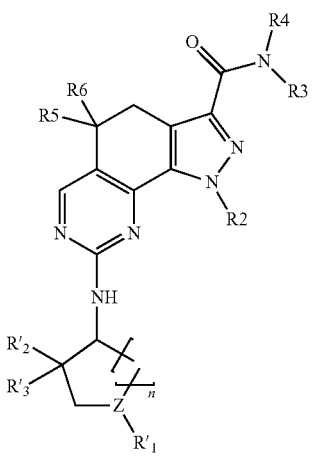

Ib wherein Z is a carbon or nitrogen atom, n is 1 or 2; R'$_1$ is hydrogen atom, $C_1$-$C_6$ alkyl, polyfluorinated alkyl, polyfluorinated alkoxy, alkenyl, alkynyl, hydroxyalkyl, aryl, arylalkyl, heterocyclyl, $C_3$-$C_7$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclyloxycarbonyl, amino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl, alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate; and R'$_2$ and R'$_3$ are independently hydrogen atom or $C_1$-$C_2$ alkyl group;

R2 is an optionally substituted straight or branched $C_1$-$C_6$ alkyl or $C_2$-$C_6$ alkenyl group;

R3 is an optionally substituted aryl group;

R4 is hydrogen atom or a $C_1$-$C_6$ alkyl group which may be optionally cyclized together with one of the atom of the aryl group which R3 represents so as to form a fused $C_4$-$C_7$ cyclic group and R5 and R6 are as defined in claim 1, or a pharmaceutically acceptable salt thereof.

7. A compound of the formula (I) according to claim 1, having the formula (Ib'):

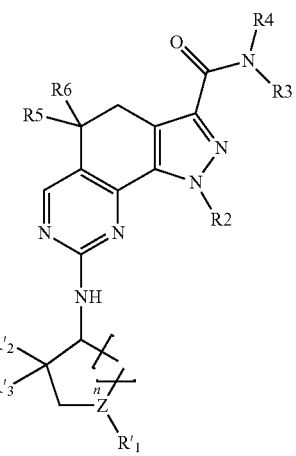

Ib' wherein Z is a carbon or nitrogen atom, n is 1 or 2, R'$_1$ is hydrogen atom, $C_1$-$C_6$ alkyl, polyfluorinated alkyl, polyfluorinated alkoxy, alkenyl, alkynyl, hydroxyalkyl, aryl, arylalkyl, heterocyclyl, $C_3$-$C_7$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclyloxycarbonyl, amino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl, alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate, R'$_2$ and R'$_3$ are independently hydrogen atom or $C_1$-$C_2$ alkyl group;

R2 is an optionally substituted straight or branched $C_1$-$C_6$ alkyl or $C_2$-$C_6$ alkenyl group;

R3 is an optionally substituted aryl group;

R4 is hydrogen atom or $C_1$-$C_6$ alkyl group which may be optionally cyclized together with one of the atom of the aryl group which R3 represents so as to form a fused $C_4$-$C_7$ cyclic group and R5 and R6 are hydrogen atom or a methyl group, or a pharmaceutically acceptable salt thereof.

8. A compound of the formula (I) according to claim 1, or a pharmaceutically acceptable salt thereof, which is one of the compounds listed below:

1) N-(2,6-diethylphenyl)-1-methyl-8-({4-[(1-methylpiperidin-4-yl)carbamoyl]-2-(trifluoromethoxy) phenyl}amino)-4,5-dihydro-1H-pyrazolo[4,3-h] quinazoline-3-carboxamide;

2) N-(2,6-diethylphenyl)-8-({2-methoxy-4-[(1-methylpiperidin-4-yl)carbamoyl]phenyl}amino)-1-methyl-4,5-dihydro-1H-pyrazolo[4,3-h]quinazoline-3-carboxamide;

3) N-(2,6-diethylphenyl)-1-methyl-8-{[4-(4-methylpiperazin-1-yl)-2-(trifluoromethoxy)phenyl]amino}-4,5-dihydro-1H-pyrazolo[4,3-h]quinazoline-3-carboxamide;
4) 8-[(4-carbamoyl-2-methylphenyl)amino]-N-(2,6-diethylphenyl)-1-methyl-4,5-dihydro-1H-pyrazolo[4,3-h]quinazoline-3-carboxamide;
5) N-(2,6-diethylphenyl)-8-{[2-methoxy-4-(4-methylpiperazin-1-yl)phenyl]amino}-1-methyl-4,5-dihydro-1H-pyrazolo[4,3-h]quinazoline-3-carboxamide;
6) 8-[(4-bromo-2-methoxyphenyl)amino]-N-(2,6-diethylphenyl)-1-methyl-4,5-dihydro-1H-pyrazolo[4,3-h]quinazoline-3-carboxamide;
7) N-(2,6-diethylphenyl)-8-[(4-{[3-(dimethylamino)propyl](methyl)amino}-2-methoxyphenyl)amino]-1-methyl-4,5-dihydro-1H-pyrazolo[4,3-h]quinazoline-3-carboxamide;
8) N-(2,6-diethylphenyl)-8-({4-[4-(dimethylamino)piperidin-1-yl]-2-methoxyphenyl}amino)-1-methyl-4,5-dihydro-1H-pyrazolo[4,3-h]quinazoline-3-carboxamide;
9) N-(2,6-diethylphenyl)-8-{[2-methoxy-4-(4-methyl-1,4-diazepan-1-yl)phenyl]amino}-1-methyl-4,5-dihydro-1H-pyrazolo[4,3-h]quinazoline-3-carboxamide;
10) tert-butyl 4-({3-[(2,6-diethylphenyl)carbamoyl]-1-methyl-4,5-dihydro-1H-pyrazolo[4,3-h]quinazolin-8-yl}amino)-3-methoxybenzoate;
11) 4-({3-[(2,6-diethylphenyl)carbamoyl]-1-methyl-4,5-dihydro-1H-pyrazolo[4,3-h]quinazolin-8-yl}amino)-3-methoxybenzoic acid;
12) N-(2,6-diethylphenyl)-8-[(4-{[2-(dimethylamino)ethyl](methyl)amino}-2-methoxyphenyl)amino]-1-methyl-4,5-dihydro-1H-pyrazolo[4,3-h]quinazoline-3-carboxamide;
13) 8-[(4-carbamoyl-2-methoxyphenyl)amino]-N-(2,6-diethylphenyl)-1-methyl-4,5-dihydro-1H-pyrazolo[4,3-h]quinazoline-3-carboxamide;
14) N-(2,6-diethylphenyl)-8-[(4-{[2-(dimethylamino)ethyl]carbamoyl}-2-methoxyphenyl)amino]-1-methyl-4,5-dihydro-1H-pyrazolo[4,3-h]quinazoline-3-carboxamide;
15) 1-methyl-8-({4-[(1-methylpiperidin-4-yl)carbamoyl]-2-(trifluoromethoxy)phenyl}amino)-N-phenyl-4,5-dihydro-1H-pyrazolo[4,3-h]quinazoline-3-carboxamide;
16) N-(2-ethylphenyl)-1-methyl-8-({4-[(1-methylpiperidin-4-yl)carbamoyl]-2-(trifluoromethoxy)phenyl}amino)-4,5-dihydro-1H-pyrazolo[4,3-h]quinazoline-3-carboxamide;
17) N-(2,6-diethylphenyl)-8-[(2-methoxy-4-nitrophenyl)amino]-1-methyl-4,5-dihydro-1H-pyrazolo[4,3-h]quinazoline-3-carboxamide;
18) N-(2,6-diethylphenyl)-8-({2-methoxy-4-[(2-methoxyethyl)carbamoyl]phenyl}amino)-18) 1-methyl-4,5-dihydro-1H-pyrazolo[4,3-h]quinazoline-3-carboxamide;
19) N-(2,6-diethylphenyl)-8-[(4-{[4-(dimethylamino)piperidin-1-yl]carbonyl}-2-methoxyphenyl)amino]-1-methyl-4,5-dihydro-1H-pyrazolo[4,3-h]quinazoline-3-carboxamide;
20) N-(2,6-diethylphenyl)-8-[(2-methoxy-4-{[(2S)-2-(pyrrolidin-1-ylmethyl)pyrrolidin-1-yl]carbonyl}phenyl)amino]-1-methyl-4,5-dihydro-1H-pyrazolo[4,3-h]quinazoline-3-carboxamide;
21) N-(2,6-diethylphenyl)-8-[(2-methoxy-4-{[(2R)-2-(pyrrolidin-1-ylmethyl)pyrrolidin-1-yl]carbonyl}phenyl)amino]-1-methyl-4,5-dihydro-1H-pyrazolo[4,3-h]quinazoline-3-carboxamide;
22) N-(2-ethylphenyl)-8-{[2-methoxy-4-(4-methylpiperazin-1-yl)phenyl]amino}-1-methyl-4,5-dihydro-1H-pyrazolo[4,3-h]quinazoline-3-carboxamide;
23) N-(2,3-dihydro-1H-inden-5-yl)-8-{[2-methoxy-4-(4-methylpiperazin-1-yl)phenyl]amino}-1-methyl-4,5-dihydro-1H-pyrazolo[4,3-h]quinazoline-3-carboxamide;
24) 8-{[2-methoxy-4-(4-methylpiperazin-1-yl)phenyl]amino}-1-methyl-N-(5,6,7,8-tetrahydronaphthalen-1-yl)-4,5-dihydro-1H-pyrazolo[4,3-h]quinazoline-3-carboxamide;
25) 3-(2,3-dihydro-1H-indol-1-ylcarbonyl)-N-[2-methoxy-4-(4-methylpiperazin-1-yl)phenyl]-1-methyl-4,5-dihydro-1H-pyrazolo[4,3-h]quinazolin-8-amine;
26) N-(2,6-dimethylphenyl)-8-{[2-methoxy-4-(4-methylpiperazin-1-yl)phenyl]amino}-1-methyl-4,5-dihydro-1H-pyrazolo[4,3-h]quinazoline-3-carboxamide;
27) N-(2-ethyl-6-methylphenyl)-8-{[2-methoxy-4-(4-methylpiperazin-1-yl)phenyl]amino}-1-methyl-4,5-dihydro-1H-pyrazolo[4,3-h]quinazoline-3-carboxamide;
28) 8-{[2-methoxy-4-(4-methylpiperazin-1-yl)phenyl]amino}-N-(2-methoxyphenyl)-1-methyl-4,5-dihydro-1H-pyrazolo[4,3-h]quinazoline-3-carboxamide;
29) N-1,3-benzothiazol-5-yl-8-{[2-methoxy-4-(4-methylpiperazin-1-yl)phenyl]amino}-1-methyl-4,5-dihydro-1H-pyrazolo[4,3-h]quinazoline-3-carboxamide;
30) N-(2-chloro-6-methylphenyl)-8-{[2-methoxy-4-(4-methylpiperazin-1-yl)phenyl]amino}-1-methyl-4,5-dihydro-1H-pyrazolo[4,3-h]quinazoline-3-carboxamide;
31) N-[2,6-bis(1-methylethyl)phenyl]-8-{[2-methoxy-4-(4-methylpiperazin-1-yl)phenyl]amino}-1-methyl-4,5-dihydro-1H-pyrazolo[4,3-h]quinazoline-3-carboxamide;
32) N-(2,6-diethylphenyl)-8-({4-[(2-hydroxyethyl)carbamoyl]-2-methoxyphenyl}amino)-1-methyl-4,5-dihydro-1H-pyrazolo[4,3-h]quinazoline-3-carboxamide;
33) 8-{[2-cyano-4-(4-methylpiperazin-1-yl)phenyl]amino}-N-(2,6-diethylphenyl)-1-methyl-4,5-dihydro-1H-pyrazolo[4,3-h]quinazoline-3-carboxamide;
34) 8-{[2-cyano-4-(4-methyl-1,4-diazepan-1-yl)phenyl]amino}-N-(2,6-diethylphenyl)-1-methyl-4,5-dihydro-1H-pyrazolo[4,3-h]quinazoline-3-carboxamide;
35) 8-[(2-chlorophenyl)amino]-N-(2,6-diethylphenyl)-1-methyl-4,5-dihydro-1H-pyrazolo[4,3-h]quinazoline-3-carboxamide;
36) 8-[(4-bromo-2-cyanophenyl)amino]-N-(2,6-diethylphenyl)-1-methyl-4,5-dihydro-1H-pyrazolo[4,3-h]quinazoline-3-carboxamide;
37) 8-[(2-bromophenyl)amino]-N-(2,6-diethylphenyl)-1-methyl-4,5-dihydro-1H-pyrazolo[4,3-h]quinazoline-3-carboxamide;
38) N-(2,6-diethylphenyl)-8-[(2-methoxyphenyl)amino]-1-methyl-4,5-dihydro-1H-pyrazolo[4,3-h]quinazoline-3-carboxamide;
39) N-(2,6-diethylphenyl)-8-({2-methoxy-4-[(3-pyrrolidin-1-ylazetidin-1-yl)carbonyl]phenyl}amino)-1-methyl-4,5-dihydro-1H-pyrazolo[4,3-h]quinazoline-3-carboxamide;
40) N-(2,6-diethylphenyl)-8-{[2-methoxy-4-(3-pyrrolidin-1-ylazetidin-1-yl)phenyl]amino}-1-methyl-4,5-dihydro-1H-pyrazolo[4,3-h]quinazoline-3-carboxamide;
41) N-(2,6-dimethylphenyl)-8-{[2-methoxy-4-(4-methylpiperazin-1-yl)phenyl]amino}-1,5,5-trimethyl-4,5-dihydro-1H-pyrazolo[4,3-h]quinazoline-3-carboxamide;

42) N-(2,6-diethylphenyl)-8-({2-methoxy-4-[(4-methyl-1,4-diazepan-1-yl)carbonyl]phenyl}amino)-1-methyl-4,5-dihydro-1H-pyrazolo[4,3-h]quinazoline-3-carboxamide;

43) N-(2,6-diethylphenyl)-8-({2-methoxy-4-[(2-methoxyethyl)amino]phenyl}amino)-1-methyl-4,5-dihydro-1H-pyrazolo[4,3-h]quinazoline-3-carboxamide;

44) 8-[(4-bromo-2-methoxyphenyl)amino]-N-(2,6-diethylphenyl)-1,5,5-trimethyl-4,5-dihydro-1H-pyrazolo[4,3-h]quinazoline-3-carboxamide;

45) N-(2,6-diethylphenyl)-8-[(2-iodophenyl)amino]-1-methyl-4,5-dihydro-1H-pyrazolo[4,3-h]quinazoline-3-carboxamide;

46) N-(2,6-diethylphenyl)-8-({4-[(3S)-3-(dimethylamino)pyrrolidin-1-yl]-2-methoxyphenyl}amino)-1-methyl-4,5-dihydro-1H-pyrazolo[4,3-h]quinazoline-3-carboxamide;

47) N-(2,6-diethylphenyl)-8-({4-[(3R)-3-(dimethylamino)pyrrolidin-1-yl]-2-methoxyphenyl}amino)-1-methyl-4,5-dihydro-1H-pyrazolo[4,3-h]quinazoline-3-carboxamide;

48) 8-[(5-bromo-2-methoxyphenyl)amino]-N-(2,6-diethylphenyl)-1-methyl-4,5-dihydro-1H-pyrazolo[4,3-h]quinazoline-3-carboxamide;

49) N-(2,6-diethylphenyl)-8-{[2-methoxy-5-(4-methylpiperazin-1-yl)phenyl]amino}-1-methyl-4,5-dihydro-1H-pyrazolo[4,3-h]quinazoline-3-carboxamide;

50) N-(2,6-diethylphenyl)-8-({4-[4-(2-hydroxyethyl)piperazin-1-yl]-2-methoxyphenyl}amino)-1-methyl-4,5-dihydro-1H-pyrazolo[4,3-h]quinazoline-3-carboxamide;

51) N-(2,6-diethylphenyl)-8-[(4-{[2-(dimethylamino)ethyl]amino}-2-methoxyphenyl)amino]-1-methyl-4,5-dihydro-1H-pyrazolo[4,3-h]quinazoline-3-carboxamide;

52) N-(2,6-diethylphenyl)-8-({2-methoxy-4-[(4-methylpiperazin-1-yl)carbonyl]phenyl}amino)-1-methyl-4,5-dihydro-1H-pyrazolo[4,3-h]quinazoline-3-carboxamide;

53) tert-butyl 4-({3-[(2,6-diethylphenyl)carbamoyl]-1-methyl-4,5-dihydro-1H-pyrazolo[4,3-h]quinazolin-8-yl}amino)piperidine-1-carboxylate;

54) N-(2,6-diethylphenyl)-1-methyl-8-(piperidin-4-ylamino)-4,5-dihydro-1H-pyrazolo[4,3-h]quinazoline-3-carboxamide, hydrochloride;

55) N-(2,6-diethylphenyl)-8-{[1-(ethenylsulfonyl)piperidin-4-yl]amino}-1-methyl-4,5-dihydro-1H-pyrazolo[4,3-h]quinazoline-3-carboxamide;

56) N-(2,6-diethylphenyl)-1-methyl-8-[(1-{[2-(methylamino)ethyl]sulfonyl}piperidin-4-yl)amino]-4,5-dihydro-1H-pyrazolo[4,3-h]quinazoline-3-carboxamide;

57) N-(2,6-diethylphenyl)-1-methyl-8-[1-(methylsulfonyl)piperidin-4-yl]amino}-4,5-dihydro-1H-pyrazolo[4,3-h]quinazoline-3-carboxamide;

58) 8-[(1-acetylpiperidin-4-yl)amino]-N-(2,6-diethylphenyl)-1-methyl-4,5-dihydro-1H-pyrazolo[4,3-h]quinazoline-3-carboxamide;

59) N-(2,6-diethylphenyl)-1-methyl-8-{[1-(phenylcarbonyl)piperidin-4-yl]amino}-4,5-dihydro-1H-pyrazolo[4,3-h]quinazoline-3-carboxamide;

60) N-(2,6-diethylphenyl)-1-methyl-8-({1-[(1-methylpiperidin-4-yl)carbonyl]piperidin-4-yl}amino)-4,5-dihydro-1H-pyrazolo[4,3-h]quinazoline-3-carboxamide;

61) N-(2,6-diethylphenyl)-1-methyl-8-({1-[(4-methylpiperazin-1-yl)carbonyl]piperidin-4-yl}amino)-4,5-dihydro-1H-pyrazolo[4,3-h]quinazoline-3-carboxamide;

62) N-(2,6-diethylphenyl)-1-methyl-8-{[1-(phenylsulfonyl)piperidin-4-yl]amino}-4,5-dihydro-1H-pyrazolo[4,3-h]quinazoline-3-carboxamide;

63) 8-[(1-acryloylpiperidin-4-yl)amino]-N-(2,6-diethylphenyl)-1-methyl-4,5-dihydro-1H-pyrazolo[4,3-h]quinazoline-3-carboxamide;

64) 8-[(1-benzylpiperidin-4-yl)amino]-N-(2,6-diethylphenyl)-1-methyl-4,5-dihydro-1H-pyrazolo[4,3-h]quinazoline-3-carboxamide;

65) 8-({1-[(3-chloropropyl)sulfonyl]piperidin-4-yl}amino)-N-(2,6-diethylphenyl)-1-methyl-4,5-dihydro-1H-pyrazolo[4,3-h]quinazoline-3-carboxamide;

66) N-(2,6-diethylphenyl)-1-methyl-8-{[1-(N-methyl-beta-alanyl)piperidin-4-yl]amino}-4,5-dihydro-1H-pyrazolo[4,3-h]quinazoline-3-carboxamide;

67) N-(2,6-diethylphenyl)-8-{[1-(N,N-dimethyl-beta-alanyl)piperidin-4-yl]amino}-1-methyl-4,5-dihydro-1H-pyrazolo[4,3-h]quinazoline-3-carboxamide;

68) N-(2,6-diethylphenyl)-8-[(1-ethylpiperidin-4-yl)amino]-1-methyl-4,5-dihydro-1H-pyrazolo[4,3-h]quinazoline-3-carboxamide;

69) N-(2,6-diethylphenyl)-1-methyl-8-[(1-{[3-(methylamino)propyl]sulfonyl}piperidin-4-yl)amino]-4,5-dihydro-1H-pyrazolo[4,3-h]quinazoline-3-carboxamide, hydrochloride;

70) N-(2,6-diethylphenyl)-1-methyl-8-[(1-{[2-(4-methylpiperazin-1-yl)ethyl]sulfonyl}piperidin-4-yl)amino]-4,5-dihydro-1H-pyrazolo[4,3-h]quinazoline-3-carboxamide;

71) N-(2,6-diethylphenyl)-8-[(1-{[2-(dimethylamino)ethyl]sulfonyl}piperidin-4-yl)amino]-1-methyl-4,5-dihydro-1H-pyrazolo[4,3-h]quinazoline-3-carboxamide;

72) N-(2,6-diethylphenyl)-1-methyl-8-({1-[(2-piperidin-1-ylethyl)sulfonyl]piperidin-4-yl}amino)-4,5-dihydro-1H-pyrazolo[4,3-h]quinazoline-3-carboxamide;

73) N-(2,6-diethylphenyl)-1-methyl-8-({1-[(2-morpholin-4-ylethyl)sulfonyl]piperidin-4-yl}amino)-4,5-dihydro-1H-pyrazolo[4,3-h]quinazoline-3-carboxamide;

74) N-(2,6-diethylphenyl)-1-methyl-8-({1-[(2-pyrrolidin-1-ylethyl)sulfonyl]piperidin-4-yl}amino)-4,5-dihydro-1H-pyrazolo[4,3-h]quinazoline-3-carboxamide;

75) 8-({1-[(2-aminoethyl)sulfonyl]piperidin-4-yl}amino)-N-(2,6-diethylphenyl)-1-methyl-4,5-dihydro-1H-pyrazolo[4,3-h]quinazoline-3-carboxamide;

76) N-(2,6-diethylphenyl)-8-{[2-methoxy-4(4-pyrrolidin-1-ylpiperidin-1-yl)phenyl]amino}-1-methyl-4,5-dihydro-1H-pyrazolo[4,3-h]quinazoline-3-carboxamide;

77) N-(2,6-diethylphenyl)-8-{[2-methoxy-4-(tetrahydro-2H-pyran-4-ylamino)phenyl]amino}-1-methyl-4,5-dihydro-1H-pyrazolo[4,3-h]quinazoline-3-carboxamide;

78) tert-butyl 4-({3-[(2,6-diethylphenyl)carbamoyl]-1-methyl-4,5-dihydro-1H-pyrazolo[4,3-h]quinazolin-8-yl}amino)-3-methylbenzoate;

79) N-(2,6-diethylphenyl)-8-({2-methoxy-4-[(1-methylpiperidin-4-yl)amino]phenyl}amino)-1-methyl-4,5-dihydro-1H-pyrazolo[4,3-h]quinazoline-3-carboxamide;

80) 8-({1-[(3-chloromethyl)sulfonyl]piperidin-4-yl}amino)-N-(2,6-diethylphenyl)-1-methyl-4,5-dihydro-1H-pyrazolo[4,3-h]quinazoline-3-carboxamide;

81) 8-[(4-amino-2-methoxyphenyl)amino]-N-(2,6-diethylphenyl)-1-methyl-4,5-dihydro-1H-pyrazolo[4,3-h]quinazoline-3-carboxamide;

82) N-(2,6-diethylphenyl)-8-[(2-methoxy-4-{[(1-methylpiperidin-4-yl)carbonyl]amino}phenyl)amino]-1-methyl-4,5-dihydro-1H-pyrazolo[4,3-h]quinazoline-3-carboxamide;

83) 4-({3-[(2,6-diethylphenyl)carbamoyl]-1-methyl-4,5-dihydro-1H-pyrazolo[4,3-h]quinazolin-8-yl}amino)-3-methylbenzoic acid;
84) N-(2,6-diethylphenyl)-8-[(4-{[4-(dimethylamino)piperidin-1-yl]carbonyl}-2-methylphenyl)amino]-1-methyl-4,5-dihydro-1H-pyrazolo[4,3-h]quinazoline-3-carboxamide;
85) N-(2,6-diethylphenyl)-8-[(4-{[2-(dimethylamino)ethyl]carbamoyl}-2-methylphenyl)amino]-1-methyl-4,5-dihydro-1H-pyrazolo[4,3-h]quinazoline-3-carboxamide;
86) N-(2,6-diethylphenyl)-8-[(4-{[4-(dimethylamino)butanoyl]amino}-2-methoxyphenyl)amino]-1-methyl-4,5-dihydro-1H-pyrazolo[4,3-h]quinazoline-3-carboxamide trifluoroacetate;
87) 8-[(4-bromo-2-chlorophenyl)amino]-N-(2,6-diethylphenyl)-1-methyl-4,5-dihydro-1H-pyrazolo[4,3-h]quinazoline-3-carboxamide;
88) 8-{[2-chloro-4-(4-methylpiperazin-1-yl)phenyl]amino}-N-(2,6-diethylphenyl)-1-methyl-4,5-dihydro-1H-pyrazolo[4,3-h]quinazoline-3-carboxamide;
89) N-(2,6-diethylphenyl)-1-methyl-8-[(2-methyl-4-{[(2R)-2-(pyrrolidin-1-ylmethyl)pyrrolidin-1-yl]carbonyl}phenyl)amino]-4,5-dihydro-1H-pyrazolo[4,3-h]quinazoline-3-carboxamide;
90) 8-[(2-chloro-4-{[3-(dimethylamino)propyl](methyl)amino}phenyl)amino]-N-(2,6-diethylphenyl)-1-methyl-4,5-dihydro-1H-pyrazolo[4,3-h]quinazoline-3-carboxamide;
91) N-(2,6-diethylphenyl)-1-methyl-8-({2-methyl-4-[(4-methyl-1,4-diazepan-1-yl)carbonyl]phenyl}amino)-4,5-dihydro-1H-pyrazolo[4,3-h]quinazoline-3-carboxamide;
92) 8-({2-chloro-4-[4-(dimethylamino)piperidin-1-yl]phenyl}amino)-N-(2,6-diethylphenyl)-1-methyl-4,5-dihydro-1H-pyrazolo[4,3-h]quinazoline-3-carboxamide;
93) N-(2,6-diethylphenyl)-8-({4-[(4-hydroxycyclohexyl)amino]-2-methoxyphenyl}amino)-1-methyl-4,5-dihydro-1H-pyrazolo[4,3-h]quinazoline-3-carboxamide;
94) N-(2,6-diethylphenyl)-8-({2-methoxy-4-[(3-piperidin-1-ylpropanoyl)amino]phenyl}amino)-1-methyl-4,5-dihydro-1H-pyrazolo[4,3-h]quinazoline-3-carboxamide;
95) N-(2,6-diethylphenyl)-1-methyl-8-({2-methyl-4-[(4-pyrrolidin-1-ylpiperidin-1-yl)carbonyl]phenyl}amino)-4,5-dihydro-1H-pyrazolo[4,3-h]quinazoline-3-carboxamide;
96) 8-{[4-(1-azabicyclo[2.2.2]oct-3-ylamino)-2-methoxyphenyl]amino}-N-(2,6-diethylphenyl)-1-methyl-4,5-dihydro-1H-pyrazolo[4,3-h]quinazoline-3-carboxamide;
97) 8-{[4-({[tert-butyl(dimethyl)silyl]oxy}methyl)-2-methoxyphenyl]amino}-N-(2,6-diethylphenyl)-1-methyl-4,5-dihydro-1H-pyrazolo[4,3-h]quinazoline-3-carboxamide;
98) N-(2,6-diethylphenyl)-8-{[4-(hydroxymethyl)-2-methoxyphenyl]amino}-1-methyl-4,5-dihydro-1H-pyrazolo[4,3-h]quinazoline-3-carboxamide;
99) N-(2,6-diethylphenyl)-8-({2-methoxy-4-[(4-methylpiperazin-1-yl)methyl]phenyl}amino)-1-methyl-4,5-dihydro-1H-pyrazolo[4,3-h]quinazoline-3-carboxamide;
100) tert-butyl 4-({3-[(2,6-diethylphenyl)carbamoyl]-1-methyl-4,5-dihydro-1H-pyrazolo[4,3-h]quinazolin-8-yl}amino)-3,3-dimethylpiperidine-1-carboxylate;
101) N-(2,6-diethylphenyl)-8-[(3,3-dimethyl-1-{[2-(methylamino)ethyl]sulfonyl}piperidin-4-yl)amino]-1-methyl-4,5-dihydro-1H-pyrazolo[4,3-h]quinazoline-3-carboxamide;
102) N-(2,6-diethylphenyl)-1-methyl-8-({1-[(2,2,2-trifluoroethyl)sulfonyl]piperidin-4-yl}amino)-4,5-dihydro-1H-pyrazolo[4,3-h]quinazoline-3-carboxamide;
103) N-(2,6-diethylphenyl)-1-methyl-8-({1-[(trifluoromethyl)sulfonyl]piperidin-4-yl}amino)-4,5-dihydro-1H-pyrazolo[4,3-h]quinazoline-3-carboxamide;
104) N-(2,6-diethylphenyl)-1-methyl-8-{[1-(1H-pyrazol-4-ylsulfonyl)piperidin-4-yl]amino}-4,5-dihydro-1H-pyrazolo[4,3-h]quinazoline-3-carboxamide;
105) N-(2,6-diethylphenyl)-8-{[1-(1H-imidazol-4-ylsulfonyl)piperidin-4-yl]amino}-1-methyl-4,5-dihydro-1H-pyrazolo[4,3-h]quinazoline-3-carboxamide;
106) N-(2,6-diethylphenyl)-1-methyl-8-({1-[(4-methyl-3,4-dihydro-2H-1,4-benzoxazin-7-yl)sulfonyl]piperidin-4-yl}amino)-4,5-dihydro-1H-pyrazolo[4,3-h]quinazoline-3-carboxamide;
107) N-(2,6-diethylphenyl)-8-{[1-(dimethylsulfamoyl)piperidin-4-yl]amino}-1-methyl-4,5-dihydro-1H-pyrazolo[4,3-h]quinazoline-3-carboxamide;
108) N-(2,6-diethylphenyl)-1-methyl-8-({1-[(1-methyl-1H-imidazol-4-yl)sulfonyl]piperidin-4-yl}amino)-4,5-dihydro-1H-pyrazolo[4,3-h]quinazoline-3-carboxamide;
109) N-(2,6-diethylphenyl)-1-methyl-8-{[1-(pyridin-3-ylsulfonyl)piperidin-4-yl]amino}-4,5-dihydro-1H-pyrazolo[4,3-h]quinazoline-3-carboxamide;
110) 8-[(1-{[4-(acetylamino)phenyl]sulfonyl}piperidin-4-yl)amino]-N-(2,6-diethylphenyl)-1-methyl-4,5-dihydro-1H-pyrazolo[4,3-h]quinazoline-3-carboxamide;
111) 8-({1-[(4-aminophenyl)sulfonyl]piperidin-4-yl}amino)-N-(2,6-diethylphenyl)-1-methyl-4,5-dihydro-1H-pyrazolo[4,3-h]quinazoline-3-carboxamide hydrochloride;
112) N-(2,6-diethylphenyl)-8-({1-[(2-hydroxyethyl)sulfonyl]piperidin-4-yl}amino)-1-methyl-4,5-dihydro-1H-pyrazolo[4,3-h]quinazoline-3-carboxamide;
113) N-(2,6-diethylphenyl)-8-({1-[(2-methoxyethyl)sulfonyl]piperidin-4-yl}amino)-1-methyl-4,5-dihydro-1H-pyrazolo[4,3-h]quinazoline-3-carboxamide;
114) 8-[(trans-4-aminocyclohexyl)amino]-N-(2,6-diethylphenyl)-1-methyl-4,5-dihydro-1H-pyrazolo[4,3-h]quinazoline-3-carboxamide;
115) N-(2,6-diethylphenyl)-8-[(1-{[2-(ethylamino)ethyl]sulfonyl}piperidin-4-yl)amino]-1-methyl-4,5-dihydro-1H-pyrazolo[4,3-h]quinazoline-3-carboxamide;
116) N-(2,6-diethylphenyl)-1-methyl-8-({1-[(5-methylisoxazol-4-yl)carbonyl]piperidin-4-yl}amino)-4,5-dihydro-1H-pyrazolo[4,3-h]quinazoline-3-carboxamide;
117) N-(2,6-diethylphenyl)-1-methyl-8-({1-[(1-methyl-1H-imidazol-4-yl)carbonyl]piperidin-4-yl}amino)-4,5-dihydro-1H-pyrazolo[4,3-h]quinazoline-3-carboxamide;
118) N-(2,6-diethylphenyl)-1-methyl-8-{[1-(pyrimidin-4-ylcarbonyl)piperidin-4-yl]amino}-4,5-dihydro-1H-pyrazolo[4,3-h]quinazoline-3-carboxamide;
119) N-(2,6-diethylphenyl)-1-methyl-8-{[1-(1H-pyrrol-2-ylcarbonyl)piperidin-4-yl]amino}-4,5-dihydro-1H-pyrazolo[4,3-h]quinazoline-3-carboxamide;
120) N-(2,6-diethylphenyl)-8-{[1-(1H-imidazol-4-ylcarbonyl)piperidin-4-yl]amino}-1-methyl-4,5-dihydro-1H-pyrazolo[4,3-h]quinazoline-3-carboxamide;

121) N-(2,6-diethylphenyl)-1-methyl-8-{[1-(pyridin-3-yl-carbonyl)piperidin-4-yl]amino}-4,5-dihydro-1H-pyrazolo[4,3-h]quinazoline-3-carboxamide;
122) N-(2,6-diethylphenyl)-1-methyl-8-{[1-(pyridin-2-yl-carbonyl)piperidin-4-yl]amino}-4,5-dihydro-1H-pyrazolo[4,3-h]quinazoline-3-carboxamide;
123) N-(2,6-diethylphenyl)-1-methyl-8-{[1-(1H-pyrazol-4-ylcarbonyl)piperidin-4-yl]amino}-4,5-dihydro-1H-pyrazolo[4,3-h]quinazoline-3-carboxamide;
124) N-(2,6-diethylphenyl)-1-methyl-8-{[1-(thiophen-3-ylcarbonyl)piperidin-4-yl]amino}-4,5-dihydro-1H-pyrazolo[4,3-h]quinazoline-3-carboxamide;
125) N-(2,6-diethylphenyl)-1-methyl-8-{[1-(pyridin-4-yl-carbonyl)piperidin-4-yl]amino}-4,5-dihydro-1H-pyrazolo[4,3-h]quinazoline-3-carboxamide;
126) N-(2,6-diethylphenyl)-1-methyl-8-{[1-(1H-pyrrol-3-ylcarbonyl)piperidin-4-yl]amino}-4,5-dihydro-1H-pyrazolo[4,3-h]quinazoline-3-carboxamide;
127) N-(2,6-diethylphenyl)-1-methyl-8-{[trans-4-({[2-(methylamino)ethyl]sulfonyl}amino)cyclohexyl]amino}-4,5-dihydro-1H-pyrazolo[4,3-h]quinazoline-3-carboxamide and
128) N-(2,6-diethylphenyl)-8-[(4-formyl-2-methoxyphenyl)amino]-1-methyl-4,5-dihydro-1H-pyrazolo[4,3-h]quinazoline-3-carboxamide.

9. A pharmaceutical composition comprising, as active ingredient, a compound of the formula (I) or a pharmaceutically acceptable salt thereof, as defined in any of claims 1 to 8, in admixture with an acceptable diluent or carrier.

10. A compound of the formula (I) or a pharmaceutically acceptable salt thereof, as defined in any of claims 1 to 8, for a therapeutic use.

11. A method for treating diseases caused by and/or associated with an altered protein kinase activity which comprises administering to a mammal in need thereof an effective amount of a compound of formula (I), as defined in claim 1.

12. The method of claim 11 wherein the mammal in need thereof is a human.

13. An in vitro method for inhibiting protein kinase activity which comprises contacting the said kinase with an effective amount of a compound of formula (I) as defined in claim 1.

* * * * *